(12) United States Patent
Lee et al.

(10) Patent No.: US 12,145,929 B2
(45) Date of Patent: Nov. 19, 2024

(54) PIPERIDINE DERIVATIVE AND PHARMACEUTICAL COMPOSITION FOR INHIBITING AUTOTAXIN COMPRISING SAME

(71) Applicant: NEXTGEN BIOSCIENCE CO., LTD., Seongnam-si (KR)

(72) Inventors: Bong Yong Lee, Seoul (KR); Young Ah Shin, Seongnam-si (KR); Mi Ji Lee, Anyang-si (KR); Eun Jeong Kim, Seongnam-si (KR); Shin Ae Kim, Suwon-si (KR); Na Ra Han, Yongin-si (KR); Soo Sung Kang, Bucheon-si (KR); Su Jae Yang, Seoul (KR); Minh Thanh La, Seoul (KR)

(73) Assignee: NEXTGEN BIOSCIENCE CO., LTD., Seongnam-si (KR)

( * ) Notice: Subject to any disclaimer, the term of this patent is extended or adjusted under 35 U.S.C. 154(b) by 0 days.

(21) Appl. No.: 18/560,806

(22) PCT Filed: Sep. 30, 2022

(86) PCT No.: PCT/KR2022/014774
§ 371 (c)(1),
(2) Date: Nov. 14, 2023

(87) PCT Pub. No.: WO2023/055178
PCT Pub. Date: Apr. 6, 2023

(65) Prior Publication Data
US 2024/0279216 A1    Aug. 22, 2024

(30) Foreign Application Priority Data
Oct. 1, 2021    (KR) .................. 10-2021-0130879

(51) Int. Cl.
| C07D 413/14 | (2006.01) |
| A61K 31/506 | (2006.01) |
| A61K 31/517 | (2006.01) |
| A61K 31/5377 | (2006.01) |
| C07D 401/14 | (2006.01) |
| C07D 417/14 | (2006.01) |

(52) U.S. Cl.
CPC .......... *C07D 413/14* (2013.01); *A61K 31/506* (2013.01); *A61K 31/517* (2013.01); *A61K 31/5377* (2013.01); *C07D 401/14* (2013.01); *C07D 417/14* (2013.01)

(58) Field of Classification Search
CPC .. C07D 413/14; C07D 401/14; C07D 417/14; A61K 31/506; A61K 31/517; A61K 31/5377
See application file for complete search history.

(56) References Cited

U.S. PATENT DOCUMENTS

| 2022/0204479 A1 | 6/2022 | Zhang et al. |
| 2023/0069174 A1 | 3/2023 | Li et al. |
| 2024/0050428 A1* | 2/2024 | Liu ............ C07D 401/14 |

FOREIGN PATENT DOCUMENTS

| EA | 201101400 A1 | 7/2012 |
| KR | 10-2007-0099047 A | 10/2007 |
| KR | 10-2019-0039537 A | 4/2019 |
| KR | 10-2021-0075110 A | 6/2021 |
| WO | 03/000665 A1 | 1/2003 |
| WO | 2010/115491 A2 | 10/2010 |
| WO | 2018/019929 A1 | 2/2018 |
| WO | 2018/212534 A1 | 11/2018 |
| WO | 2021/043260 A1 | 3/2021 |
| WO | 2021/115375 A1 | 6/2021 |

OTHER PUBLICATIONS

Office Action of corresponding Australian Application No. 2022356017 dated Feb. 12, 2024, 11 pages.
Chemical Abstract Compound, STN express. RN 1622506-83-5 (Sep. 12, 2004), 1 page.
Chemical Abstract Compound, STN express. RN 1622649-17-5 (Sep. 12, 2004), 1 page.
Office Action for corresponding KR Patent Application No. 10-2022-0125024, 10 pages, with translation.
Notice of Allowance for corresponding KR Patent Application No. 10-2022-0125024, 8 pages, with translation.
The Office Action issued on Apr. 26, 2024 in regards to the Russian Patent Application No. 2023132551, 15 pages.
The Office Action issued on May 28, 2024 in regards to the Japanese Patent Application No. 2023-577513, 4 pages.

* cited by examiner

*Primary Examiner* — Matthew P Coughlin
*Assistant Examiner* — Quincy A McKoy
(74) *Attorney, Agent, or Firm* — Vorys, Sater, Seymour and Pease LLP; Mih Suhn Koh

(57) ABSTRACT

Provided are a piperidine derivative compound, a hydrate thereof, a solvate thereof, or a pharmaceutically acceptable salt thereof; and a pharmaceutical composition for the prevention or treatment of diseases related to autotaxin activity, comprising same as an active ingredient, in which the piperidine derivative compound exhibits excellent inhibitory activity against autotaxin, and thus can be effectively used in the treatment and prevention of diseases related to autotaxin inhibition, such as fibrotic diseases, inflammatory diseases, autoimmune diseases, respiratory diseases, cardiovascular diseases, metabolic diseases, cancer and cancer metastasis, ocular diseases, cholestatic form and other forms of chronic pruritus, and acute or chronic organ transplant rejection.

15 Claims, No Drawings

PIPERIDINE DERIVATIVE AND PHARMACEUTICAL COMPOSITION FOR INHIBITING AUTOTAXIN COMPRISING SAME

FIELD

The present invention relates to novel piperidine derivatives, and more specifically, to novel piperidine derivatives and pharmaceutical compositions for inhibiting autotaxin comprising the same.

BACKGROUND

Autotaxin (ATX), also referred to as ectonucleotide pyrophosphatase/phosphodiesterase family member 2 (ENPP2), is a secreted enzyme that is important in the production of the lipid signaling molecule lysophosphatidic acid (LPA). Autotaxin exhibits lysophospholipase D activity, which converts lysophosphatidylcholine (LPC) to LPA. Thus, LPA levels in plasma and ascites are associated with ATX activity.

Plasma LPA is a bioactive lipid that affects the migration, proliferation, and survival of a variety of cell types. In addition, ATX-LPA signaling is involved in the physiological and pathophysiological processes of a variety of diseases, including neurological function, vascular development, cardiovascular physiology, tissue regeneration, immune system function, chronic inflammation, tumor metastasis and progression, organ fibrosis and obesity, and/or other metabolic diseases (e.g. diabetes mellitus).

Thus, increased ATX activity and increased LPA levels, altered expression of LPA receptor, and altered responses to LPA may be associated with the initiation, progression, and/or outcome of a variety of pathophysiological conditions involving the ATX/LPA signaling pathway. In particular, it is known to be associated with cancer, lymphocyte homing, chronic inflammation, neuropathic pain, fibrotic diseases (e.g. idiopathic pulmonary fibrosis, IPF), and thrombosis. Accordingly, it is necessary to reduce the levels of LPA and/or ATX that induces it in order to treat these diseases.

OBJECT OF THE INVENTION

The problem to be addressed by the present invention is to provide an autotaxin inhibitory compound with a novel structure that exhibits excellent inhibitory activity against autotaxin.

Further, the problem to be addressed by the present invention is to provide a pharmaceutical composition for autotaxin inhibition, comprising the autotaxin inhibitory compound with the novel structure.

Furthermore, the problem to be addressed by the present invention is to provide a method for inhibiting autotaxin, and treating and preventing diseases resulting therefrom, using the autotaxin inhibitory compound with the novel structure.

Furthermore, the problem to be addressed by the present invention is to provide a use of the autotaxin inhibitory compound with the novel structure for inhibiting autotaxin, and treating diseases resulting therefrom.

The problem to be addressed by the present invention is not limited to the problems mentioned above, and other technical problems not mentioned can be clearly understood by those skilled in the art from the description below.

SUMMARY

To address the problem above, according to one aspect of the present invention, there is provided piperidine derivative compounds represented by the following Formula 1, a hydrate thereof, a solvate thereof or a pharmaceutically acceptable salt thereof, wherein:

<Formula 1>

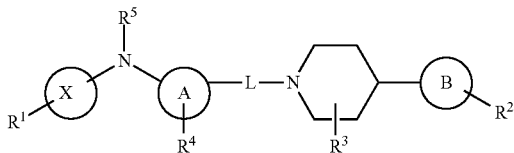

X is aryl Cia alkyl; a fused bicyclic ring in which aryl ring or heteroaryl ring having 1 to 3 of N is fused with non-aromatic cycloalkyl ring; or a fused bicyclic ring in which aryl ring is fused with non-aromatic heterocycle ring having 1 to 3 of O, wherein X is substituted with one or more $R^{10}$ or not, A is 5- to 6-membered heteroaryl having 1 to 3 heteroatom(s) selected from the group consisting of N, O and S, L is $C_{1-6}$ alkylene; —$(CH_2)_aCO$—; —$(CH)_aCO$—; —$(CH_2)_bO(CH_2)_cCO$—; or 5-membered aromatic or non-aromatic heterocycle having 1 to 3 heteroatom(s) selected from the group consisting of N and O, wherein said a, b, c are independently an integer from 1 to 5, B is COOH; $CH_2COOH$; CONHOH; $SO_2NH_2$; 4- to 5-membered non-aromatic heterocycle having 1 to 3 heteroatom(s) selected from the group consisting of N and O; or 5-membered heteroaryl having 1 to 4 heteroatom(s) selected from the group consisting of N and O, $R^1$ is halogen or $C_{1-4}$ alkylsulfonyl, $R^2$ is hydrogen, $C_{1-4}$ alkyl, $C_{1-4}$ haloalkyl, hydroxy, oxo (O) or aryl $C_{1-4}$ alkyl, $R^3$ is hydrogen, $C_{1-4}$ alkyl, $C_{1-4}$ alkoxy or halogen, $R^4$ is hydrogen, halogen or $C_{1-4}$ alkyl, $R^5$ is hydrogen or $C_{1-4}$ alkyl.

According to another aspect of the present invention, there is provided a pharmaceutical composition for preventing or treating a disease associated with autotaxin activity, comprising the piperidine derivative compound, a hydrate thereof, a solvate thereof or a pharmaceutically acceptable salt thereof as an active ingredient.

According to another aspect of the present invention, there is provided a method for inhibiting autotaxin, and treating or preventing diseases resulting therefrom, using the piperidine derivative compound, a hydrate thereof, a solvate thereof or a pharmaceutically acceptable salt thereof.

According to another aspect of the present invention, there is provided a use of the piperidine derivative compound, a hydrate thereof, a solvate thereof or a pharmaceutically acceptable salt thereof, for inhibiting autotaxin, and treating or preventing diseases resulting therefrom.

According to another aspect of the present invention, there is provided a pharmaceutical composition comprising the piperidine derivative compound, a hydrate thereof, a solvate thereof or a pharmaceutically acceptable salt thereof, and a pharmaceutically acceptable additive.

According to the present invention, it was found that the piperidine derivative of the novel structure of the present invention exhibits excellent inhibitory activity against autotaxin.

Therefore, the piperidine derivative of the novel structure of the present invention may be useful in the treatment and prevention of a disease associated with the autotaxin inhibition, such as fibrotic diseases, inflammatory diseases, autoimmune diseases, respiratory diseases, cardiovascular diseases, metabolic diseases, cancer and cancer metastasis, ocular diseases, cholestatic form and other forms of chronic pruritus, and acute or chronic organ transplant rejection.

The effect of the present invention is not limited to those described above, but should be understood to include all effects that can be inferred from the composition of the invention described in the detailed description or claims of the present invention.

DETAILED DESCRIPTION OF THE INVENTION

In the specification of the present invention, autotaxin (ATX) is a secreted enzyme that is important in the production of lysophosphatidic acid (LPA) and it is also referred to as ectonucleotide pyrophosphatase/phosphodiesterase family member 2 (ENPP2). Autotaxin exhibits lysophospholipase D activity, which converts lysophosphatidylcholine (LPC) to LPA. Thus, LPA levels in plasma and ascites are associated with ATX activity.

The present invention provides a piperidine derivative compound represented by the following Formula 1, a hydrate thereof, a solvate thereof or a pharmaceutically acceptable salt thereof, wherein:

<Formula 1>

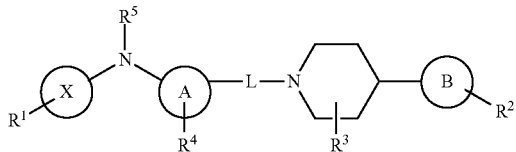

X is aryl $C_{1-4}$ alkyl; a fused bicyclic ring in which aryl ring or heteroaryl ring having 1 to 3 of N is fused with non-aromatic cycloalkyl ring; or a fused bicyclic ring in which aryl ring is fused with non-aromatic heterocycle ring having 1 to 3 of O, X is substituted with one or more $R^1$ or not, A is 5- to 6-membered heteroaryl having 1 to 3 heteroatom(s) selected from the group consisting of N, O and S, L is $C_{1-6}$ alkylene; —$(CH_2)_aCO$—; —$(CH)_aCO$—; —$(CH_2)_bO(CH_2)_cCO$—; or 5-membered aromatic or non-aromatic heterocycle having 1 to 3 heteroatom(s) selected from the group consisting of N and O, wherein said a, b, c are independently an integer from 1 to 5, B is COOH; $CH_2COOH$; CONHOH; $SO_2NH_2$; 4- to 5-membered non-aromatic heterocycle having 1 to 3 heteroatom(s) selected from the group consisting of N and O; or 5-membered heteroaryl having 1 to 4 heteroatom(s) selected from the group consisting of N and O, $R^1$ is halogen or $C_{1-4}$ alkylsulfonyl, $R^2$ is hydrogen, $C_{1-4}$ alkyl, $C_{1-4}$ haloalkyl, hydroxy, oxo (O) or aryl $C_{1-4}$ alkyl, $R^3$ is hydrogen, $C_{1-4}$ alkyl, $C_{1-4}$ alkoxy or halogen, $R^4$ is hydrogen, halogen or $C_{1-4}$ alkyl, $R^5$ is hydrogen or $C_{1-4}$ alkyl.

In one embodiment, X may be one selected from the group consisting of benzyl, phenethyl, dihydroindenyl, dihydrocyclopentapyrazinyl and benzodioxolyl.

In one embodiment, A may be one selected from the group consisting of pyridine, pyrimidine, pyridazine, pyrazine, oxadiazole and thiadiazole.

In one embodiment, L may be one selected from the group consisting of —$(CH_2)_3$—, —$(CH_2)_2CO$—, —$(CH_2)_3CO$—, —$(CH)_2CO$—, —$CH_2OCH_2CO$—, oxazole, isoxazole, dihydroisoxazole and oxadiazole.

In one embodiment, B may be one selected from the group consisting of carboxyl, carboxymethyl, carboxamido, sulfonamide, azetidine, morpholine, oxadiazole, imidazole, triazole and tetrazole.

In one embodiment, $R^1$ may be one selected from the group consisting of F, Cl, Br and methylsulfonyl.

In one embodiment, $R^2$ may be one selected from the group consisting of hydrogen, methyl, difluoromethyl, trifluoromethyl, hydroxy, oxo (O) and benzyl.

In one embodiment, $R^3$ may be one selected from the group consisting of hydrogen, methyl, methoxy and F.

In one embodiment, $R^4$ may be one selected from the group consisting of hydrogen, $C_1$ and methyl.

In one embodiment, $R^5$ may be hydrogen or alkyl.

Representative examples of piperidine derivative compounds according to the present invention are as follows:

[1] 5-(5-(4-(1H-1,2,3-triazol-5-yl)piperidin-1-yl)-1,3,4-oxadiazol-2-yl)-N-(2,3-dihydro-1H-inden-2-yl)pyrimidin-2-amine,

[2] 5-(5-(4-(1H-1,2,3-triazol-5-yl)piperidin-1-yl)-1,3,4-oxadiazol-2-yl)-N-(5-fluoro-2,3-dihydro-1H-inden-2-yl)pyrimidin-2-amine,

[3] 5-(5-(4-(1H-1,2,3-triazol-5-yl)piperidin-1-yl)-1,3,4-oxadiazol-2-yl)-N-(5-chloro-2,3-dihydro-1H-inden-2-yl)pyrimidin-2-amine,

[4] 5-(5-(4-(1H-1,2,3-triazol-5-yl)piperidin-1-yl)-1,3,4-oxadiazol-2-yl)-N-(5-bromo-2,3-dihydro-1H-inden-2-yl)pyrimidin-2-amine,

[5] 5-(5-(4-(1H-1,2,3-triazol-5-yl)piperidin-1-yl)-1,3,4-oxadiazol-2-yl)-N-(5,6-difluoro-2,3-dihydro-1H-inden-2-yl)pyrimidin-2-amine,

[6] 5-(5-(4-(1H-1,2,3-triazol-5-yl)piperidin-1-yl)-1,3,4-oxadiazol-2-yl)-N-(5,6-dichloro-2,3-dihydro-1H-inden-2-yl)pyrimidin-2-amine,

[7] N-(5-(5-(4-(1H-1,2,3-triazol-5-yl)piperidin-1-yl)-1,3,4-oxadiazol-2-yl)pyrimidin-2-yl)-6,7-dihydro-5H-cyclopenta[b]pyrazin-6-amine,

[8] 6-(5-(4-(1H-1,2,3-triazol-5-yl)piperidin-1-yl)-1,3,4-oxadiazol-2-yl)-N-(2,3-dihydro-1H-inden-2-yl)pyridazin-3-amine,

[9] 5-(5-(4-(1H-1,2,4-triazol-1-yl)piperidin-1-yl)-1,3,4-oxadiazol-2-yl)-N-(2,3-dihydro-1H-inden-2-yl)pyrimidin-2-amine,

[10] N-(2,3-dihydro-1H-inden-2-yl)-5-(5-(4-(3-methyl-TH-1,2,4-triazol-1-yl)piperidin-1-yl)-1,3,4-oxadiazol-2-yl)pyrimidin-2-amine,

[11] N-(5-bromo-2,3-dihydro-1H-inden-2-yl)-5-(5-(2-methyl-4-(1H-1,2,3-triazol-5-yl)piperidin-1-yl)-1,3,4-oxadiazol-2-yl)pyrimidin-2-amine,

[12] 5-(5-(4-(1H-1,2,3-triazol-5-yl)piperidin-1-yl)-1,3,4-oxadiazol-2-yl)-N-(5-bromo-2,3-dihydro-1H-inden-2-yl)pyridin-2-amine,

[13] 5-(5-(4-(1H-1,2,3-triazol-5-yl)piperidin-1-yl)-1,3,4-oxadiazol-2-yl)-N-(5-bromo-2,3-dihydro-1H-inden-2-yl)pyrazin-2-amine,

[14] 5-(5-(4-(1H-1,2,3-triazol-5-yl)piperidin-1-yl)-1,3,4-oxadiazol-2-yl)-N-(5-bromo-2,3-dihydro-1H-inden-2-yl)-4-chloropyridin-2-amine,

[15] 5-(5-(4-(1H-1,2,3-triazol-5-yl)piperidin-1-yl)-1,3,4-oxadiazol-2-yl)-N-(3,5-dichlorobenzyl)pyrimidin-2-amine,

[16] 5-(5-(4-(1H-1,2,3-triazol-5-yl)piperidin-1-yl)-1,3,4-oxadiazol-2-yl)-N-(3,5-dichlorophenethyl)pyrimidin-2-amine,

[17] 1-(4-(1H-1,2,3-triazol-5-yl)piperidin-1-yl)-3-(2-((2,3-dihydro-TH-inden-2-yl)amino)pyrimidin-5-yl)propan-1-one,

[18] 1-(4-(1H-imidazol-5-yl)piperidin-1-yl)-3-(2-((2,3-dihydro-TH-inden-2-yl)amino)pyrimidin-5-yl)propan-1-one,

[19] 1-(4-(1H-1,2,3-triazol-5-yl)piperidin-1-yl)-4-(5-((2,3-dihydro-TH-inden-2-yl)amino)-1,3,4-thiadiazol-2-yl)butan-1-one,

[20] 1-(4-(1H-imidazol-5-yl)piperidin-1-yl)-4-(5-((2,3-dihydro-TH-inden-2-yl)amino)-1,3,4-thiadiazol-2-yl)butan-1-one,

[21] 1-(4-(1H-1,2,3-triazol-5-yl)piperidin-1-yl)-4-(5-((2,3-dihydro-TH-inden-2-yl)amino)-1,3,4-oxadiazol-2-yl)butan-1-one,

[22] 1-(4-(1H-imidazol-5-yl)piperidin-1-yl)-4-(5-((2,3-dihydro-TH-inden-2-yl)amino)-1,3,4-oxadiazol-2-yl)butan-1-one,

[23] 1-(4-(1H-1,2,3-triazol-5-yl)piperidin-1-yl)-2-((5-((2,3-dihydro-TH-inden-2-yl)amino)-1,3,4-thiadiazol-2-yl)methoxy)ethan-1-one,

[24] N-(5,6-difluoro-2,3-dihydro-TH-inden-2-yl)-5-(5-(4-(5-(trifluoromethyl)-1,3,4-oxadiazol-2-yl)piperidin-1-yl)-1,3,4-oxadiazol-2-yl)pyrimidin-2-amine,

[25] N-(5,6-difluoro-2,3-dihydro-TH-inden-2-yl)-5-(5-(4-(5-(difluoromethyl)-1,3,4-oxadiazol-2-yl)piperidin-1-yl)-1,3,4-oxadiazol-2-yl)pyrimidin-2-amine,

[26] 5-(5-(4-(1,2,4-oxadiazol-3-yl)piperidin-1-yl)-1,3,4-oxadiazol-2-yl)-N-(5,6-difluoro-2,3-dihydro-1H-inden-2-yl)pyrimidin-2-amine,

[27] 5-(5-(4-(1,3,4-oxadiazol-2-yl)piperidin-1-yl)-1,3,4-oxadiazol-2-yl)-N-(5,6-difluoro-2,3-dihydro-1H-inden-2-yl)pyrimidin-2-amine,

[28] 5-(5-(4-(1H-tetrazol-1-yl)piperidin-1-yl)-1,3,4-oxadiazol-2-yl)-N-(5,6-difluoro-2,3-dihydro-1H-inden-2-yl)pyrimidin-2-amine,

[29] N-(5,6-difluoro-2,3-dihydro-1H-inden-2-yl)-5-(5-(4-(4-methyl-1H-1,2,3-triazol-5-yl)piperidin-1-yl)-1,3,4-oxadiazol-2-yl)pyrimidin-2-amine,

[30] (E)-1-(4-(1H-1,2,3-triazol-5-yl)piperidin-1-yl)-3-(2-((5,6-difluoro-2,3-dihydro-1H-inden-2-yl)amino)pyrimidin-5-yl)prop-2-en-1-one,

[31] 5-(5-(4-(1-benzyl-1H-1,2,3-triazol-5-yl)piperidin-1-yl)oxazol-2-yl)-N-(2,3-dihydro-1H-inden-2-yl)pyrimidin-2-amine,

[32] 5-(5-(4-(1H-1,2,3-triazol-5-yl)piperidin-1-yl)-1,3,4-oxadiazol-2-yl)-N-(5,6-difluoro-2,3-dihydro-1H-inden-2-yl)-N-methylpyrimidin-2-amine,

[33] N-(5,6-difluoro-2,3-dihydro-1H-inden-2-yl)-5-(5-(4-(1-methyl-1H-1,2,3-triazol-5-yl)piperidin-1-yl)-1,3,4-oxadiazol-2-yl)pyrimidin-2-amine,

[34] N-(5,6-difluoro-2,3-dihydro-1H-inden-2-yl)-5-(5-(4-(1-methyl-1H-1,2,3-triazol-4-yl)piperidin-1-yl)-1,3,4-oxadiazol-2-yl)pyrimidin-2-amine,

[35] N-indan-2-yl-5-[3-[4-(1H-triazol-5-yl)-1-piperidyl]-4,5-dihydroisoxazol-5-yl]pyrimidin-2-amine,

[36] 5-(3-(4-(1H-1,2,3-triazol-5-yl)piperidin-1-yl)isoxazol-5-yl)-N-(2,3-dihydro-1H-inden-2-yl)pyrimidin-2-amine,

[37] N-(5,6-difluoroindan-2-yl)-5-[3-[4-(1H-triazol-5-yl)-1-piperidyl]-4,5-dihydroisoxazol-5-yl]pyrimidin-2-amine,

[38] 5-(3-(4-(1H-1,2,3-triazol-5-yl)piperidin-1-yl)isoxazol-5-yl)-N-(5,6-difluoro-2,3-dihydro-1H-inden-2-yl)pyrimidin-2-amine,

[39] 5-(3-(4-(1H-1,2,3-triazol-5-yl)piperidin-1-yl)-4,5-dihydroisoxazol-5-yl)-N-(5-fluoro-2,3-dihydro-1H-inden-2-yl)pyrimidin-2-amine,

[40] 5-(3-(4-(1H-1,2,3-triazol-5-yl)piperidin-1-yl)isoxazol-5-yl)-N-(5-fluoro-2,3-dihydro-1H-inden-2-yl)pyrimidin-2-amine,

[41] N-[(3,5-difluorophenyl)methyl]-5-[3-[4-(1H-triazol-5-yl)-1-piperidyl]-4,5-dihydroisoxazol-5-yl]pyrimidin-2-amine,

[42] N-benzyl-5-[3-[4-(1H-triazol-5-yl)-1-piperidyl]-4,5-dihydroisoxazol-5-yl]pyrimidin-2-amine,

[43] N-[(3,4-difluorophenyl)methyl]-5-[3-[4-(1H-triazol-5-yl)-1-piperidyl]-4,5-dihydroisoxazol-5-yl]pyrimidin-2-amine,

[44] 5-(3-(4-(1H-1,2,3-triazol-5-yl)piperidin-1-yl)-4,5-dihydroisoxazol-5-yl)-N-(3,5-dichlorobenzyl)pyrimidin-2-amine,

[45] 5-(3-(4-(1H-1,2,3-triazol-5-yl)piperidin-1-yl)-4,5-dihydroisoxazol-5-yl)-N-(benzo[d][1,3]dioxol-5-ylmethyl)pyrimidin-2-amine,

[46] N-(1,3-benzodioxol-5-ylmethyl)-5-[3-[4-(1H-triazol-5-yl)-1-piperidyl]isoxazol-5-yl]pyrimidin-2-amine,

[47] 5-(3-(4-(1H-1,2,3-triazol-5-yl)piperidin-1-yl)-4,5-dihydroisoxazol-5-yl)-N-(3,5-dichlorophenethyl)pyrimidin-2-amine,

[48] 5-(3-(4-(1H-1,2,3-triazol-5-yl)piperidin-1-yl)-4,5-dihydroisoxazol-5-yl)-N-(3-(methylsulfonyl)benzyl)pyrimidin-2-amine,

[49] 5-(3-(4-(1H-1,2,3-triazol-5-yl)piperidin-1-yl)-4,5-dihydroisoxazol-5-yl)-N-(4-(methylsulfonyl)benzyl)pyrimidin-2-amine,

[50] 5-(3-(4-(1H-tetrazol-5-yl)piperidin-1-yl)-4,5-dihydroisoxazol-5-yl)-N-(2,3-dihydro-1H-inden-2-yl)pyrimidin-2-amine,

[51] 5-(3-(4-(5-(difluoromethyl)-1,3,4-oxadiazol-2-yl)piperidin-1-yl)-4,5-dihydroisoxazol-5-yl)-N-(2,3-dihydro-TH-inden-2-yl)pyrimidin-2-amine,

[52] 5-(3-(4-(1H-tetrazol-5-yl)piperidin-1-yl)-4,5-dihydroisoxazol-5-yl)-N-(5,6-difluoro-2,3-dihydro-1H-inden-2-yl)pyrimidin-2-amine,

[53] N-(5-fluoro-2,3-dihydro-TH-inden-2-yl)-5-(3-(4-(5-(trifluoromethyl)-1,3,4-oxadiazol-2-yl)piperidin-1-yl)-4,5-dihydroisoxazol-5-yl)pyrimidin-2-amine,

[54] N-(5,6-difluoro-2,3-dihydro-TH-inden-2-yl)-5-(5-(2-methyl-4-(1H-1,2,3-triazol-5-yl)piperidin-1-yl)-1,3,4-oxadiazol-2-yl)pyrimidin-2-amine,

[55] 5-(5-(4-(1H-1,2,3-triazol-5-yl)piperidin-1-yl)-1,3,4-oxadiazol-2-yl)-N-(benzo[d][1,3]dioxol-5-ylmethyl)pyrimidin-2-amine,

[56] 5-(5-(4-(1H-1,2,3-triazol-5-yl)piperidin-1-yl)-1,3,4-oxadiazol-2-yl)-N-(3,4-dichlorobenzyl)pyrimidin-2-amine,

[57] 5-(5-(4-(1H-1,2,3-triazol-5-yl)piperidin-1-yl)-1,3,4-oxadiazol-2-yl)-N-(3,5-difluorobenzyl)pyrimidin-2-amine,

[58] 5-(5-(4-(1H-1,2,3-triazol-5-yl)piperidin-1-yl)-1,3,4-oxadiazol-2-yl)-N-(3,4-difluorobenzyl)pyrimidin-2-amine,

[59] 5-(5-(4-(1H-1,2,3-triazol-5-yl)piperidin-1-yl)-1,3,4-oxadiazol-2-yl)-N-(3,5-dibromobenzyl)pyrimidin-2-amine,

[60] 5-(5-(4-(1H-1,2,3-triazol-5-yl)piperidin-1-yl)-1,3,4-oxadiazol-2-yl)-N-(5-bromo-2,3-dihydro-1H-inden-2-yl)-4-methylpyrimidin-2-amine,

[61] 5-(5-(4-(1H-1,2,3-triazol-5-yl)piperidin-1-yl)-1,3,4-oxadiazol-2-yl)-N-(5,6-dibromo-2,3-dihydro-TH-inden-2-yl)-4-methylpyrimidin-2-amine,
[62] 5-(3-(4-(1H-1,2,3-triazol-4-yl)piperidin-1-yl)propyl)-N-(2,3-dihydro-TH-inden-2-yl)pyrimidin-2-amine,
[63] N-(5,6-difluoro-2,3-dihydro-TH-inden-2-yl)-5-(5-(4-morpholinopiperidin-1-yl)-1,3,4-oxadiazol-2-yl)pyrimidin-2-amine,
[64] 1-(1-(5-(2-((5,6-difluoro-2,3-dihydro-1H-inden-2-yl)amino)pyrimidin-5-yl)-1,3,4-oxadiazol-2-yl)piperidin-4-yl)azetidin-3-ol,
[65] 1-(5-(2-((5,6-difluoro-2,3-dihydro-TH-inden-2-yl)amino)pyrimidin-5-yl)-1,3,4-oxadiazol-2-yl)piperidine-4-sulfonamide,
[66] 5-(1-(5-(2-((5,6-difluoro-2,3-dihydro-1H-inden-2-yl)amino)pyrimidin-5-yl)-1,3,4-oxadiazol-2-yl)piperidin-4-yl)-1,3,4-oxadiazol-2(3H)-one,
[67] 1-(5-(2-((5,6-difluoro-2,3-dihydro-TH-inden-2-yl)amino)pyrimidin-5-yl)-1,3,4-oxadiazol-2-yl)piperidine-4-carboxylic acid,
[68] 2-(1-(5-(2-((5,6-difluoro-2,3-dihydro-1H-inden-2-yl)amino)pyrimidin-5-yl)-1,3,4-oxadiazol-2-yl)piperidin-4-yl)acetic acid,
[69] 1-(5-(2-((5,6-difluoro-2,3-dihydro-TH-inden-2-yl)amino)pyrimidin-5-yl)-1,3,4-oxadiazol-2-yl)-N-hydroxypiperidine-4-carboxamide,
[70] N-(5,6-difluoro-2,3-dihydro-TH-inden-2-yl)-5-(5-(4-methoxy-4-(1H-1,2,3-triazol-4-yl)piperidin-1-yl)-1,3,4-oxadiazol-2-yl)pyrimidin-2-amine, and
[71] N-(5,6-difluoro-2,3-dihydro-TH-inden-2-yl)-5-(5-(4-fluoro-4-(1H-1,2,3-triazol-5-yl)piperidin-1-yl)-1,3,4-oxadiazol-2-yl)pyrimidin-2-amine.

This specification uses the following definitions when defining the compound of Formula 1 unless specifically defined.

The term "alkyl" refers to a straight or branched chain hydrocarbonyl group, preferably $C_1$-$C_{10}$ alkyl. Examples of alkyl include, but are not limited to, methyl, ethyl, n-propyl, iso-propyl, n-butyl, iso-butyl, tert-butyl, n-pentyl, iso-pentyl, n-hexyl, 3-methylhexyl, 2,2-dimethylpentyl, 2,3-dimethylpentyl, n-heptyl, n-octyl, n-nonyl and n-decyl.

The term "alkylene" refers to a divalent functional group derived from alkyl group, and preferably include 1 to 10 carbon atoms, but are not limited thereto. Examples of alkylene include, but are not limited to, —$CH_2$—, —$CH_2CH_2$—, —$CH_2CH_2CH_2$—, —$CH_2CH_2CH_2CH_2$— and —$CH_2CH_2CH_2CH_2CH_2$—.

The term "cycloalkyl" refers to a partially or fully saturated single or fused ring hydrocarbon, preferably $C_3$-$C_{10}$-cycloalkyl. Examples of cycloalkyl include, but are not limited to, cyclopropyl, cyclobutyl, cyclopentyl, cyclohexyl, and cyclohexenyl.

The term "hydroxy" is defined as —OH, and the term "alkoxy" means alkyloxy, a radical in which the hydrogen atom of the hydroxy group is substituted by 1 to 10 alkyl, unless otherwise defined.

The term "halogen" or "halo" refers to fluorine (F), chlorine (Cl), bromine (Br) or iodine (I).

The term "haloalkyl" and "haloalkoxy" means alkyl or alkoxy substituted with one or more halogen atoms.

The term "heteroatom" means N, O or S.

The term "aryl" means aromatic hydrocarbon, includes a polycycle aromatic ring system in which a carbocycle aromatic ring or heteroaryl ring is fused with one or more other rings, preferably $C_5$-$C_{12}$ aryl, more preferably $C_5$-$C_{10}$ aryl. For example, aryl includes, but are not limited to, phenyl, naphthyl, tetrahydronaphthyl, etc.

In addition, aryl includes a heteroaryl ring fused to cycloalkyl or non-aromatic heterocycle ring, for example, dihydrocyclopentapyrazinyl.

The term "heteroaryl" or "aromatic heterocycle" means a 3- to 12-membered, more preferably 5- to 10-membered aromatic hydrocarbon forming a single or fused ring that contains one or more heteroatoms selected from N, O and S as ring atoms, and that can be fused with a benzo or $C_3$-$C_8$ cycloalkyl. For example, heteroaryl includes, but are not limited to, pyrrolyl, imidazolyl, pyrazolyl, triazolyl, pyridyl, pyrazinyl, pyrimidyl, pyridazinyl, triazinyl, oxadiazolyl, isoxadiazolyl, tetrazolyl, indolyl, indazolyl, isoxazolyl, oxazolyl, thiazolyl, isothiazolyl, furanyl, benzofuranyl, thiophenyl, benzothiazolyl, benzooxazolyl, benzimidazolyl, quinolinyl, isoquinolinyl, etc.

Arylalkyl, alkylaryl and heteroarylalkyl refer to a group formed by combining aryl and alkyl or heteroaryl and alkyl as defined above, and include, for example, benzyl, phenethyl, etc, but are not limited thereto.

The compound represented by Formula 1 according to the present invention can be prepared and used in the form of prodrugs, hydrates, solvates and pharmaceutically acceptable salts to enhance in vivo absorption or increase solubility, so the prodrugs, hydrates, solvates and pharmaceutically acceptable salts are also within the scope of the present invention. In addition, the compound represented by Formula 1 has a chiral carbon, so that there exist stereoisomers of it, and these stereoisomers are also included within the scope of the present invention.

The term "prodrug" refers to a substance that is transformed in vivo into a parent drug. Prodrugs are often used because, in some cases, they are easier to administer than the parent drug. For example, they may be bioavailable by oral administration, whereas the parent drug may not be. Prodrugs may also have improved solubility in pharmaceutical compositions than the parent drug. For example, a prodrug may be an in vivo hydrolysable ester of the compound according to the present invention and a pharmaceutically acceptable salt thereof. Another example of a prodrug may be a short peptide (polyamino acid) in which the peptide is coupled to an acid group that is metabolically converted to reveal the active site.

The term "hydrate" refers to a compound of the present invention or a salt thereof containing a stoichiometric or non-stoichiometric amount of water bound by non-covalent intermolecular forces.

The term "solvate" refers to a compound of the present invention or a salt thereof containing a stoichiometric or non-stoichiometric amount of solvent bound by non-covalent intermolecular forces. Preferred solvents therefor include solvents that are volatile, non-toxic, and/or suitable for administration to humans.

The term "isomer" refers to a compound of the present invention or a salt thereof that has the same chemical formula or molecular formula but is structurally or sterically different. Such isomers include both structural isomer such as tautomer, and stereoisomers such as R or S isomers with asymmetric carbon center and geometric isomers (trans, cis). All of these isomers and their mixtures thereof are also included within the scope of the present invention.

The term "pharmaceutically acceptable salt" refers to a salt form of a compound that does not cause serious irritation to the organism to which the compound is administered and does not impair the biological activity and physical properties of the compound. The pharmaceutical salts include an acid addition salt formed by an acid containing a pharmaceutically acceptable anion and forming a non-toxic acid addition salt, for example, inorganic acids such as hydrochloric acid, sulfuric acid, nitric acid, phosphoric acid, hydrobromic acid, hydrogen iodide, etc., organic carbon acids such as tartaric acid, formic acid, citric acid, acetic acid, trichloroacetic acid, trifluoroacetic acid, gluconic acid, benzoic acid, lactic acid, fumaric acid, malic acid, salicylic acid, etc., sulfonic acids such as methanesulfonic acid, ethanesulfonic acid, benzenesulfonic acid, p-toluenesulfonic acid, etc. For example, pharmaceutically acceptable carboxylic acid salts include metal salts or alkaline earth metal salts formed by lithium, sodium, potassium, calcium, magnesium, etc., amino acid salts such as lysine, arginine, guanidine, etc., organic salts such as dicyclohexylamine, N-methyl-D-glucamine, tris(hydroxymethyl)methylamine, diethanolamine, choline and triethylamine etc. The compound of Formula 1 according to the present invention can also be converted into its salt by conventional methods.

In addition, the present invention provides a process for synthesizing the compound represented by Formula 1.

Schemes 1 to 26 are illustrated as a process for synthesizing the compound of Formula 1 of the present invention, and the following process for synthesizing is not intended to be limiting to methods of preparing a compound of Formula 1 according to the present invention. It is obvious that the process for synthesis in Schemes 1 to 26 below is illustrative only, and can be easily modified by those skilled in the art depending on the specific substituent.

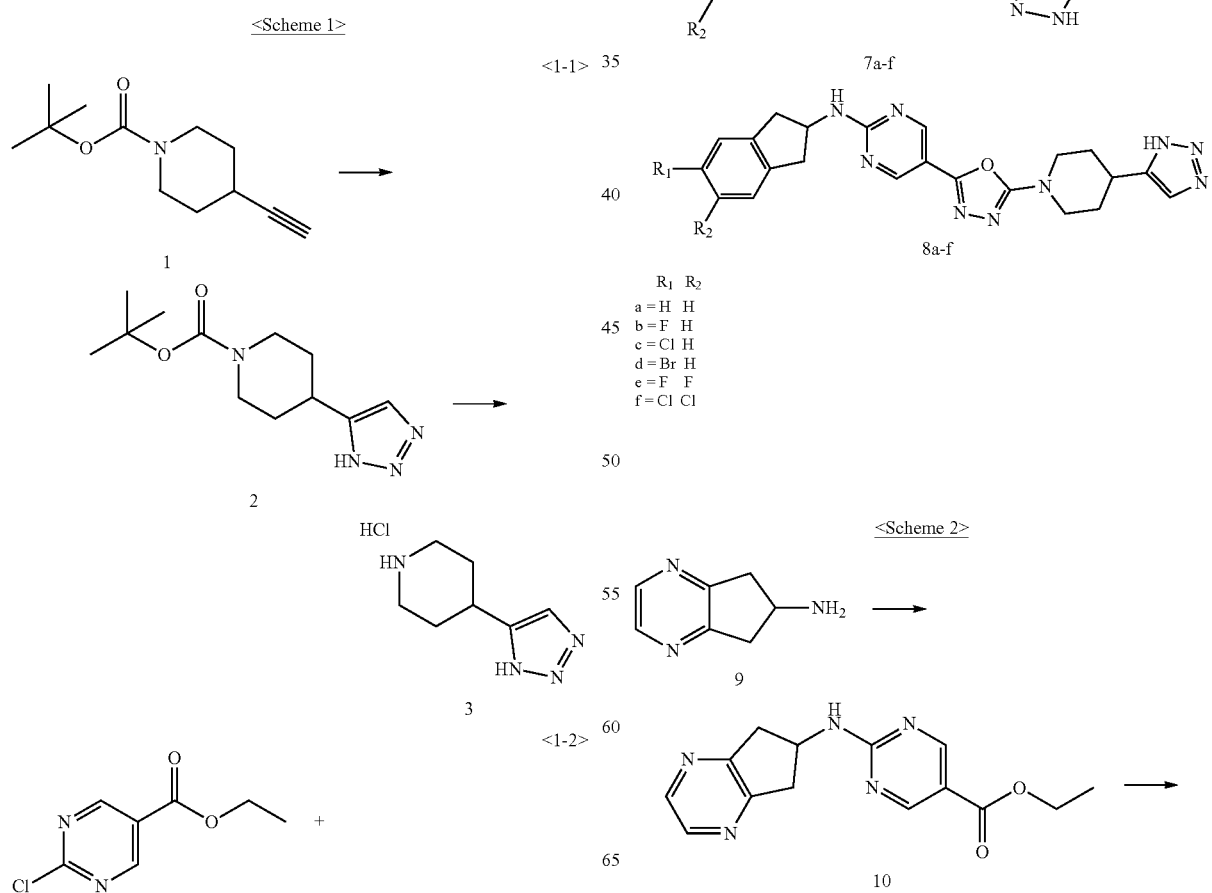

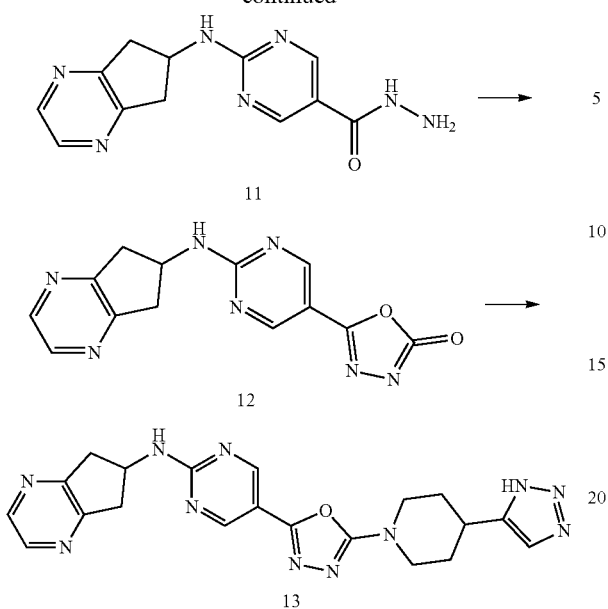
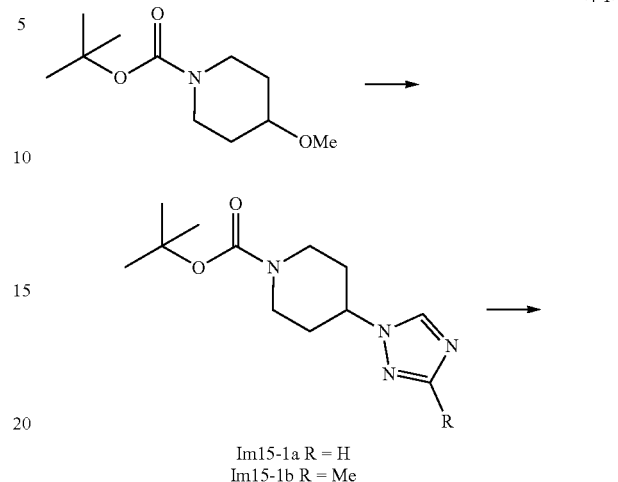
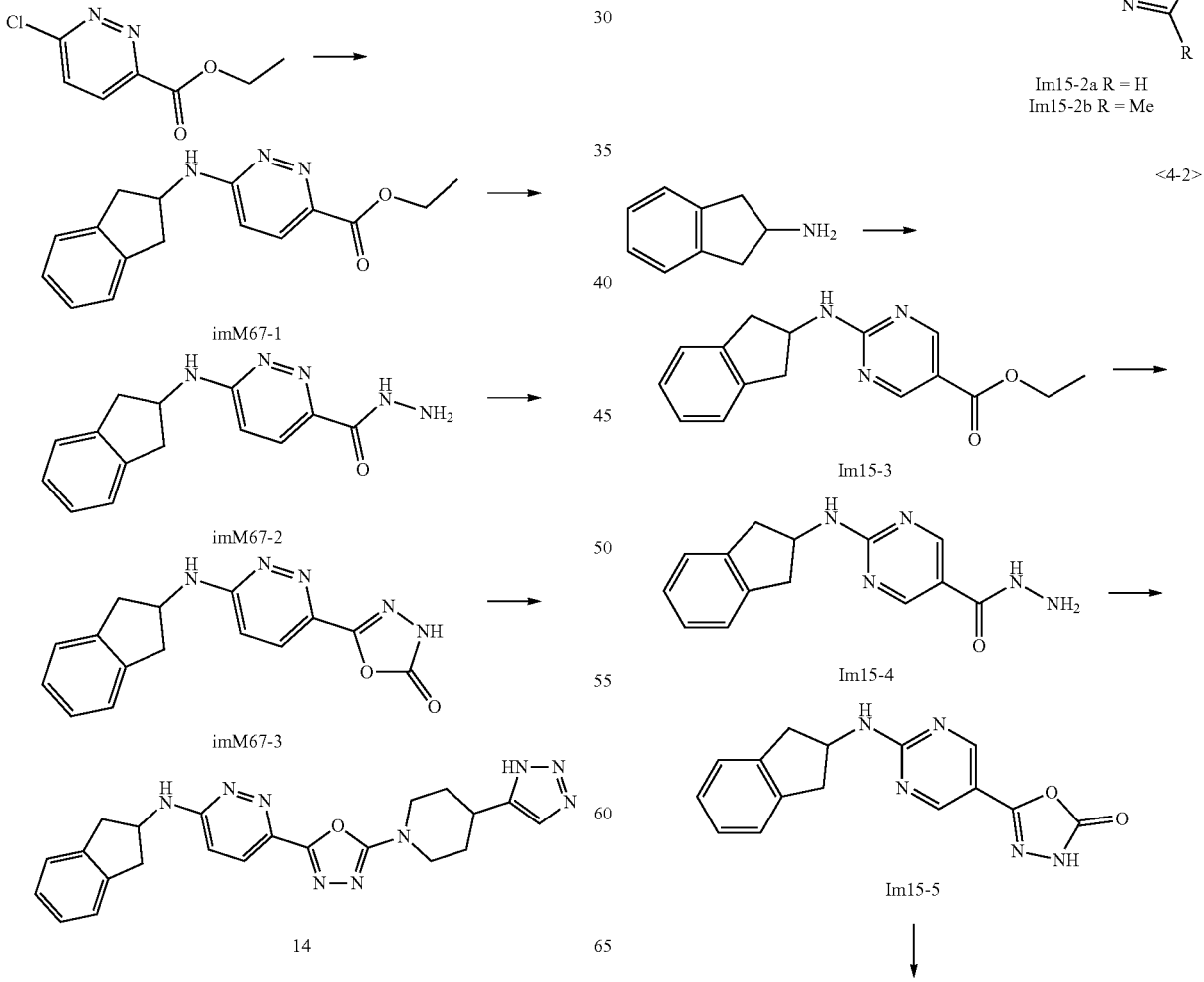

-continued
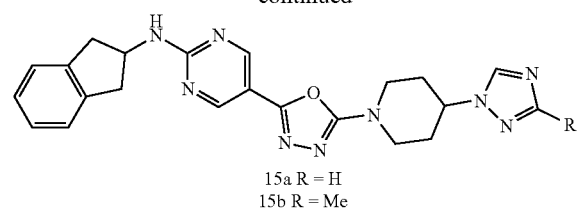
15a R = H
15b R = Me
<Scheme 6>
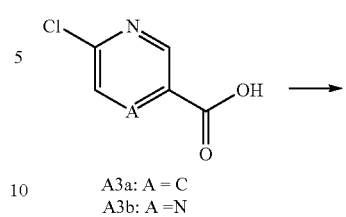
A3a: A = C
A3b: A = N
<Scheme 5>
<5-1>
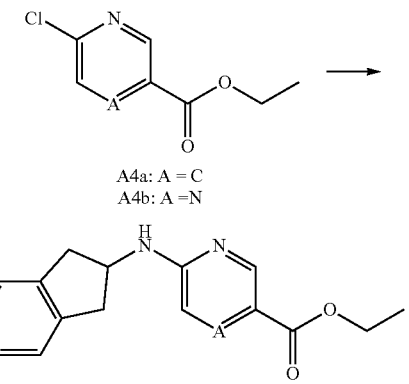
A4a: A = C
A4b: A = N
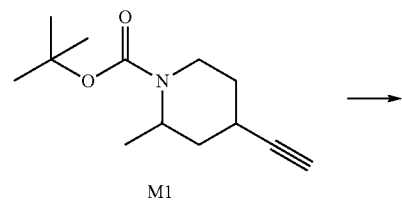
M1
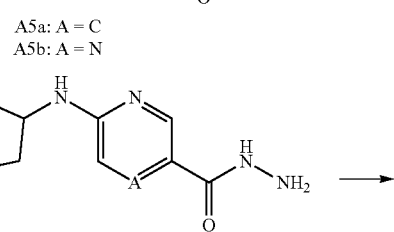
A5a: A = C
A5b: A = N
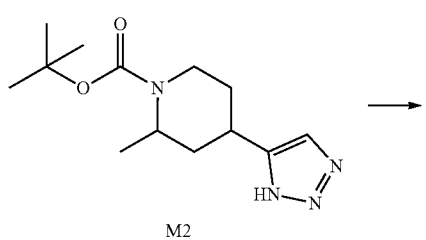
M2
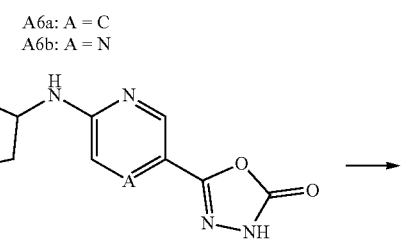
A6a: A = C
A6b: A = N
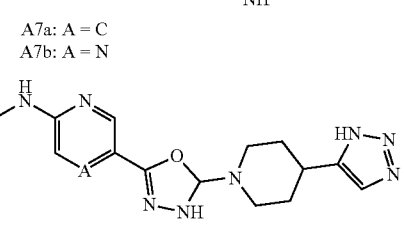
A7a: A = C
A7b: A = N
M3
<5-2>
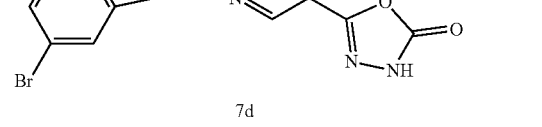
7d
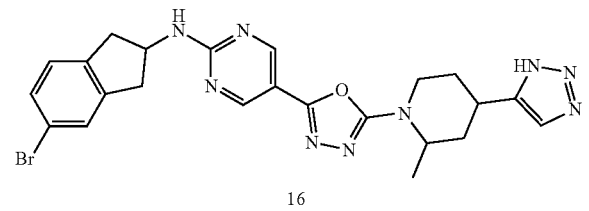
17a: A = C
17b: A = N
16
<Scheme 7>
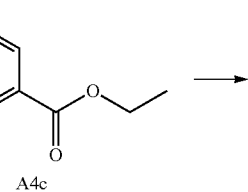
A4c

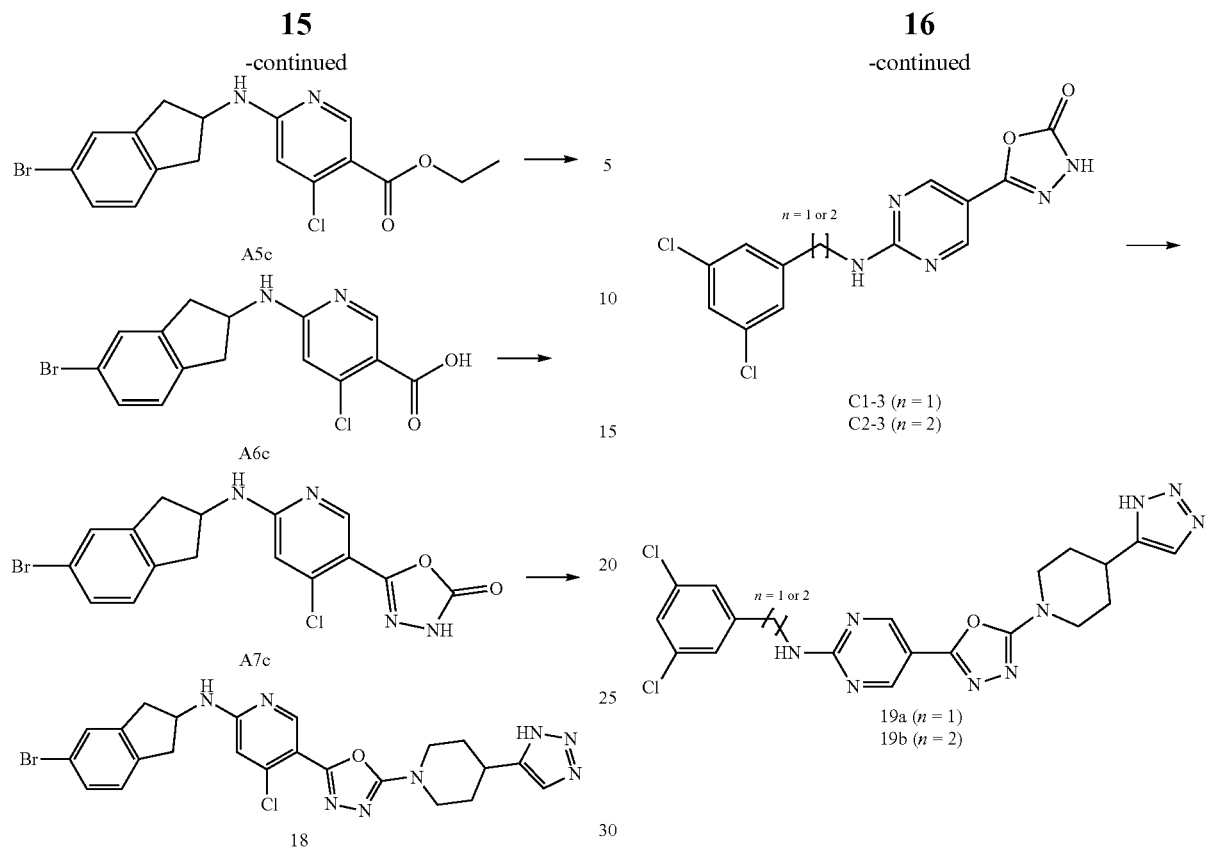
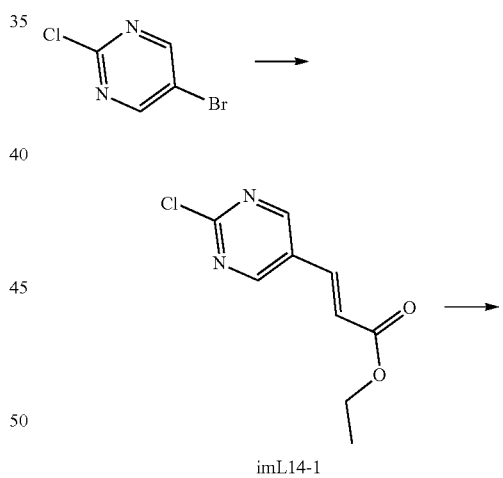
<Scheme 8>
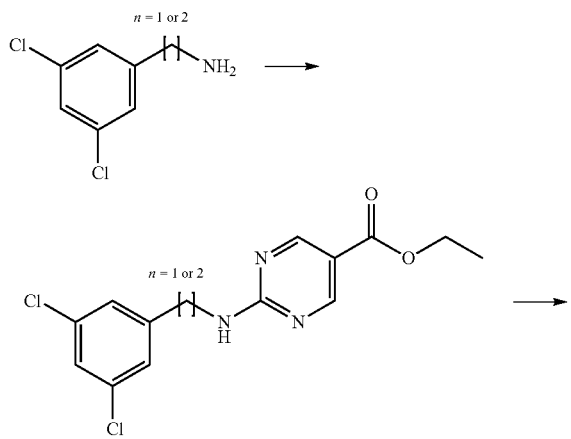
<Scheme 9>
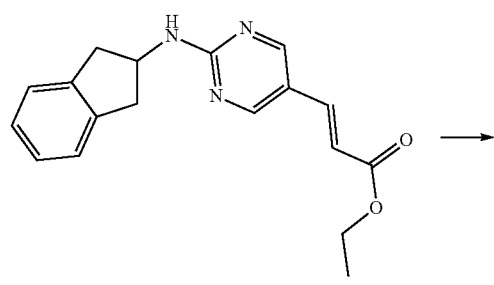
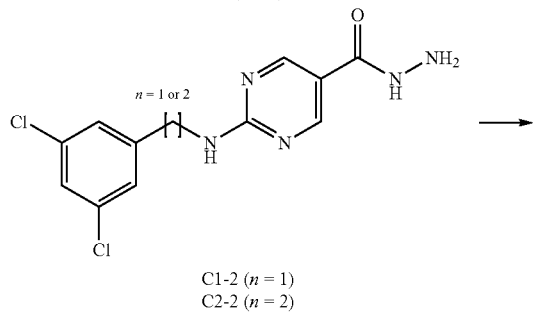

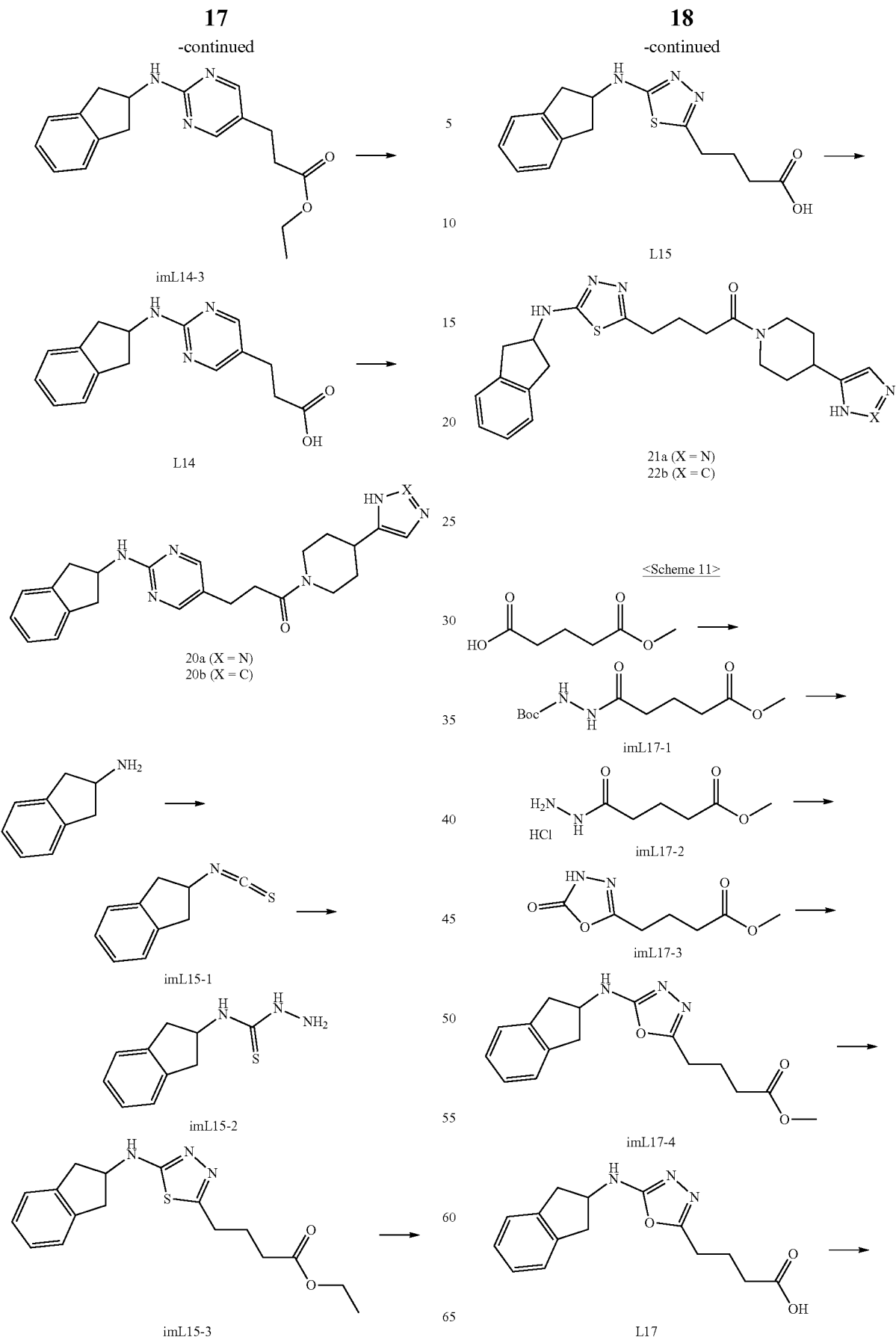

-continued
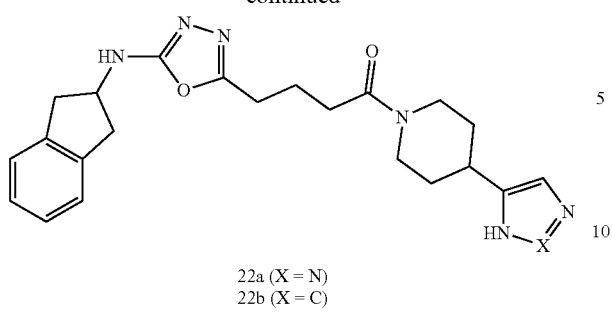
22a (X = N)
22b (X = C)
<Scheme 12>
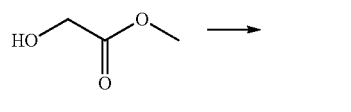
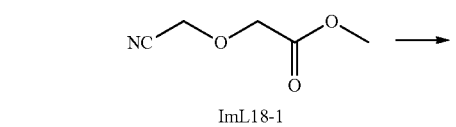
ImL18-1
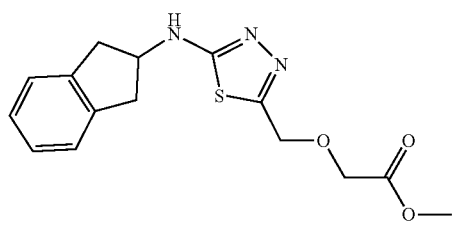
ImL18-2
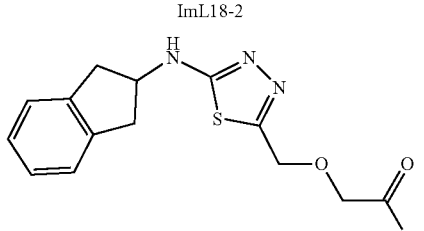
L18
23
<Scheme 13>
2
3-1
<Scheme 14>
im19
<Scheme 15>
im20-1

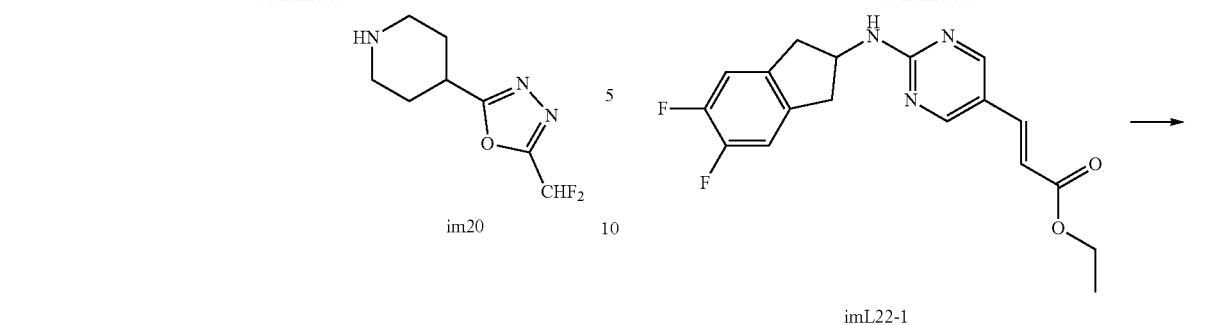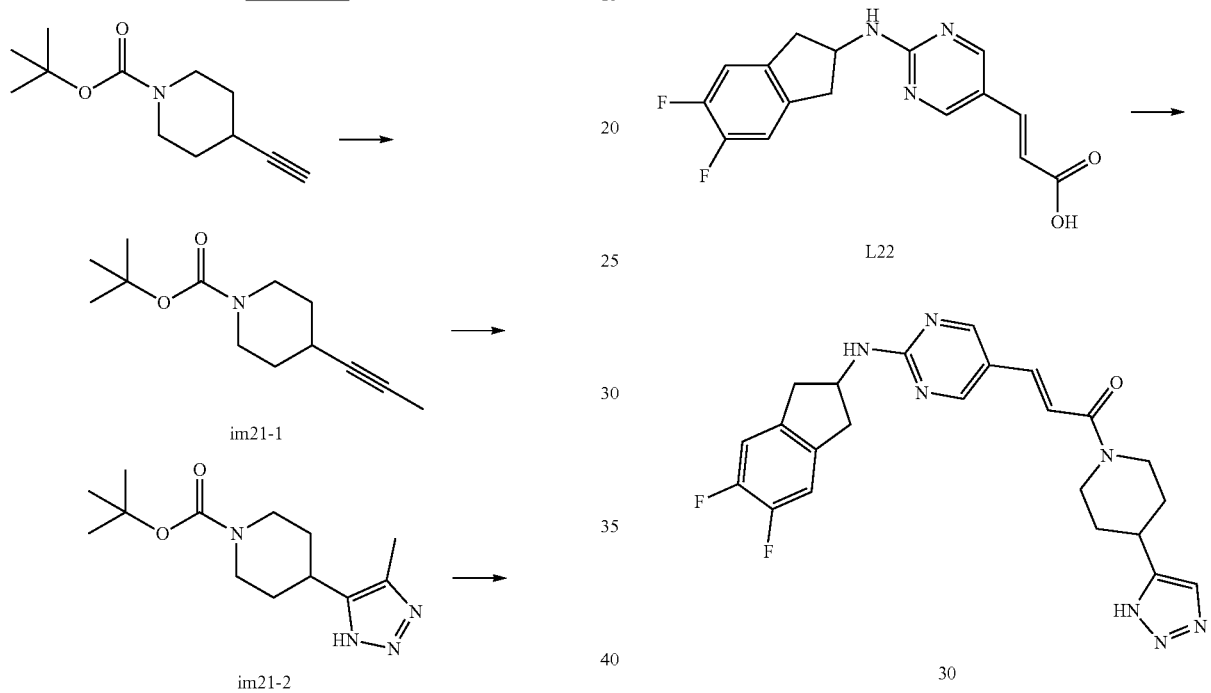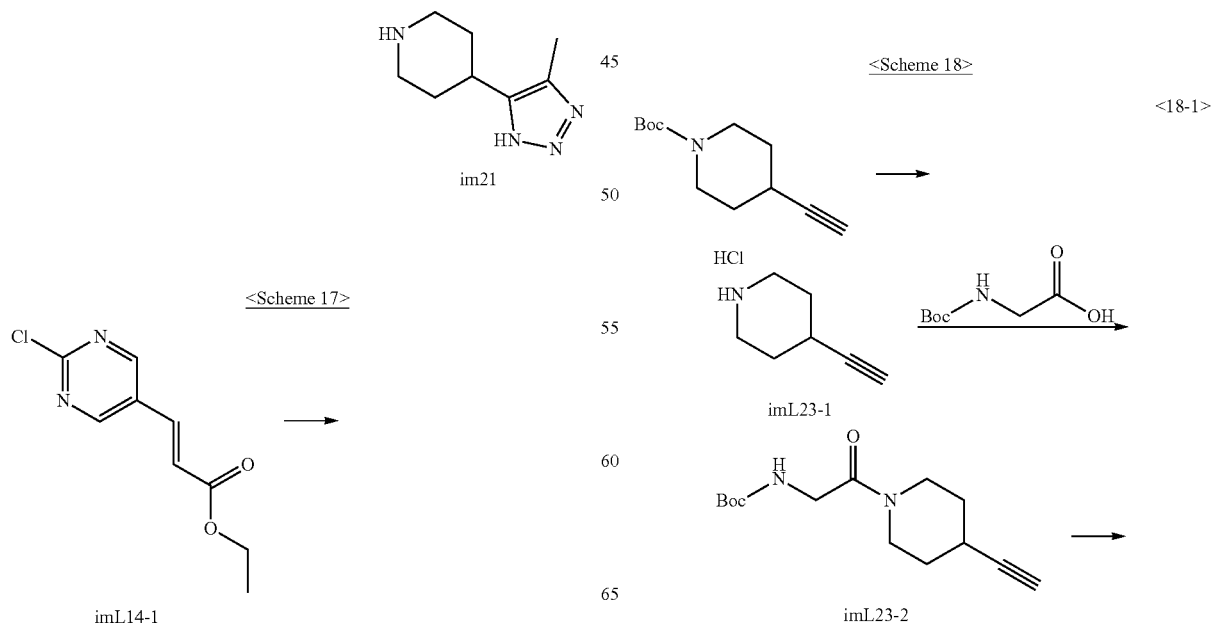

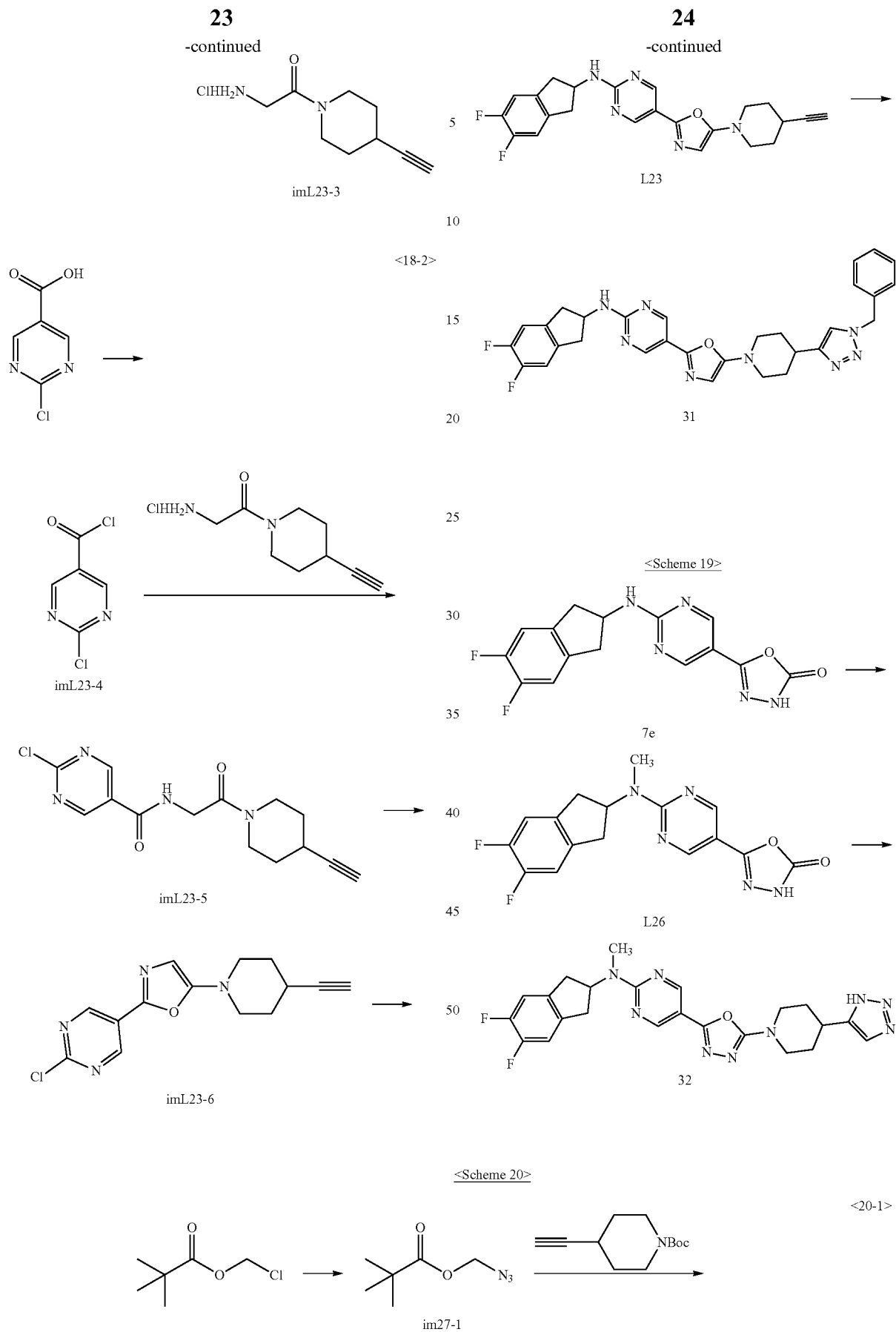

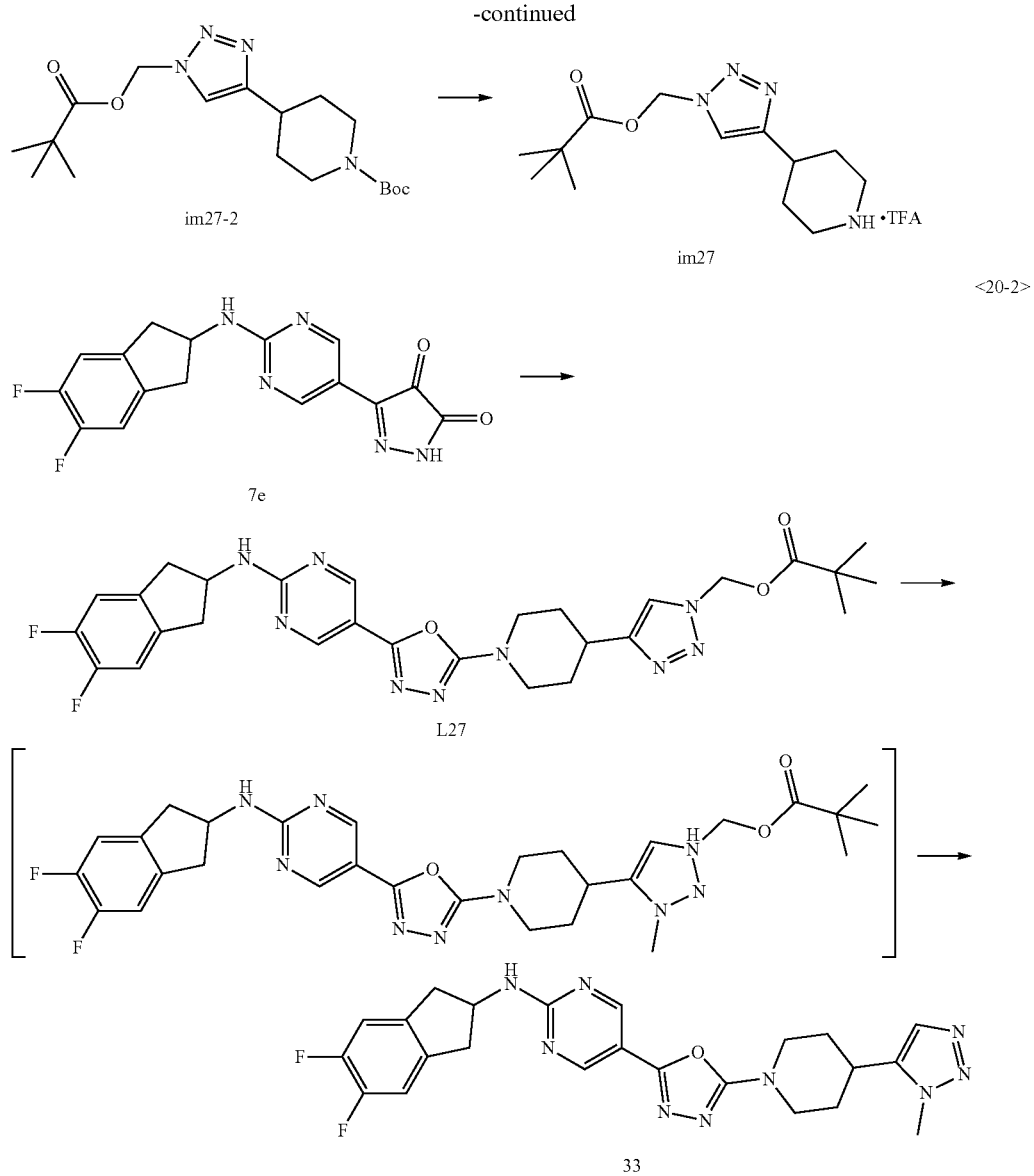
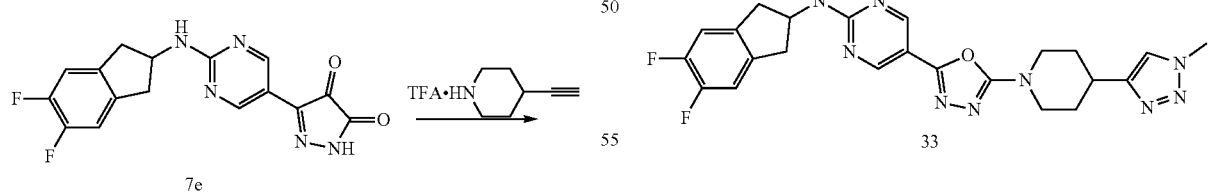
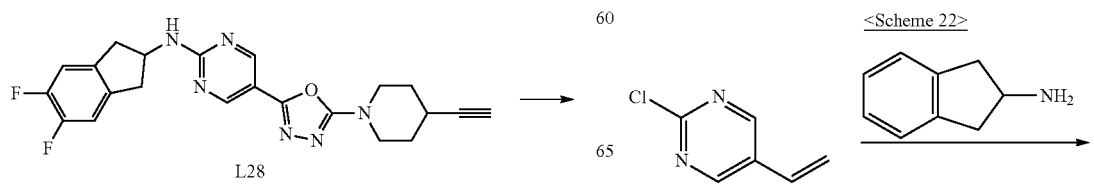

27
-continued
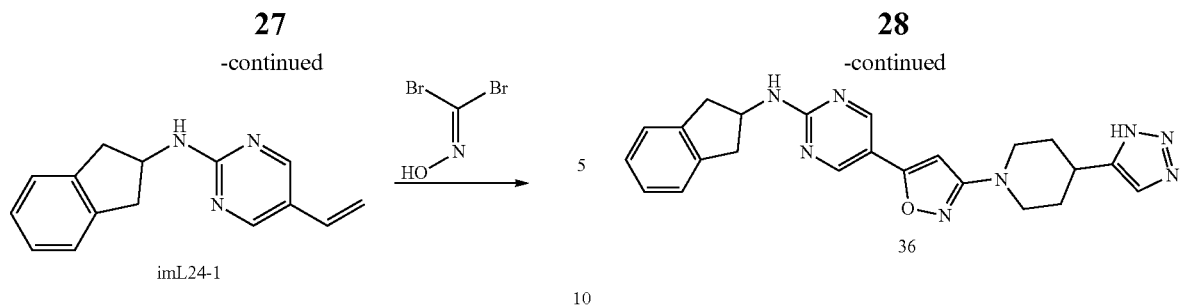
imL24-1
L24
35
28
-continued
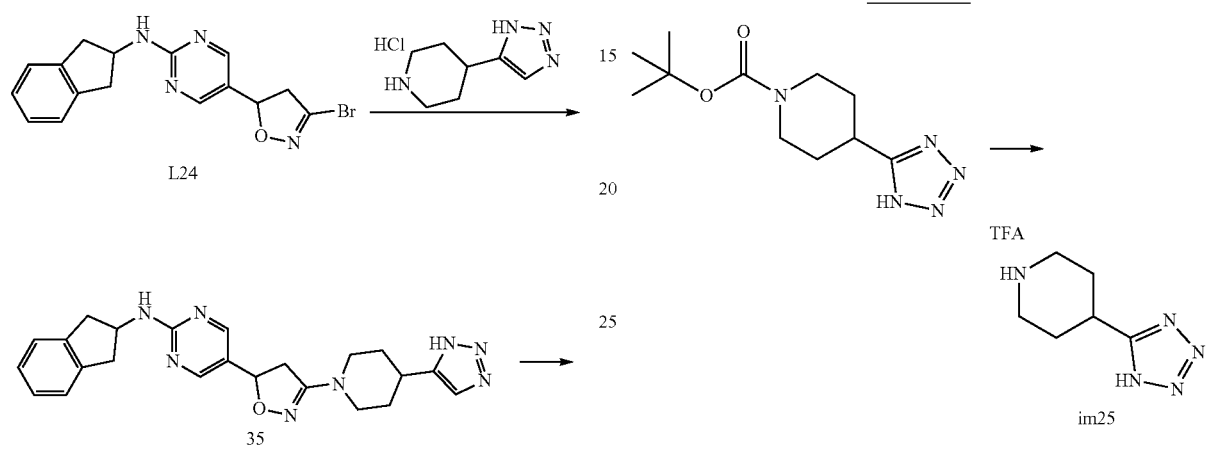
36
<Scheme 23>
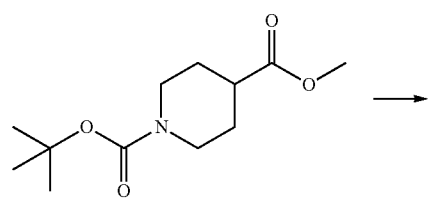
im25
<Scheme 24>
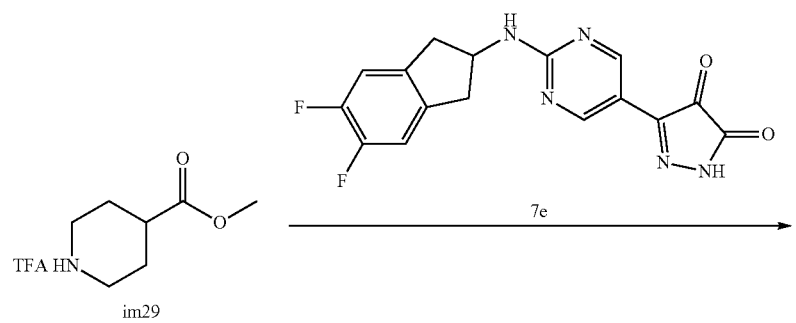
im29  7e
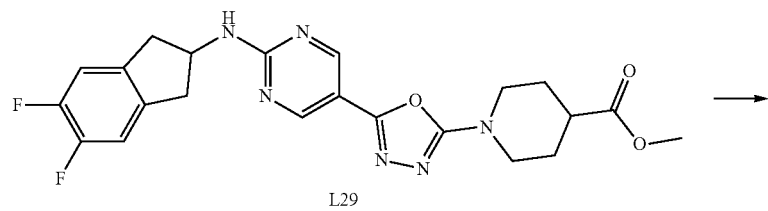
L29

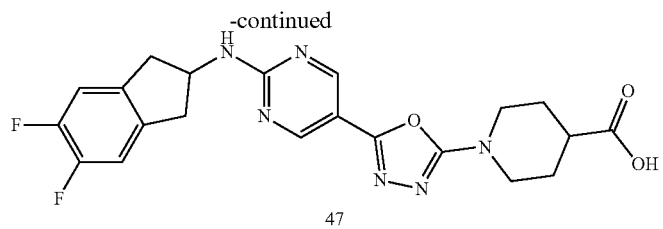
47

<Scheme 25>

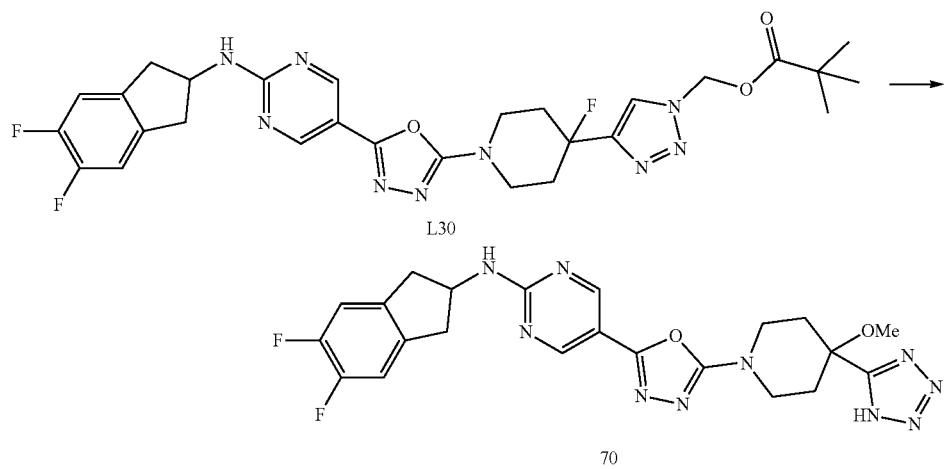

<Scheme 26>

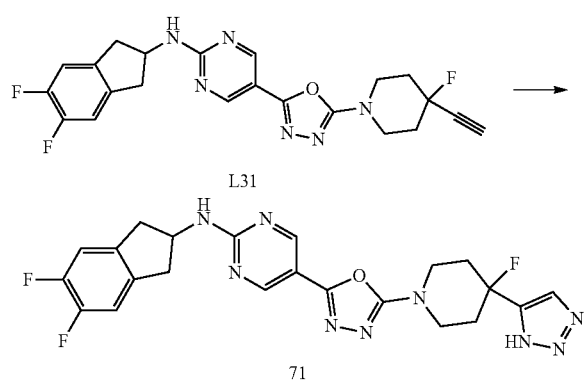

The present invention also provides a pharmaceutical composition for preventing or treating a disease associated with autotaxin activity, comprising the piperidine derivative compound, a hydrate thereof, a solvate thereof or a pharmaceutically acceptable salt thereof as an active ingredient.

The present invention also provides a method for inhibiting autotaxin, and treating or preventing diseases resulting therefrom, comprising administering to a subject in need thereof the piperidine derivative compound, a hydrate thereof, a solvate thereof or a pharmaceutically acceptable salt thereof.

The present invention also provides the piperidine derivative compound, a hydrate thereof, a solvate thereof or a pharmaceutically acceptable salt thereof for use for inhibiting autotaxin, and treating or preventing diseases resulting therefrom.

The inhibitory activity against autotaxin protein, of the piperidine derivative compounds of the present invention was measured, and it was found that they exhibited excellent autotaxin inhibitory activity even at very low concentration of the compounds (nM level), and thus could be used for the treatment and prevention of disease associated with autotaxin activity.

In one embodiment, the disease associated with autotaxin activity may be selected from the group consisting of fibrotic diseases, inflammatory diseases, autoimmune diseases, respiratory diseases, cardiovascular diseases, metabolic diseases, cancer and cancer metastasis, ocular diseases, cholestatic form and other forms of chronic pruritus, and acute or chronic organ transplant rejection.

The fibrotic disease includes, without limitation, idiopathic pulmonary fibrosis (IPF), interstitial lung disease, liver fibrosis, liver cirrhosis, non-alcoholic steatohepatitis, radiation-induced fibrosis, myocardial and vascular fibrosis, renal fibrosis, cutaneous fibrosis, glomerulosclerosis, myocardial fibrosis and vascular fibrosis.

The inflammatory disease includes, without limitation, rheumatoid arthritis, osteoarthritis, atopic dermatitis, inflammatory bowel disease, inflammatory airway disease, chronic obstructive pulmonary disease (COPD) and asthma.

The autoimmune disease includes, without limitation, multiple sclerosis and scleroderma.

The respiratory disease includes, without limitation, asbestos-induced pulmonary fibrosis and acute respiratory distress syndrome (ARDS).

The cardiovascular disease includes, without limitation, arteriosclerosis, myocardial infarction, arterial and pulmonary hypertension, cardiac arrhythmia, stroke and other vascular damage.

The metabolic disease includes, without limitation, obesity and diabetes.

The cancer and cancer metastasis includes, without limitation, breast cancer, ovarian cancer, lung cancer, prostate cancer, mesothelioma, glioma, liver carcinoma, gastrointestinal cancer, pancreatic cancer, and its progression and metastatic invasion.

The ocular disease includes, without limitation, proliferative and non-proliferative (diabetic) retinopathy, dry and wet age-related macular degeneration (AMD), macular edema, central artery/venous occlusion, traumatic injury, and glaucoma.

The present invention also provides a pharmaceutical composition comprising the piperidine derivative compound, a hydrate thereof, a solvate thereof or a pharmaceutically acceptable salt thereof, and a pharmaceutically acceptable additive.

The additive may include a pharmaceutically acceptable carrier or diluent, each of which may be formulated according to conventional methods in the form of oral formulations such as powders, granules, tablets, capsules, suspensions, emulsions, syrups, aerosols; topicals; suppositories; and sterile injectable solutions.

The pharmaceutically acceptable carriers include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate and mineral oil, and the like. They also include diluents or excipients such as fillers, bulking agents, binders, wetting agents, disintegrating agents, and surfactants. Oral solid dosage forms include tablets, pills, powders, granules, capsules, and the like, which may include at least one excipient, such as starch, calcium carbonate, sucrose, lactose, gelatin, and the like, and may include lubricants such as magnesium stearate and talc. Oral liquid preparations may include suspensions, oral solutions, emulsions, syrups, and the like, and may include diluents such as water and liquid paraffin, wetting agents, sweeteners, flavourings, preservatives, and the like. Parenteral preparations include sterilized aqueous solutions, non-aqueous solvents, suspensions, emulsions, creams, lyophilised preparations, and suppositories; non-aqueous solvents and suspensions include propylene glycol, polyethylene glycol, vegetable oils such as olive oil, and injectable esters such as ethylolate. Substrates for suppositories may be witepsol, macrogol, tween 61, cacao gum, laurin gum, glycerogelatin, etc.

The dosage of the active ingredient in the pharmaceutical composition of the present invention depends on the condition and weight of the patient, the extent of the disease, the formulation of the active ingredient, the route and duration of administration, and may be appropriately adjusted depending on the patient. For example, the active ingredient can be administered at a dose of 0.0001 to 1000 mg/kg per day, preferably 0.01 to 100 mg/kg, and the dose may be administered once or in several divided doses per day. Furthermore, the pharmaceutical composition of the present invention may comprise the active ingredient from 0.001 to 90% by weight, based on the total weight of the composition.

The pharmaceutical composition of the present invention may be administered to mammals such as rats, mice, livestock, and humans by various routes, for example, orally, by dermal, intraperitoneally, rectally or intravenously, intramuscular, subcutaneous, intrauterine dura, or intracerebroventricular injection.

Hereinafter, the present disclosure is described in more detail with Preparative Examples, Examples and Test examples. However, the following Preparative Examples, Examples and Test examples are intended to illustrate the present invention, and the scope of the present invention is not limited thereto.

<Preparative Example 1> Synthesis of 4-(1H-1,2,3-Triazol-5-yl)piperidine·HCl (3)

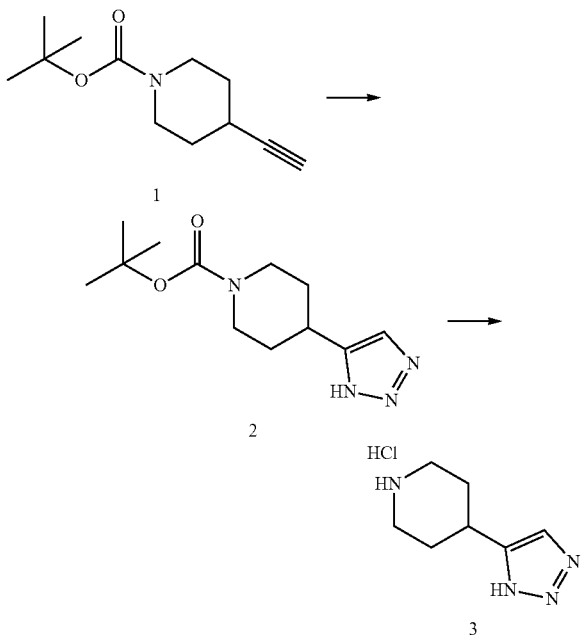

Step 1: Synthesis of tert-Butyl 4-(1H-1,2,3-triazol-5-yl)piperidine-1-carboxylate (2): tert-Butyl 4-ethynylpiperidine-1-carboxylate (1, 1.05 g, 5.00 mmol), trimethylsilyl azide (5.5 mmol) and copper (I) iodide (0.25 mmol) was added to mixture of N,N-dimethylformamide/methanol (9:1, 2 mL) under Ar gas. The reaction mixture was heated at 100° C. for 12 h under Ar gas. The solvent was evaporated to dryness, extracted with ethyl acetate and washed with brine. The organic layer was dried over anhydrous sodium sulfate and concentrated. The product was purified by column chromatography (Dichloromethane/Methanol) to give the subject compound as a white solid (1.03 g, Yield 81.3%).

$^1$H NMR (400 MHz, CDCl$_3$) δ 12.73 (br s, 1H), 7.52 (s, 1H), 4.32-4.01 (m, 2H), 3.00-2.86 (m, 3H), 2.04-1.97 (m, 2H), 1.73-1.60 (m, 2H), 1.48 (s, 9H).

Step 2: Synthesis of 4-(1H-1,2,3-Triazol-5-yl)piperidine·HCl (3): To a solution of tert-butyl 4-(1H-1,2,3-triazol-5-yl)piperidine-1-carboxylate (3.60 mmol) in dioxane (10 mL), which is obtained from the above steps, was added 4.0 M hydrogen chloride solution in dioxane (2 mL). The reaction mixture was stirred at room temperature overnight. The solvent was evaporated to dryness to give the subject compound as a white solid (quantitative).

$^1$H NMR (400 MHz, MeOD) δ 8.37 (s, 1H), 3.56-3.47 (m, 2H), 3.44-3.35 (m, 1H), 3.27-3.18 (m, 2H), 2.37-2.30 (m, 2H), 2.12-1.98 (m, 2H).

<Preparative Example 2> Synthesis of 4-(1H-1,2,4-Triazol-1-yl)piperidine·HCl (Im15-2a) and 4-(3-Methyl-1H-1,2,4-triazol-1-yl)piperidine·HCl (Im15-2b)

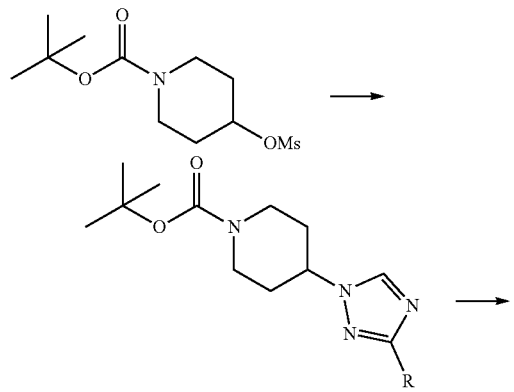

Im15-1a R = H
Im15-1b R = Me

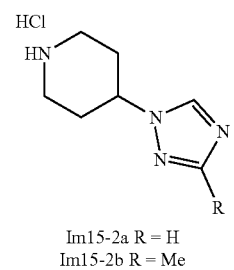

Im15-2a R = H
Im15-2b R = Me

Step 1: Synthesis of tert-Butyl 4-(1H-1,2,4-triazol-1-yl)piperidine-1-carboxylate (Im15-1a) and tert-Butyl 4-(3-methyl-1H-1,2,4-triazol-1-yl)piperidine-1-carboxylate (Im15-1b)

1,2,4-triazole or 3-methyl-1,2,4-triazole (1 mmol) and sodium hydride (1.3 mmol) was dissolved in DMF 5 mL and stirred at 0° C. for 1 h. 4-[(Methylsulfonyl)oxy]piperidine-1-carboxylic acid tert-butyl ester (1.1 mmol) was added to the reaction mixture under Ar gas. The reaction mixture was heated at 90° C. for 5 h. The solvent was evaporated to dryness, extracted with ethyl acetate and washed with brine. The organic layer was dried over anhydrous sodium sulfate and concentrated. The product was purified by column chromatography (EA/Hex) to give the subject compound as a white solid.

tert-Butyl 4-(1H-1,2,4-triazol-1-yl)piperidine-1-carboxylate (Im15-1a) Yield: 43.5%; $^1$H NMR (400 MHz, Chloroform-d) δ 8.10 (s, 1H), 7.95 (s, 1H), 4.34 (tt, J=11.5, 4.1 Hz, 2H), 4.26 (s, 1H), 2.91 (s, 1H), 2.21-2.11 (m, 2H), 1.95 (qd, J=12.2, 4.5 Hz, 2H), 1.48 (s, 9H); MS (ESI, m/z) calculated for $C_{12}H_{21}N_4O_2$ [M+H]$^+$ 253.15, found 253.15.

tert-Butyl 4-(3-methyl-1H-1,2,4-triazol-1-yl)piperidine-1-carboxylate (Im15-1b) Yield: 38.5%; $^1$H NMR (400 MHz, Chloroform-d) δ 7.95 (s, 1H), 7.79 (s, 1H), 4.25 (dd, J=11.5, 4.0 Hz, 2H), 4.13-4.07 (m, 1H), 2.44 (d, J=34.8 Hz, 3H), 2.17-2.06 (m, 3H), 2.00-1.82 (m, 3H), 1.48 (d, J=2.5 Hz, 9H); MS (ESI, m/z) calculated for $C_{13}H_{23}N_4O_2$ [M+H]$^+$ 267.15, found 267.15.

Step 2: Synthesis of 4-(1H-1,2,4-Triazol-1-yl)piperidine·HCl (Im15-2a) and 4-(3-Methyl-1H-1,2,4-triazol-1-yl)piperidine·HCl (Im15-2b)

tert-Butyl 4-(1H-1,2,4-triazol-1-yl)piperidine-1-carboxylate (Im15-1a) or tert-butyl 4-(3-methyl-1H-1,2,4-triazol-1-yl)piperidine-1-carboxylate (Im15-1b) (3.60 mmol), which is obtained from the above steps, was dissolved in 4M HCl in dioxane (5 mL). The reaction mixture was stirred at room temperature overnight. The solvent was evaporated to dryness to give the subject compounds below as a white solid (quantitative).

4-(1H-1,2,4-Triazol-1-yl)piperidine·HCl (Im15-2a) Yield: 97.8%; MS (ESI, m/z) calculated for $C_7H_{13}N_4$ [M+H]+ 153.11, found 153.10.

4-(3-Methyl-1H-1,2,4-triazol-1-yl)piperidine·HCl (Im15-2b). Yield: 95.7%; MS (ESI, m/z) calculated for $C_8H_{15}N_4$ [M+H]+ 167.12, found 167.15.

<Preparative Example 3> Synthesis of 5,6-Difluoro-2,3 dihydro-1H-inden-2-amine (4e)

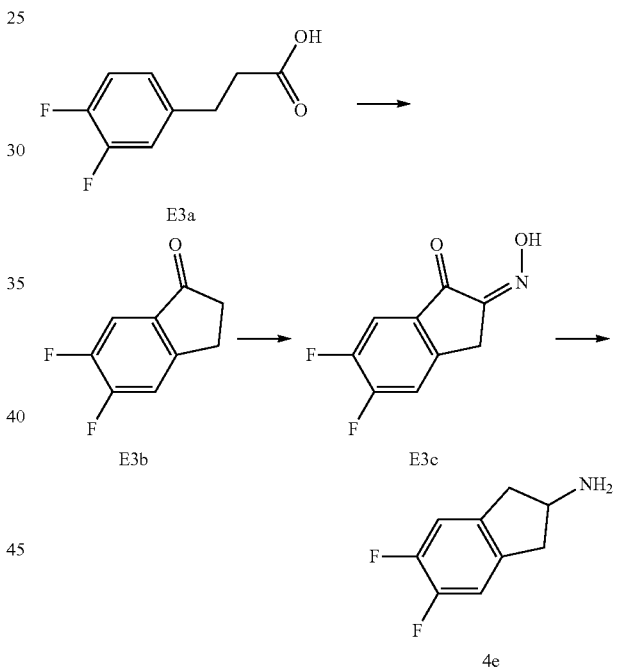

Step 1: Synthesis of 5,6-Difluoro-2,3-dihydro-1H-inden-1-one (E3b)

3,4-Difluorophenyl propionic acid (925.8 mg, 4.97 mmol) was dissolved in DCM (20 mL). Oxalyl chloride (9.94 mmol) and 1 drop of DMF were added to the reaction mixture. The resulting solution was stirred for 3-5 hr. After the completion of the reaction, the solvent was removed under vacuum. Then, 3-(3,4-difluorophenyl)propanoyl chloride was dissolved in DCM and slowly added to $AlCl_3$ (17.4 mmol) in DCM at 0° C. The reaction mixture was stirred at 0° C. for 15 min, refluxed for 4 hr. After cooling to the room temperature, reaction mixture was poured into ice, extracted with DCM (2×30 mL). The organic layer was dried over $MgSO_4$ and filtered. The solvent was concentrated under vacuum and the residue was purified by silica gel column chromatography (EA/Hex) to give the subject compound (Yield: 78.0%).

$^1$H NMR (400 MHz, Chloroform-d) δ 7.53 (dd, J=8.7, 7.5 Hz, 1H), 7.29-7.23 (m, 1H), 3.16-3.08 (m, 2H), 2.79-2.70 (m, 2H).

Step 2: Synthesis of (Z)-5,6-Difluoro-2-(hydroxyimino)-2,3-dihydro-1H-inden-1-one (E3c)

To a solution of 5,6-difluoro-2,3-dihydro-1H-inden-1-one (E3b, 3 mmol) in MeOH at 40° C. was added isoamylnitrite (3.6 mmol) followed by conc. HCl (1 mL). The reaction mixture was stirred at 40° C. for 2-5 hr, cooled to rt and water was added (50 mL). The precipitate was collected by filtration and dried to give the subject compound (Yield: 54.0%).

$^1$H NMR (400 MHz, DMSO-d$_6$) δ 12.77 (s, 1H), 7.82 (dd, J=9.3, 7.7 Hz, 1H), 7.75 (dd, J=10.3, 7.0 Hz, 1H), 3.76 (s, 2H).

Step 3: Synthesis of 5,6-Difluoro-2,3-dihydro-1H-inden-2-amine (4e)

5,6-Difluoro-2-(hydroxyimino)-2,3-dihydro-1H-inden-1-one (E3c, 1 mmol), which is obtained from the above steps, was dissolved in acetic acid (37.5 mL) and sulfuric acid (1.5 mL). 10% Palladium on carbon (10 wt %) was added. The reaction mixture was hydrogenated for overnight. After filtering through a pad of celite, 4N NaOH was added to pH ~12 and extracted with EA (3×100 mL). The organic layer was dried over Na$_2$SO$_4$ and filtered. The solvent was concentrated under vacuum and the residue was purified by amino silica gel column chromatography (DCM/MeOH) to give the subject compound (Yield: 12.1%).

$^1$H NMR (400 MHz, CDCl$_3$) δ 6.98 (t, J=8.9 Hz, 2H), 3.87 (tt, J=6.7, 4.9 Hz, 1H), 3.12 (dd, J=15.8, 6.7 Hz, 2H), 2.62 (dd, J=15.7, 4.9 Hz, 2H), 1.40 (s, 2H); MS (ESI, m/z) calculated for C$_9$H$_{10}$F$_2$N [M+H]$^+$ 170.07, found 170.01.

<Preparative Example 4> Synthesis of 5,6-Dichloro-2,3-dihydro-1H-inden-2-amine (4f)

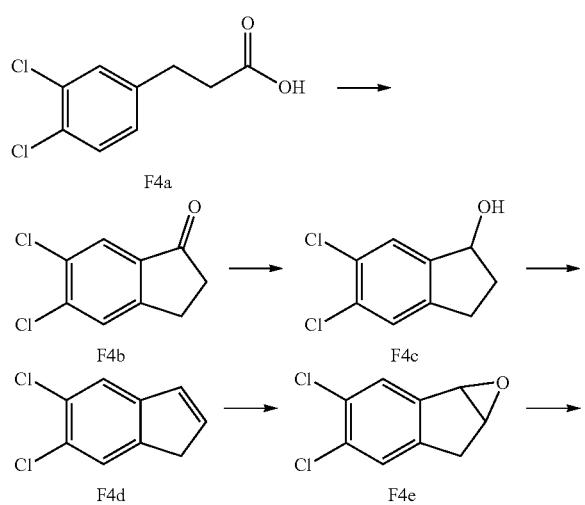

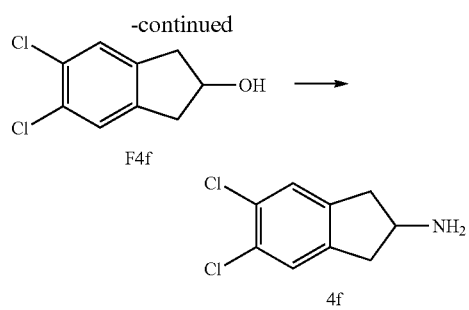

Step 1: Synthesis of 5,6-Dichloro-2,3-dihydro-1H-inden-1-one (F4b)

To a solution of 3-(3,4-dichlorophenyl)propanoic acid (4.56 mmol) in DCM was added catalytic amount of DMF and excess oxalyl chloride was added dropwise under iced bath. The reaction mixture was stirred for 30 min at the room temperature, and then following the removal of solvents. DCM was added to the crude acyl chloride mixture and aluminum chloride (16 mmol) was added to the solution under iced bath. The reaction mixture was refluxed for 1.5 h and was cooled at the room temperature. The crude mixture was quenched with iced water and extracted with ethyl acetate. The combined organic layer was evaporated and purified by silica gel flash chromatography (hexane/ethyl acetate) to give the subject compound (Yield: 75.4%).

$^1$H NMR (400 MHz, Chloroform-d) δ 7.87-7.75 (m, 1H), 7.61 (s, 1H), 3.18-3.06 (m, 2H), 2.76-2.64 (m, 2H).

Step 2: Synthesis of 5,6-Dichloro-2,3-dihydro-1H-inden-1-ol (F4c)

To a solution of 5,6-dichloro-2,3-dihydro-1H-inden-1-one (F4b, 2.16 mmol) in anhydrous EtOH was added sodium borohydride (4.5 mmol) and stirred at room temperature overnight. The crude mixture was poured into DCM, washed with H$_2$O (40 ml), and dried over MgSO$_4$. The crude mixture was purified by silica gel flash chromatography (hexane/ethyl acetate) to give the subject compound (Yield: 88.8%).

$^1$H NMR (400 MHz, Chloroform-d) δ 7.49-7.41 (m, 1H), 7.31 (s, 1H), 5.18 (q, J=6.3 Hz, 1H), 2.99 (ddd, J=16.3, 8.6, 4.5 Hz, 1H), 2.83-2.69 (m, 1H), 2.50 (dddd, J=12.8, 8.2, 6.9, 4.5 Hz, 1H), 2.06 (d, J=6.4 Hz, 1H), 1.95 (dddd, J=13.2, 8.6, 7.0, 5.7 Hz, 1H); $^{13}$C NMR (100 MHz, Chloroform-d) δ 145.26, 143.36, 132.22, 130.68, 126.81, 126.22, 75.72, 36.39, 29.41.

Step 3: Synthesis of 5,6-Dichloro-1H-indene (F4d)

To a solution of 5,6-dichloro-2,3-dihydro-1H-inden-1-ol (F4c, 1.92 mmol) in toluene was added p-toluenesulfonic acid (0.1 eq) and refluxed for 2 h using a Dean-Stark trap. The resulting mixture was cooled at room temperature and the solvent was removed under vacuum. The crude mixture was purified by silica gel flash chromatography (hexane/ethyl acetate) to give the subject compound (Yield: 65.5%).

$^1$H NMR (400 MHz, Chloroform-d) δ 7.55-7.48 (m, 1H), 7.45 (s, 1H), 6.79 (dtd, J=5.5, 1.9, 0.7 Hz, 1H), 6.61 (dt, J=5.5, 2.0 Hz, 1H), 3.38 (td, J=2.0, 0.8 Hz, 2H); $^{13}$C NMR (100 MHz, Chloroform-d) δ 144.96, 143.44, 136.36, 130.95, 130.43, 128.56, 125.64, 122.50, 38.90.

Step 4: Synthesis of 3,4-Dichloro-1a,6a-dihydro-6H-indeno[1,2-b]oxirene (F4e)

To a solution of 5,6-dichloro-1H-indene (F4d, 1.2 mmol) in DCM were added m-CPBA (1.8 mmol) and NaHCO₃ (1.8 mmol) and stirred at room temperature overnight. The reaction mixture was quenched with water and extracted with DCM. The combined organic layer was evaporated and purified by silica gel flash chromatography (hexane/ethyl acetate) to give the subject compound (Yield: 84.9%).

¹H NMR (400 MHz, Chloroform-d) δ 7.56 (s, 1H), 7.31 (s, 1H), 4.25-4.18 (m, 1H), 4.14 (t, J=2.8 Hz, 1H), 3.18 (d, J=18.2 Hz, 1H), 2.99-2.89 (m, 1H); ¹³C NMR (100 MHz, Chloroform-d) δ 143.62, 141.21, 132.60, 130.30, 128.14, 127.15, 58.20, 58.03, 34.26.

Step 5: Synthesis of 5,6-Dichloro-2,3-dihydro-1H-inden-2-ol (F4f)

To a solution of 3,4-dichloro-1a,6a-dihydro-6H-indeno[1,2-b]oxirene (F4e, 0.98 mmol) in THF was slowly added 2.5 M lithium aluminum hydride in THF (1.1 mmol) at 0° C. The reaction mixture was stirred for 30 min at room temperature and quenched with iced water. The solution was extracted with ethyl acetate and purified by silica gel flash chromatography (hexane/ethyl acetate) to give the subject compound (Yield: 86.3%).

¹H NMR (400 MHz, Chloroform-d) δ 7.31 (s, 2H), 4.72 (ddq, J=8.7, 5.8, 3.0 Hz, 1H), 3.22-3.10 (m, 2H), 2.87 (dd, J=16.7, 2.9 Hz, 2H), 1.70 (d, J=5.0 Hz, 1H); ¹³C NMR (100 MHz, Chloroform-d) δ 141.29, 130.54, 126.87, 73.32, 42.30.

Step 6: Synthesis of 5,6-Dichloro-2,3-dihydro-1H-inden-2-amine (4f)

To a solution of 5,6-dichloro-2,3-dihydro-1H-inden-2-ol (F4f, 0.84 mmol) in THF were added phthalimide (1.7 mmol), triphenylphosphine (1.7 mmol), and diisopropyl azodicarboxylate (1.3 mmol) at 0° C. The reaction mixture was stirred for 3 h at room temperature and the solvent was removed under vacuum. Water and EtOH were poured into the crude mixture and hydrazine monohydrate (1.7 mmol) was added into the solution. The reaction mixture was stirred at room temperature overnight. The resulting mixture was poured into DCM (40 ml), washed with H₂O (40 ml), and dried over MgSO₄. The crude mixture was purified by silica gel flash chromatography (dichloromethane/methanol) to give the subject compound (Yield: 20.2%).

¹H NMR (400 MHz, Methanol-d₄) δ 7.36 (s, 2H), 3.87 (s, 1H), 3.21 (dd, J=15.8, 7.1 Hz, 2H), 2.77 (dd, J=16.7, 5.2 Hz, 2H); ¹³C NMR (100 MHz, Methanol-d₄) δ 143.28, 131.29, 127.62, 41.35, 20.36; MS (ESI, m/z) calculated for C₉H₁₀Cl₂N [M+H]⁺ 202.02 found 202.05.

<Preparative Example 5> Synthesis of 2-(Piperidin-4-yl)-5-(trifluoromethyl)-1,3,4-oxadiazole trifluoroacetate salt (im19)

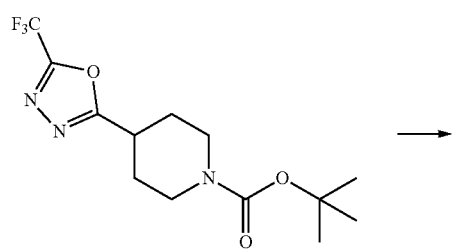

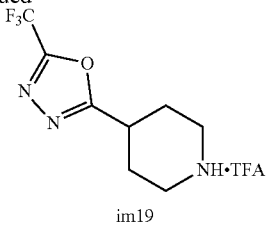

After tert-butyl 4-(5-(difluoromethyl)-1,3,4-oxadiazol-2-yl)piperidine-1-carboxylate (23.5 mg, 0.103 mmol) was dissolved in DCM 2 ml, trifluoroacetic acid 600 uL was added and stirred at room temperature for 1 h (DCM:TFA=3:1). After confirming the completion of the reaction by LCMS and TLC, it was concentrated to remove TFA and dried under vacuum. The compound (im19) was obtained in salt form without purification (17.8 mg, Yield: 54%).

LCMS m/z 222 [M+H]⁺

<Preparative Example 6> Synthesis of 2-(Difluoromethyl)-5-(piperidin-4-yl)-1,3,4-oxadiazole (im20)

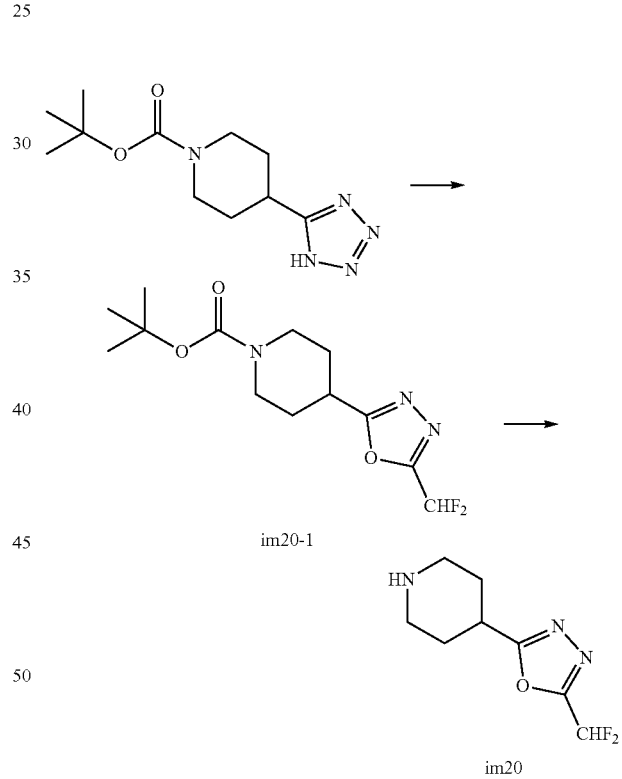

Step 1: Synthesis of tert-Butyl 4-(5-(difluoromethyl)-1,3,4-oxadiazol-2-yl)piperidine-1-carboxylate (im20-1)

After tert-butyl 4-(1H-tetrazol-5-yl)piperidine-1-carboxylate (100 mg, 0.395 mmol) and difluoroacetic anhydride (64 μL, 0.592 mmol) were dissolved in DCM (3.9 mL), the resulting solution was stirred for 1 hour at room temperature. The reaction mixture was quenched with water, extracted with DCM, washed with brine, dried over Na₂SO₄, filtered and concentrated. The product was purified by column chromatography (DCM:MeOH) to give the subject compound (im20-1) as a colorless oil (77 mg, Yield:64.7%).

$^1$H NMR (400 MHz, CDCl$_3$) δ 6.83 (t, J=51.8 Hz, 2H), 4.12 (d, J=7.7 Hz, 2H), 3.19-3.11 (m, 1H), 2.96 (t, J=13.2 Hz, 2H), 2.09 (d, J=12.9 Hz, 3H), 1.84 (ddd, J=24.6, 11.3, 4.1 Hz, 3H), 1.47 (s, 9H).

Step 2: Synthesis of 2-(Difluoromethyl)-5-(piperidin-4-yl)-1,3,4-oxadiazole (im20)

To a solution of im20-1 (76 mg, 0.251 mmol) in DCM (2.5 mL) was added TFA (833 μL) at 0° C. The reaction mixture was stirred for 2 h at room temperature. 1N NaOH was added to pH 8~10, and extracted with DCM. The organic layer was dried over Na$_2$SO$_4$ and filtered. The solvent was concentrated under vacuum. The subject compound (im20) was obtained as a yellow oil and used in the following reaction without purification (32 mg, Yield:63%).

<Preparative Example 7> Synthesis of 4-(4-Methyl-1H-1,2,3-triazol-5-yl)piperidine trifluoroacetate salt (im21)

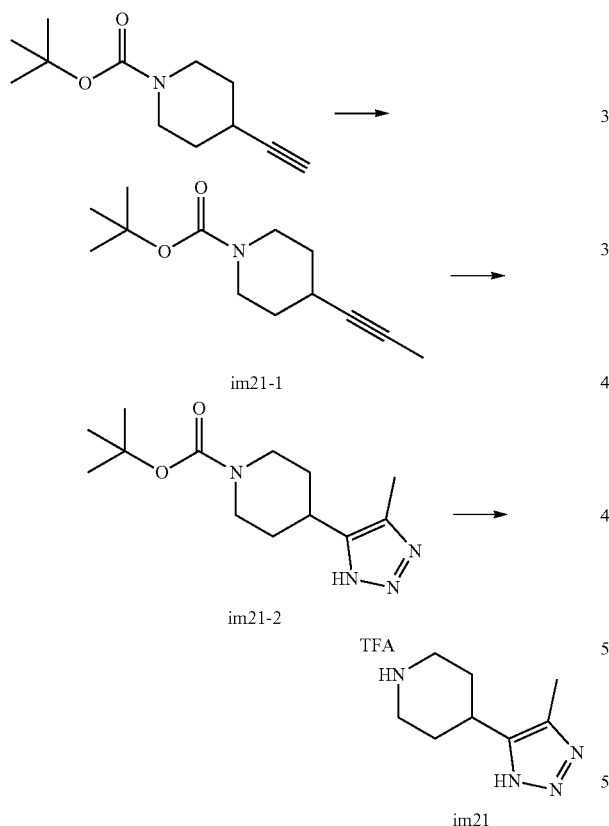

Step 1: Synthesis of tert-Butyl 4-(prop-1-yn-1-yl)piperidine-1-carboxylate (im21-1)

tert-Butyl 4-ethynylpiperidine-1-carboxylate (1.0 g, 4.8 mmol) was dissolved in tetrahydrofuran (14 mL) and maintained at −78° C. under nitrogen atmosphere. 2.5 M n-butyl lithium (1.92 mL, 4.8 mmol) was added and stirred for 30 min. The temperature was raised to room temperature, then iodomethane (450 uL, 7.2 mmol) was added and the reaction was stirred for 12 h. After the reaction, ethyl acetate and H$_2$O were added and extracted, and the organic layer was dried over Na$_2$SO$_4$ and concentrated. The obtained residue was purified by silica gel column chromatography (0-5% MeOH in DCM) to obtain the subject compound (im21-1) as a brown liquid (1.09 g, Yield:100%).

$^1$H NMR (400 MHz, CDCl$_3$) δ 3.69 (d, J=11.7 Hz, 2H), 3.18-3.06 (m, 2H), 2.49 (d, J=2.1 Hz, 1H), 1.79 (d, J=2.3 Hz, 3H), 1.77-1.67 (m, 2H), 1.57-1.48 (m, 2H), 1.45 (s, 9H).

Step 2: Synthesis of tert-Butyl 4-(4-methyl-1H-1,2,3-triazol-5-yl)piperidine-1-carboxylate (im21-2)

im21-1 (170 mg, 0.75 mmol) and trimethylsilylazide (150 uL, 1.16 mmol) were reacted in a microwave reactor at 200° C. for 2 h. The reaction solution was purified by silica gel column chromatography (0-5% MeOH in DCM) to obtain the subject compound (im21-2) as a yellow liquid (30 mg, Yield: 15%).

$^1$H NMR (400 MHz, CDCl$_3$) δ 4.18 (m, 2H), 2.91-2.75 (m, 3H), 2.30 (s, 3H), 1.89-1.66 (m, 4H), 1.46 (s, 9H).

Step 3: Synthesis of 4-(4-Methyl-1H-1,2,3-triazol-5-yl)piperidine trifluoroacetate salt (im21)

tert-Butyl 4-(4-methyl-1H-1,2,3-triazol-5-yl)piperidine-1-carboxylate (30 mg, 0.11 mmol) was dissolved in DCM (1.5 mL), then trifluoroacetic acid (350 uL) was added at 0° C. After raising the temperature to room temperature and reacting for 12 h, the reaction solution was concentrated to give the subject compound (im21), which was used in the following reaction without further purification (Yield: 100%).

LCMS m z 167 [M+H]$^+$

<Preparative Example 8> Synthesis of 4-(1H-Tetrazol-5-yl)piperidine trifluoroacetate salt (im25)

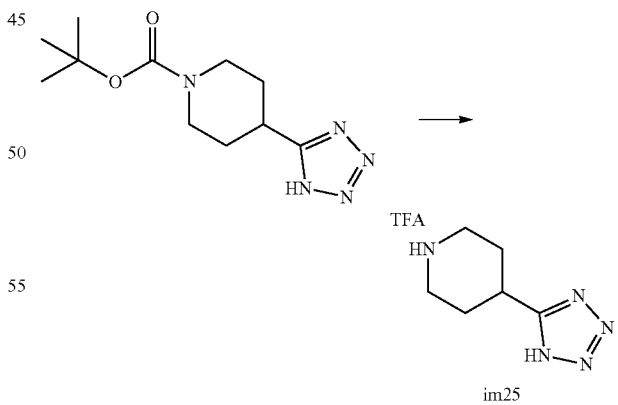

tert-Butyl 4-(1H-tetrazol-5-yl)piperidine-1-carboxylate (0.3 g, 1.1844 mmol) and TFA 3.9 mL was dissolved in DCM 30 mL, and the reaction mixture was stirred at room temperature. After confirming the completion of the reaction by TLC, it was concentrated and used in the following reaction without further purification (Yield: 100%).

[Example 1] Synthesis of 5-(5-(4-(1H-1,2,3-Triazol-5-yl)piperidin-1-yl)-1,3,4-oxadiazol-2-yl)-N-(2,3-dihydro-1H-inden-2-yl)pyrimidin-2-amine (8a)

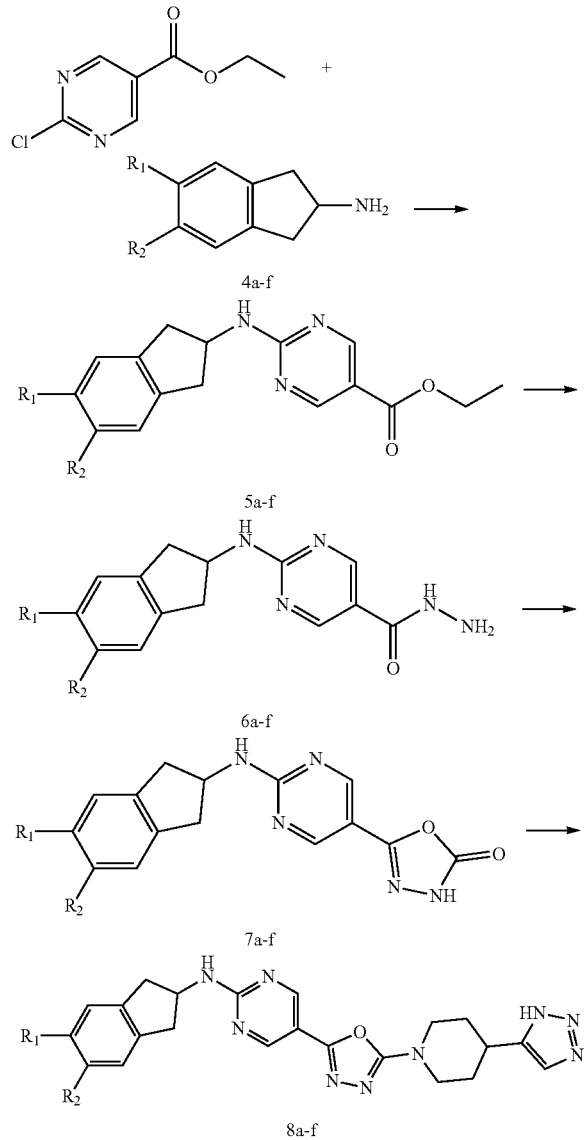

| | R₁ | R₂ |
|---|---|---|
| a | H | H |
| b | F | H |
| c | Cl | H |
| d | Br | H |
| e | F | F |
| f | Cl | Cl |

Step 1: Synthesis of Ethyl 2-((2,3-dihydro-1H-inden-2-yl)amino)pyrimidine-5-carboxylate (5a)

A mixture of 2,3-dihydro-1H-inden-2-amine (4a, 1.68 mmol), ethyl 2-chloropyrimidine-5-carboxylate (1.4 mmol) and triethylamine (3 mmol) in dioxane (5 mL) was stirred at 100° C. for 3 h. After cooling, solvent was evaporated and the crude product was extracted ethyl acetate, and then washed with brine. The organic layer was dried over anhydrous sodium sulfate and concentrated. The product was purified by column chromatography (hexane/ethyl acetate) to give the subject compound as a white solid (Yield: 89.2%).

¹H NMR (400 MHz, CDCl₃) δ 8.90 (s, 1H), 8.75 (s, 1H), 7.25-7.15 (m, 4H), 6.00 (d, J=7.8 Hz, 1H), 4.97-4.79 (m, 1H), 4.35 (q, J=7.1 Hz, 2H), 3.41 (dd, J=16.0, 7.0 Hz, 2H), 2.90 (dd, J=16.0, 4.9 Hz, 2H), 1.37 (t, J=7.1 Hz, 3H); MS (ESI, m/z) calculated for $C_{16}H_{18}N_3O_2[M+H]^+$ 284.14, found 284.05.

Step 2: Synthesis of 2-((2,3-Dihydro-1H-inden-2-yl)amino)pyrimidine-5-carbohydrazide (6a)

Compound 5a (5 mmol) and hydrazine monohydrate (50 mmol) was dissolved in EtOH and refluxed for 6 h. After the reaction was completed, the reaction mixture was evaporated under vacuum to obtain the subject compound (Yield: 93.4%).

¹H NMR (400 MHz, DMSO-d₆) δ 9.59 (s, 1H), 8.72 (s, 1H), 8.68 (s, 1H), 8.08 (d, J=6.9 Hz, 1H), 7.27-7.08 (m, 4H), 4.66 (h, J=7.2 Hz, 1H), 4.42 (s, 2H), 3.26 (dd, J=15.8, 7.6 Hz, 2H), 2.91 (dd, J=15.8, 6.9 Hz, 2H); MS (ESI, m/z) calculated for $C_{14}H_{16}N5O$ $[M+H]^+$ 270.13, found 270.05.

Step 3: Synthesis of 5-(2-((2,3-Dihydro-1H-inden-2-yl)amino)pyrimidine-5-yl)-1,3,4-oxadiazol-2(3H)-one (7a)

A mixture of compound 6a (0.1 mmol), TEA (0.5 mmol) in THF (5 mL) was slowly added to a solution of triphosgene (0.04 mmol) in THF (5 mL) at 0° C. The reaction mixture was stirred for 3 h at room temperature. The solvent was evaporated to dryness. The product was extracted with ethyl acetate and washed with brine. The organic layer was dried over anhydrous sodium sulfate and concentrated. The residue was purified by column chromatography (EA/Hex) to give the subject compound (Yield: 27.4%).

¹H NMR (400 MHz, Chloroform-d) δ 8.75 (s, 1H), 8.67 (s, 1H), 7.26-7.17 (m, 4H), 5.79 (d, J=7.9 Hz, 1H), 4.92-4.83 (m, 1H), 3.42 (dd, J=16.0, 6.9 Hz, 2H), 2.92 (dd, J=16.0, 4.9 Hz, 2H); MS (ESI, m/z) calculated for $C_{15}H_{14}N_5O_2$ $[M+H]^+$ 296.11, found 296.05.

Step 4: Synthesis of 5-(5-(4-(1H-1,2,3-Triazol-5-yl)piperidin-1-yl)-1,3,4-oxadiazol-2-yl)-N-(2,3-dihydro-1H-inden-2-yl)pyrimidin-2-amine (8a)

5-(2-((2,3-dihydro-1H-inden-2-yl)amino)pyrimidine-5-yl)-1,3,4-oxadiazol-2(3H)-one (7a, 1 mmol), 4-(1H-1,2,3-triazol-5-yl)piperidine·HCl (3, 1.2 mmol) prepared from Preparative Example 1, DIEA (3 mmol) and BOP reagent (1.2 mmol) were dissolved in DMF (5 mL). The reaction mixture was stirred at room temperature overnight. The solvent was evaporated to dryness. The crude product was extracted with ethyl acetate and washed with brine. The organic layer was dried over anhydrous sodium sulfate and concentrated. The product was separated by column chromatography (DCM/MeOH) to give the subject compound as a white solid (Yield: 46.1%).

¹H NMR (400 MHz, CDCl₃) δ 12.55 (s, 1H), 8.79 (s, 2H), 7.54 (s, 1H), 7.26-7.22 (m, 2H), 7.21-7.16 (m, 2H), 5.88 (d, J=7.7 Hz, 1H), 4.93-4.83 (m, 1H), 4.21-4.09 (m, 2H), 3.42 (dd, J=16.0, 7.0 Hz, 2H), 3.33-3.22 (m, 2H), 3.11-3.02 (m, 1H), 2.92 (dd, J=16.0, 5.0 Hz, 2H), 2.21-2.11 (m, 2H), 1.97-1.83 (m, 2H); HRMS (ESI, m/z) calculated for $C_{22}H_{24}N_9O$ $[M+H]^+$ 430.2098, found 430.2103.

[Example 2] Synthesis of 5-(5-(4-(1H-1,2,3-Triazol-5-yl)piperidin-1-yl)-1,3,4-oxadiazol-2-yl)-N-(5-fluoro-2,3-dihydro-1H-inden-2-yl)pyrimidin-2-amine (8b)

The subject compound was synthesized according to the same procedure as in Example 1, except for the use of 5-fluoro-2,3-dihydro-1H-inden-2-amine (4b) instead of 2,3-dihydro-1H-inden-2-amine (4a) (Yield: 83.0%).
$^1$H NMR (400 MHz, Chloroform-d) δ 12.69 (s, 1H), 8.79 (s, 2H), 7.54 (s, 1H), 7.16 (dd, J=8.3, 5.2 Hz, 1H), 7.01-6.79 (m, 2H), 5.97 (d, J=7.6 Hz, 1H), 4.96-4.82 (m, 1H), 4.21-4.09 (m, 2H), 3.38 (td, J=15.1, 14.7, 7.0 Hz, 2H), 3.28 (ddd, J=13.1, 11.7, 2.9 Hz, 2H), 3.07 (tt, J=11.5, 3.7 Hz, 1H), 2.88 (td, J=16.0, 5.2 Hz, 2H), 2.16 (dd, J=13.6, 3.5 Hz, 2H), 1.97-1.82 (m, 2H); HRMS (ESI, m/z) calculated for $C_{22}H_{23}FN_9O$ [M+H]$^+$ 448.2004, found 448.2003.

[Example 3] Synthesis of 5-(5-(4-(1H-1,2,3-Triazol-5-yl)piperidin-1-yl)-1,3,4-oxadiazol-2-yl)-N-(5-chloro-2,3-dihydro-1H-inden-2-yl)pyrimidin-2-amine (8c)

The subject compound was synthesized according to the same procedure as in Example 1, except for the use of 5-chloro-2,3-dihydro-1H-inden-2-amine (4c) instead of 2,3-dihydro-1H-inden-2-amine (4a) (Yield: 62.5%).
$^1$H NMR (400 MHz, Chloroform-d) δ 12.37 (s, 1H), 8.79 (s, 2H), 7.54 (s, 1H), 7.22 (q, J=1.2 Hz, 1H), 7.16 (d, J=1.3 Hz, 2H), 5.84 (d, J=7.6 Hz, 1H), 4.88 (qt, J=7.2, 5.1 Hz, 1H), 4.15 (dt, J=13.3, 4.0 Hz, 2H), 3.45-3.33 (m, 2H), 3.27 (ddd, J=13.2, 11.9, 2.9 Hz, 2H), 3.07 (tt, J=11.4, 3.7 Hz, 1H), 2.95-2.83 (m, 2H), 2.21-2.11 (m, 2H), 1.96-1.80 (m, 2H); MS (ESI, m/z) calculated for $C_{22}H_{23}ClN_9O$ [M+H]$^+$ 464.1709, found 464.1709.

[Example 4] Synthesis of 5-(5-(4-(1H-1,2,3-Triazol-5-yl)piperidin-1-yl)-1,3,4-oxadiazol-2-yl)-N-(5-bromo-2,3-dihydro-1H-inden-2-yl)pyrimidin-2-amine (8d)

The subject compound was synthesized according to the same procedure as in Example 1, except for the use of 5-bromo-2,3-dihydro-1H-inden-2-amine (4d) instead of 2,3-dihydro-1H-inden-2-amine (4a) (Yield: 38.0%).
$^1$H NMR (400 MHz, CDCl$_3$) δ 8.79 (s, 2H), 7.55 (s, 1H), 7.38 (s, 1H), 7.31 (dd, J=8.0, 1.9 Hz, 1H), 7.11 (d, J=8.0 Hz, 1H), 5.70 (d, J=7.6 Hz, 1H), 4.95-4.79 (m, 1H), 4.20-4.10 (m, 2H), 3.45-3.21 (m, 4H), 3.06 (tt, J=11.5, 3.8 Hz, 1H), 2.88 (ddd, J=20.9, 16.2, 5.1 Hz, 2H), 2.21-2.10 (m, 2H), 1.98-1.81 (m, 2H); MS (ESI, m/z) calculated for $C_{22}H_{23}BrN_9O$ [M+H]$^+$ 508.1203, found 508.1202.

[Example 5] Synthesis of 5-(5-(4-(1H-1,2,3-Triazol-5-yl)piperidin-1-yl)-1,3,4-oxadiazol-2-yl)-N-(5,6-difluoro-2,3-dihydro-1H-inden-2-yl)pyrimidin-2-amine (8e)

The subject compound was synthesized according to the same procedure as in Example 1, except for the use of 5,6-difluoro-2,3-dihydro-1H-inden-2-amine (4e) instead of 2,3-dihydro-1H-inden-2-amine (4a) (Yield: 63.8%).
$^1$H NMR (400 MHz, Chloroform-d) δ 13.08 (s, 1H), 8.79 (s, 2H), 7.54 (s, 1H), 7.02 (t, J=8.8 Hz, 2H), 6.03 (d, J=7.6 Hz, 1H), 4.89 (qt, J=7.2, 5.2 Hz, 1H), 4.14 (dt, J=13.4, 3.8 Hz, 2H), 3.42-3.19 (m, 4H), 3.07 (tt, J=11.4, 3.7 Hz, 1H), 2.97-2.82 (m, 2H), 2.16 (dd, J=13.7, 3.7 Hz, 2H), 1.99-1.82 (m, 2H); HRMS (ESI, m/z) calculated for $C_{22}H_{22}F_2N_9O$ [M+H]$^+$ 466.1910, found 466.1913.

[Example 6] Synthesis of 5-(5-(4-(1H-1,2,3-Triazol-5-yl)piperidin-1-yl)-1,3,4-oxadiazol-2-yl)-N-(5,6-dichloro-2,3-dihydro-1H-inden-2-yl)pyrimidin-2-amine (8f)

The subject compound was synthesized according to the same procedure as in Example 1, except for the use of 5,6-dichloro-2,3-dihydro-1H-inden-2-amine (4f) instead of 2,3-dihydro-1H-inden-2-amine (4a) (Yield: 54.3%).
$^1$H NMR (400 MHz, Chloroform-d) δ 12.17 (s, 1H), 8.80 (s, 2H), 7.54 (s, 1H), 7.32 (s, 2H), 5.79 (d, J=7.5 Hz, 1H), 4.88 (qt, J=7.2, 5.2 Hz, 1H), 4.15 (dt, J=12.6, 3.8 Hz, 2H), 3.38 (dd, J=16.0, 7.3 Hz, 2H), 3.28 (td, J=13.2, 2.9 Hz, 2H), 3.06 (ddt, J=11.4, 7.4, 3.7 Hz, 1H), 2.88 (dd, J=16.3, 5.2 Hz, 2H), 2.22-2.12 (m, 2H), 1.98-1.82 (m, 2H); MS (ESI, m/z) calculated for $C_{22}H_{22}Cl_2N_9O$ [M+H]$^+$ 498.13, found 498.15.

[Example 7] Synthesis of N-(5-(5-(4-(1H-1,2,3-triazol-5-yl)piperidin-1-yl)-1,3,4-oxadiazol-2-yl)pyrimidin-2-yl)-6,7-dihydro-5H-cyclopenta[b]pyrazin-6-amine (13)

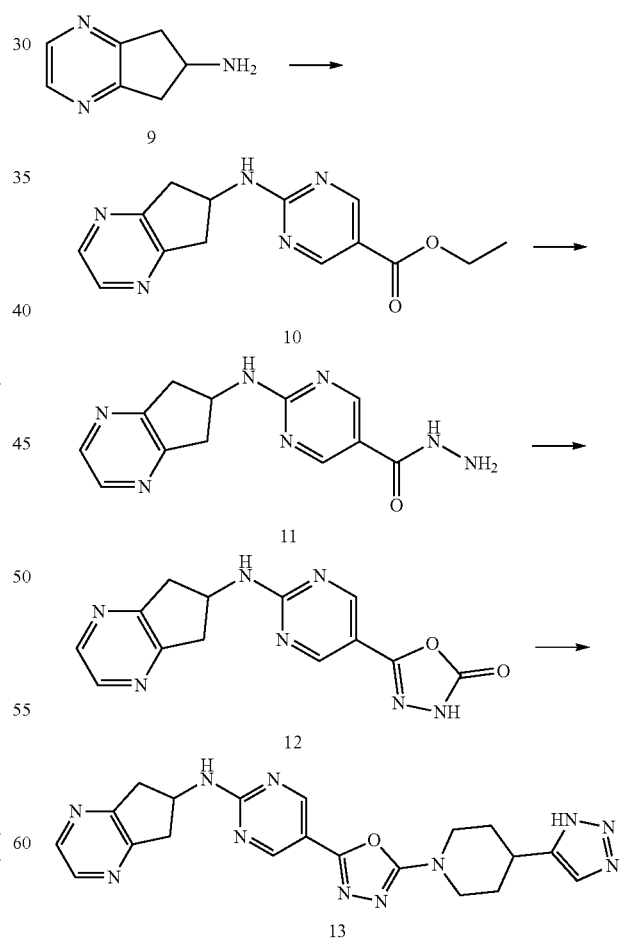

The subject compound was synthesized according to the same procedure as in Example 1, except for the use of 6,7-dihydro-5H-cyclopenta[b]pyrazin-6-amine (9) instead of 2,3-dihydro-1H-inden-2-amine (4a) (Yield: 53.0%).

$^1$H NMR (400 MHz, Methanol-$d_4$) δ 8.79 (s, 2H), 8.34 (s, 2H), 7.75-7.62 (m, 1H), 4.94 (tt, J=7.8, 5.7 Hz, 1H), 4.11 (dt, J=13.3, 3.7 Hz, 2H), 3.54 (dd, J=17.5, 7.9 Hz, 2H), 3.35 (s, 2H), 3.19-3.04 (m, 3H), 2.19-2.08 (m, 2H), 1.86 (qd, J=12.2, 4.3 Hz, 2H); MS (ESI, m/z) calculated for $C_{20}H_{22}N_{11}O$ [M+H]$^+$ 432.20, found 432.20.

[Example 8] Synthesis of 6-(5-(4-(1H-1,2,3-Triazol-5-yl)piperidin-1-yl)-1,3,4-oxadiazol-2-yl)-N-(2,3-dihydro-1H-inden-2-yl)pyridazin-3-amine (14)

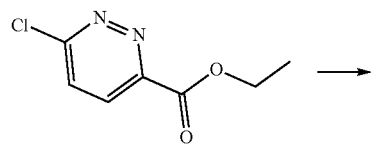

imM67-1

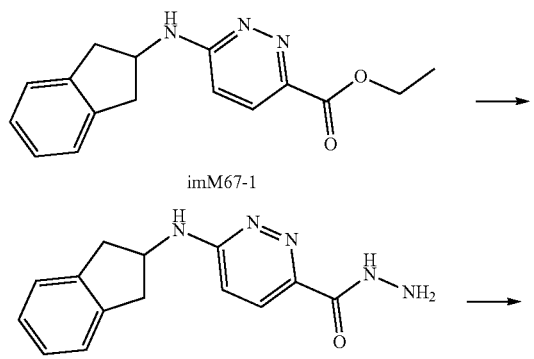

imM67-2 imM67-3

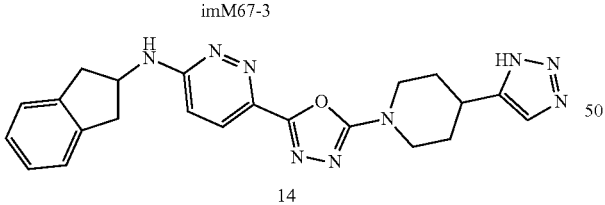

14

The subject compound was synthesized according to the same procedure as in Example 1, except for the use of ethyl 6-chloropyridazin-3-carboxylate instead of ethyl 2-chloropyrimidine-5-carboxylate (Yield: 42.0%).

$^1$H NMR (400 MHz, DMSO-$d_6$) δ 14.78 (s, 1H), 7.80 (d, J=9.4 Hz, 1H), 7.76 (d, J=6.4 Hz, 1H), 7.72 (s, 1H), 7.30-7.24 (m, 2H), 7.19-7.15 (m, 2H), 6.94 (d, J=9.4 Hz, 1H), 4.77 (h, J=6.7, 6.1 Hz, 1H), 4.04-3.96 (m, 2H), 3.30 (d, J=2.5 Hz, 4H), 3.08-2.99 (m, 1H), 2.90 (dd, J=16.0, 5.4 Hz, 2H), 2.09-2.02 (m, 2H), 1.80-1.67 (m, 2H). HRMS (ESI) m/z (M+H)$^+$ calcd for $C_{22}H_{24}N_9O$=430.21; found 430.2107.

[Example 9] Synthesis of 5-(5-(4-(1H-1,2,4-Triazol-1-yl)piperidin-1-yl)-1,3,4-oxadiazol-2-yl)-N-(2,3-dihydro-1H-inden-2-yl)pyrimidin-2-amine (15a)

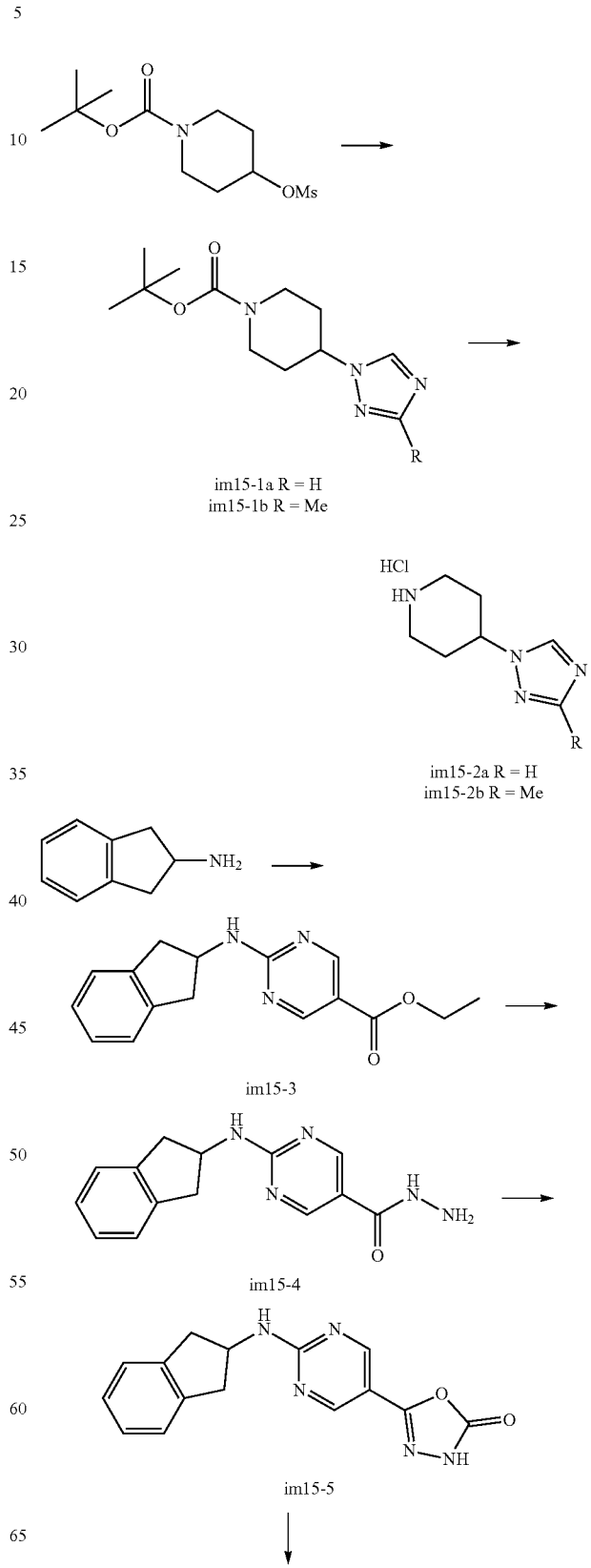

-continued

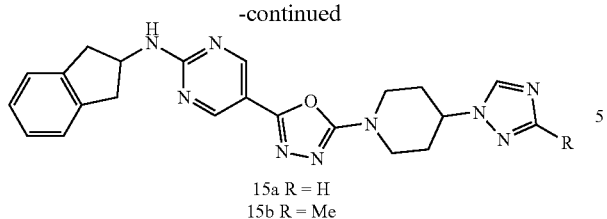

15a R = H
15b R = Me

The subject compound was synthesized according to the same procedure as in Example 1, except for the use of 4-(1H-1,2,4-triazol-1-yl)piperidine·HCl (Im15-2a) obtained from Preparative Example 2 instead of 4-(1H-1,2,3-triazol-5-yl)piperidine·HCl (3) (Yield: 65.2%).

$^1$H NMR (400 MHz, CDCl$_3$) δ 8.76 (s, 2H), 8.14 (s, 1H), 7.97 (s, 1H), 7.28-7.20 (m, 2H), 7.21-7.14 (m, 2H), 6.02 (d, J=7.7 Hz, 1H), 4.87 (qt, J=7.2, 5.0 Hz, 1H), 4.47 (tt, J=11.1, 4.1 Hz, 1H), 4.29-4.17 (m, 2H), 3.52-3.35 (m, 3H), 3.30 (ddd, J=13.4, 11.7, 3.0 Hz, 2H), 2.91 (dd, J=16.0, 5.0 Hz, 2H), 2.37-2.27 (m, 2H), 2.27-2.13 (m, 2H); HRMS (ESI, m/z) calculated for C$_{22}$H$_{24}$N$_9$O [M+H]$^+$ 430.2098, found 430.2098.

[Example 10] Synthesis of N-(2,3-dihydro-1H-inden-2-yl)-5-(5-(4-(3-methyl-1H-1,2,4-triazol-1-yl)piperidin-1-yl)-1,3,4-oxadiazol-2-yl)pyrimidin-2-amine (15b)

The subject compound was synthesized according to the same procedure as in Example 1, except for the use of 4-(3-methyl-1H-1,2,4-triazol-1-yl)piperidine·HCl (Im15-2b) obtained from Preparative Example 2 instead of 4-(1H-1,2,3-triazol-5-yl)piperidine·HCl (3) (Yield: 57.4%).

$^1$H NMR (400 MHz, Chloroform-d) δ 8.77 (s, 2H), 7.90 (d, J=77.3 Hz, 1H), 7.28-7.20 (m, 3H), 7.23-7.15 (m, 2H), 5.82 (d, J=7.7 Hz, 1H), 4.88 (dtd, J=12.3, 7.3, 5.0 Hz, 1H), 4.42-4.16 (m, 3H), 3.42 (dd, J=16.0, 7.0 Hz, 2H), 3.34-3.22 (m, 2H), 2.91 (dd, J=16.0, 5.0 Hz, 2H), 2.46 (d, J=45.0 Hz, 3H), 2.38-2.24 (m, 2H), 2.26-2.13 (m, 1H), 2.09-1.99 (m, 1H); HRMS (ESI, m/z) calculated for C$_{23}$H$_{26}$N$_9$O [M+H]$^+$ 444.2255, found 444.2255.

[Example 11] Synthesis of N-(5-bromo-2,3-dihydro-1H-inden-2-yl)-5-(5-(2-methyl-4-(1H-1,2,3-triazol-5-yl)piperidin-1-yl)-1,3,4-oxadiazol-2-yl)pyrimidin-2-amine (16)

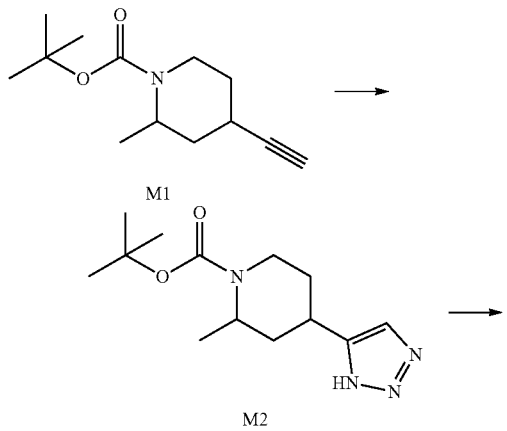

-continued

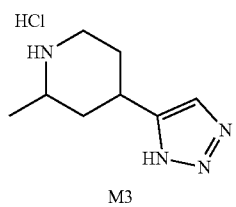

M3

Step 1-1: Synthesis of tert-Butyl 2-methyl-4-(1H-1,2,3-triazol-5-yl)piperidine-1-carboxylate (M2)

The subject compound was synthesized according to the same procedure as in Step 1 of Preparative Example 1, except for the use of tert-butyl 4-ethynyl-2-methylpiperidine-1-carboxylate instead of tert-butyl 4-ethynylpiperidine-1-carboxylate (Yield: 47.0%).

$^1$H NMR (400 MHz, Methanol-d$_4$) δ 7.64 (s, 1H), 4.51 (t, J=6.4 Hz, 1H), 4.04 (ddd, J=13.8, 4.6, 2.3 Hz, 1H), 3.28-3.16 (m, 1H), 3.06 (s, 1H), 2.03-1.85 (m, 2H), 1.79 (dt, J=13.0, 6.5 Hz, 1H), 1.62-1.49 (m, 1H), 1.47 (s, 9H), 1.26 (d, J=7.0 Hz, 3H); MS (ESI, m/z) calculated for C$_{13}$H$_{23}$N$_4$O$_2$ [M+H]$^+$ 267.18, found 267.20.

Step 1-2: Synthesis of 2-Methyl-4-(1H-1,2,3-triazol-5-yl)piperidine·HCl (M3)

The subject compound was synthesized according to the same procedure as in Step 2 of Preparative Example 1 using M2 obtained from the above steps (quantitative).

MS (ESI, m/z) calculated for C8H14N4 [M+H]+ 166.12, found 166.10.

Step 2: Synthesis of N-(5-bromo-2,3-dihydro-1H-inden-2-yl)-5-(5-(2-methyl-4-(1H-1,2,3-triazol-5-yl)piperidin-1-yl)-1,3,4-oxadiazol-2-yl)pyrimidin-2-amine (16)

The subject compound was synthesized according to the same procedure as in Example 4, except for the use of 2-methyl-4-(1H-1,2,3-triazol-5-yl)piperidine·HCl (M3) obtained from the above steps instead of 4-(1H-1,2,3-triazol-5-yl)piperidine·HCl (3) (Yield: 11.2%).

$^1$H NMR (400 MHz, Methanol-d$_4$) δ 8.77 (s, 2H), 7.67 (s, 1H), 7.39 (s, 1H), 7.33-7.26 (m, 1H), 7.14 (d, J=8.0 Hz, 1H), 5.36-5.32 (m, 1H), 4.58 (s, 1H), 4.50 (dd, J=7.1, 3.3 Hz, 1H), 4.05-3.95 (m, 1H), 2.93 (ddd, J=21.7, 16.1, 6.3 Hz, 2H), 2.14 (d, J=12.4 Hz, 1H), 2.04-2.02 (m, 2H), 1.80 (qd, J=13.0, 4.7

Hz, 1H), 1.62-1.56 (m, 2H), 1.42 (d, J=6.9 Hz, 3H); MS (ESI, m/z) calculated for $C_{23}H_{25}BrN_9O$ [M+H]$^+$ 522.13, found 522.15.

[Example 12] Synthesis of 5-(5-(4-(1H-1,2,3-Triazol-5-yl)piperidin-1-yl)-1,3,4-oxadiazol-2-yl)-N-(5-bromo-2,3-dihydro-1H-inden-2-yl)pyridin-2-amine (17a)

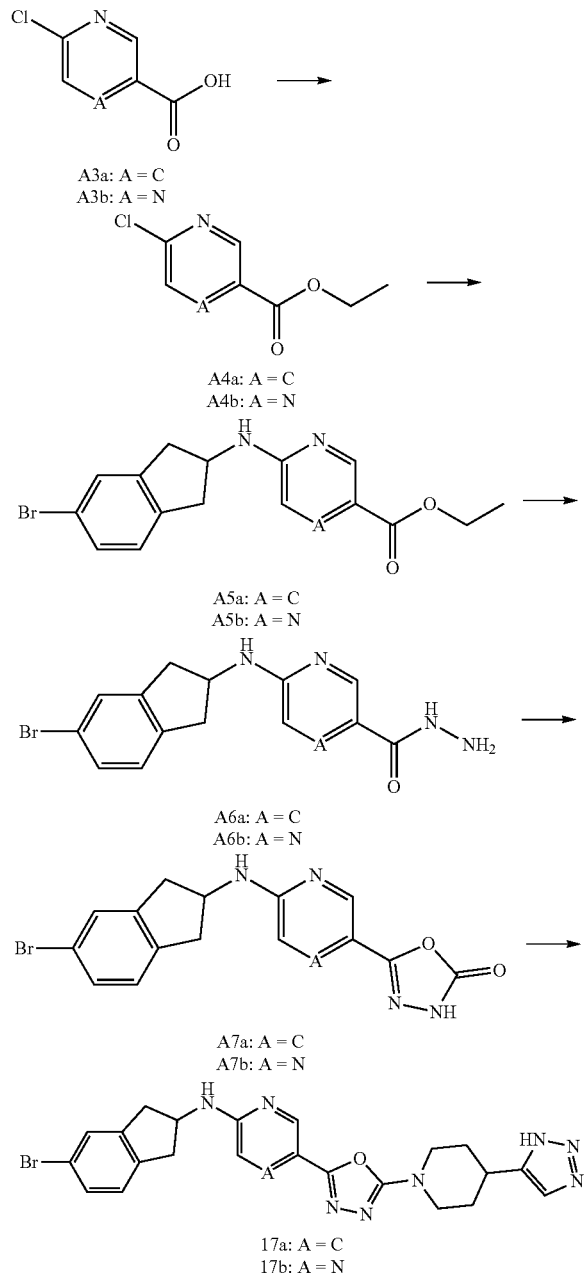

A3a: A = C
A3b: A = N

A4a: A = C
A4b: A = N

A5a: A = C
A5b: A = N

A6a: A = C
A6b: A = N

A7a: A = C
A7b: A = N

17a: A = C
17b: A = N

Step 1: Synthesis of Ethyl 6-chloronicotinate (A4a)

6-chloronicotinic acid (3.2 mmol) and 1,1'-carbonyldiimidazole (3.5 mmol) were added into THF under Ar gas at room temperature. The reaction mixture was stirred for 3 h at the same temperature. To the mixture was slowly added excess EtOH and stirred overnight. THF solvent was removed under vacuum and the resulting mixture was purified by silica gel flash chromatography (hexane/ethyl acetate) to give the subject compound (Yield: 62.8%).

$^1$H NMR (400 MHz, Chloroform-d) δ 9.00 (dd, J=2.4, 0.6 Hz, 1H), 8.25 (dd, J=8.3, 2.4 Hz, 1H), 7.42 (dd, J=8.3, 0.7 Hz, 1H), 4.42 (q, J=7.1 Hz, 2H), 1.41 (t, J=7.1 Hz, 3H); MS (ESI, m/z) calculated for $C_8H_9ClNO_2$ [M+H]$^+$ 186.03 found 186.05.

Step 2: Synthesis of Ethyl 6-((5-bromo-2,3-dihydro-1H-inden-2-yl)amino)nicotinate (A5a)

The subject compound was synthesized according to the same procedure as in Step 1 of Example 1, except for the use of 5-bromo-2,3-dihydro-1H-inden-2-amine instead of 2,3-dihydro-1H-inden-2-amine, and the use of ethyl 6-chloronicotinate (A4a) instead of ethyl 2-chloropyrimidine-5-carboxylate (Yield: 12.4%).

$^1$H NMR (400 MHz, Chloroform-d) δ 8.75 (d, J=1.8 Hz, 1H), 7.99 (dd, J=8.8, 2.2 Hz, 1H), 7.35 (s, 1H), 7.30 (d, J=8.1 Hz, 1H), 7.09 (d, J=8.0 Hz, 1H), 6.36 (d, J=8.8 Hz, 1H), 5.30 (d, J=8.1 Hz, 1H), 4.78-4.59 (m, 1H), 4.33 (q, J=7.1 Hz, 2H), 3.42-3.25 (m, 2H), 2.93-2.74 (m, 2H), 1.36 (t, J=7.1 Hz, 3H); MS (ESI, m/z) calculated for $C_{17}H_{18}BrN_2O_2$ [M+H]$^+$ 361.05 found 361.00.

Step 3: Synthesis of 6-((5-Bromo-2,3-dihydro-1H-inden-2-yl)amino)nicotinohydrazide (A6a)

The subject compound was synthesized according to the same procedure as in Step 2 of Example 1, except for the use of compound A5a instead of compound 5a (Yield: 84.1%).

$^1$H NMR (400 MHz, DMSO-d$_6$) δ 9.43 (s, 1H), 8.49 (d, J=2.0 Hz, 1H), 7.84-7.74 (m, 3H), 7.44 (s, 1H), 7.39-7.30 (m, 2H), 7.25-7.17 (m, 1H), 6.53-6.40 (m, 1H), 4.63 (q, J=5.7 Hz, 1H), 3.28-3.18 (m, 2H), 2.89-2.73 (m, 2H); MS (ESI, m/z) calculated for $C_{15}H_{16}BrN_4O$ [M+H]$^+$ 347.05 found 347.05.

Step 4: Synthesis of 5-(6-((5-Bromo-2,3-dihydro-1H-inden-2-yl)amino)pyridin-3-yl)-1,3,4-oxadiazol-2(3H)-one (A7a)

To a solution of compound A6a (0.2 mmol) in DMF were added 1,1'-carbonyldiimidazole (0.22 mmol) and TEA (0.2 mmol) at room temperature and stirred 3 h. The DMF solvent was removed under vacuum and the crude mixture was purified by silica gel flash chromatography (hexane/ethyl acetate) to give the subject compound (Yield: 84.0%).

$^1$H NMR (400 MHz, DMSO-d$_6$) δ 10.94-10.85 (m, 1H), 10.21 (dd, J=8.9, 2.4 Hz, 1H), 10.13-10.07 (m, 1H), 9.95 (s, 1H), 9.87-9.82 (m, 1H), 9.71 (d, J=8.0 Hz, 1H), 9.12-9.05 (m, 1H), 7.17 (q, J=5.8 Hz, 1H), 5.81-5.71 (m, 2H), 5.38-5.26 (m, 2H); MS (ESI, m/z) calculated for $C_{16}H_{14}BrN_4O_2$ [M+H]$^+$ 373.03 found 373.00.

Step 5: Synthesis of 5-(5-(4-(1H-1,2,3-Triazol-5-yl)piperidin-1-yl)-1,3,4-oxadiazol-2-yl)-N-(5-bromo-2,3-dihydro-1H-inden-2-yl)pyridin-2-amine (17a)

The subject compound was synthesized according to the same procedure as in Step 4 of Example 1, except for the use of compound A7a instead of compound 7a (Yield: 57.2%).

$^1$H NMR (400 MHz, Chloroform-d) δ 8.60 (dd, J=2.4, 0.7 Hz, 1H), 7.98 (dd, J=8.8, 2.4 Hz, 1H), 7.54 (s, 1H), 7.38 (s, 1H), 7.31 (dd, J=7.8, 1.9 Hz, 1H), 7.11 (d, J=7.9 Hz, 1H), 6.46 (dd, J=8.9, 0.8 Hz, 1H), 5.24 (d, J=7.5 Hz, 1H), 4.74-4.62 (m, 1H), 4.19-4.09 (m, 2H), 3.45-3.20 (m, 4H), 3.06 (tt, J=11.4, 3.7 Hz, 1H), 2.95-2.80 (m, 2H), 2.15 (dd, J=13.8, 3.8 Hz, 2H), 1.97-1.83 (m, 2H); MS (ESI, m/z) calculated for $C_{23}H_{24}BrN_8O$ [M+H]$^+$ 507.13, found 507.15.

[Example 13] Synthesis of 5-(5-(4-(1H-1,2,3-Triazol-5-yl)piperidin-1-yl)-1,3,4-oxadiazol-2-yl)-N-(5-bromo-2,3-dihydro-1H-inden-2-yl)pyrazin-2-amine (17b)

The subject compound was synthesized according to the same procedure as in Example 12, except for the use of 5-chloropyrazin-2-carboxylic acid instead of 6-chloronicotinic acid (Yield: 48.5%).

$^1$H NMR (400 MHz, Methanol-d$_4$) δ 8.60 (d, J=1.3 Hz, 1H), 7.93 (d, J=1.5 Hz, 1H), 7.68 (s, 1H), 7.40 (s, 1H), 7.30 (dd, J=8.1, 1.9 Hz, 1H), 7.15 (d, J=8.0 Hz, 1H), 4.77 (tt, J=7.2, 3.6 Hz, 2H), 4.13 (dt, J=13.3, 3.5 Hz, 2H), 3.44-3.32 (m, 4H), 3.10 (ddt, J=11.6, 7.4, 3.7 Hz, 1H), 2.90 (ddd, J=19.0, 16.1, 5.4 Hz, 2H), 2.18-2.08 (m, 2H), 1.93-1.76 (m, 2H); MS (ESI, m/z) calculated for $C_{22}H_{23}BrN_9O$ [M+H]$^+$ 508.12, found 508.15.

[Example 14] Synthesis of 5-(5-(4-(1H-1,2,3-Triazol-5-yl)piperidin-1-yl)-1,3,4-oxadiazol-2-yl)-N-(5-bromo-2,3-dihydro-1H-inden-2-yl)-4-chloropyridin-2-amine (18)

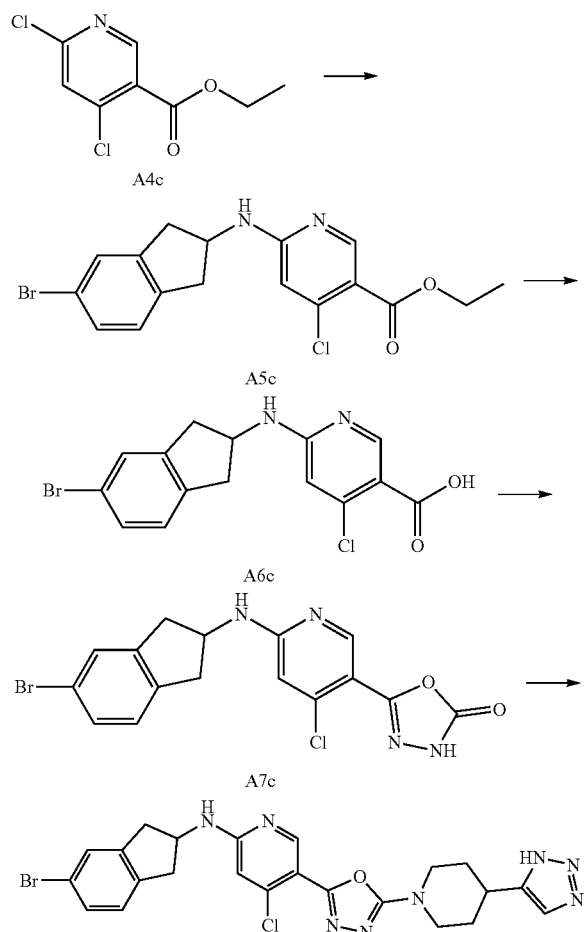

Step 1: Synthesis of ethyl 6-((5-Bromo-2,3-dihydro-1H-inden-2-yl)amino)-4-chloronicotinate (A5c)

The subject compound was synthesized according to the same procedure as compound A5a using ethyl 4,6-dichloronicotinate (Yield: 64.2%).

$^1$H NMR (400 MHz, Chloroform-d) δ 8.68 (s, 1H), 8.40 (d, J=6.3 Hz, 1H), 7.39 (s, 1H), 7.33 (dd, J=8.0, 1.8 Hz, 1H), 7.11 (d, J=8.0 Hz, 1H), 6.62 (s, 1H), 4.40-4.26 (m, 3H), 3.40 (td, J=16.6, 7.0 Hz, 2H), 2.92 (ddd, J=20.7, 16.3, 4.8 Hz, 2H), 1.36 (t, J=7.1 Hz, 3H); MS (ESI, m/z) calculated for $C_{17}H_{17}BrClN_2O_2$[M+H]$^+$ 395.02 found 395.05.

Step 2: Synthesis of 6-((5-Bromo-2,3-dihydro-1H-inden-2-yl)amino)-4-chloronicotinic acid (A6c)

To a solution of compound A5c (0.50 mmol) in EtOH and water was added lithium hydroxide (1.5 mmol) at room temperature and stirred overnight. The resulting mixture was poured into DCM, washed with H$_2$O (40 ml), and dried over MgSO$_4$. The crude mixture was purified by silica gel flash chromatography (hexane/ethyl acetate) to give the subject compound (Yield: 64.2%).

$^1$H NMR (400 MHz, DMSO-d$_6$) δ 8.61 (d, J=6.1 Hz, 1H), 8.51 (s, 1H), 7.47 (s, 1H), 7.35 (dd, J=8.0, 1.9 Hz, 1H), 7.23 (d, J=8.0 Hz, 1H), 6.90 (s, 1H), 4.49 (h, J=6.8 Hz, 1H), 3.38 (ddd, J=20.2, 16.4, 7.0 Hz, 2H), 2.84 (ddd, J=21.3, 16.3, 4.7 Hz, 2H); MS (ESI, m/z) calculated for $C_{15}H_{13}BrClN_2O_2$ [M+H]$^+$ 366.98 found 366.95.

Step 3: Synthesis of 5-(6-((5-Bromo-2,3-dihydro-1H-inden-2-yl)amino)-4-chloropyridin-3-yl)-1,3,4-oxadiazol-2(3H)-yl (A7c)

To a solution of compound A6c (0.25 mmol) in THF was added 1,1'-carbonyldiimidazole (0.27 mmol) under Ar gas at room temperature and stirred for 3 h. To the solution was added hydrazine monohydrate (2.5 mmol) and stirred overnight. The resulting mixture was evaporated under vacuum. 1,1'-carbonyldiimidazole (0.27 mmol) and triethylamine (0.25 mmol) was added to the solution of the crude mixture in DMF. The reaction mixture was stirred 3 h and the crude mixture was purified by silica gel flash chromatography (hexane/ethyl acetate) to give the subject compound (Yield: 59.6%).

$^1$H NMR (400 MHz, DMSO-d$_6$) δ 12.74 (s, 1H), 8.30 (s, 1H), 7.48 (s, 1H), 7.43-7.33 (m, 2H), 7.24 (d, J=8.0 Hz, 1H), 7.04 (s, 1H), 4.65-4.53 (m, 1H), 3.49-3.36 (m, 2H), 2.91-2.76 (m, 2H); MS (ESI, m/z) calculated for $C_{16}H_{13}BrClN_4O_2$[M+H]$^+$ 406.99 found 407.00.

Step 4: Synthesis of 5-(5-(4-(1H-1,2,3-Triazol-5-yl)piperidin-1-yl)-1,3,4-oxadiazol-2-yl)-N-(5-bromo-2,3-dihydro-1H-inden-2-yl)-4-chloropyridin-2-amine (18)

The subject compound was synthesized according to the same procedure as in Step 4 of Example 1 using compound A7c (Yield: 67.8%).

$^1$H NMR (400 MHz, DMSO-d$_6$) δ 14.73 (s, 1H), 8.49 (s, 1H), 8.12 (d, J=6.9 Hz, 1H), 7.69 (s, 1H), 7.50 (d, J=1.9 Hz, 1H), 7.37 (dd, J=8.0, 2.0 Hz, 1H), 7.26 (d, J=8.0 Hz, 1H), 7.02 (s, 1H), 4.60 (tt, J=6.9, 2.8 Hz, 1H), 4.05-3.96 (m, 2H), 3.42 (ddd, J=19.8, 16.3, 6.8 Hz, 2H), 3.25 (td, J=12.5, 2.7 Hz, 2H), 3.01 (tt, J=11.5, 3.7 Hz, 1H), 2.87 (ddd, J=20.8, 16.4, 4.1 Hz, 2H), 2.06-1.96 (m, 2H), 1.70 (qd, J=12.6, 4.2

Hz, 2H); MS (ESI, m/z) calculated for $C_{23}H_{23}BrClN_8O$ [M+H]$^+$ 541.09, found 541.10.

[Example 15] Synthesis of 5-(5-(4-(1H-1,2,3-Triazol-5-yl)piperidin-1-yl)-1,3,4-oxadiazol-2-yl)-N-(3,5-dichlorobenzyl)pyrimidin-2-amine (19a)

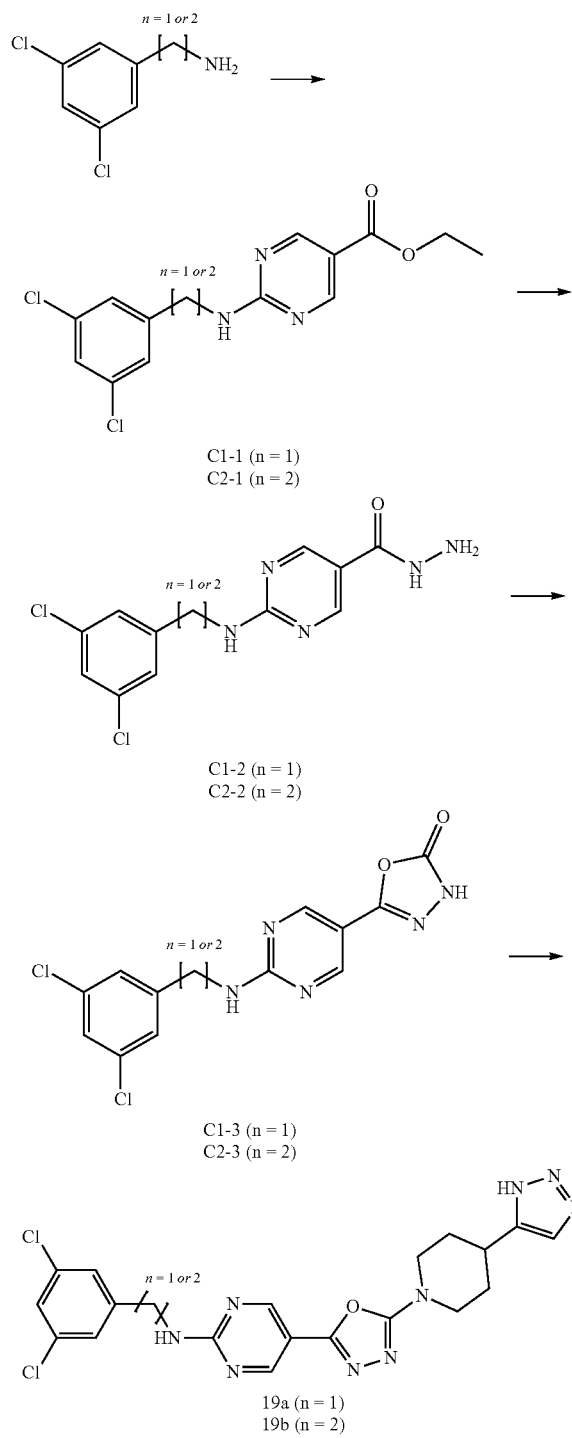

C1-1 (n = 1)
C2-1 (n = 2)

C1-2 (n = 1)
C2-2 (n = 2)

C1-3 (n = 1)
C2-3 (n = 2)

19a (n = 1)
19b (n = 2)

The subject compound was synthesized according to the same procedure as in Example 1, except for the use of (3,5-dichlorophenyl)methanamine instead of 2,3-dihydro-H-inden-2-amine (Yield: 48.70).

$^1$H NMR (400 MHz, DMSO-d$_6$) δ 8.84-8.67 (m, 2H), 8.46 (t, J=6.4 Hz, 1H), 7.69 (s, 1H), 7.48 (t, J=2.0 Hz, 1H), 7.36 (d, J=1.9 Hz, 2H), 4.57 (d, J=6.3 Hz, 2H), 3.99 (dt, J=13.1, 3.5 Hz, 2H), 3.27-3.16 (m, 2H), 3.05-2.95 (m, 1H), 2.07-1.98 (m, 2H), 1.77-1.62 (m, 2H); MS (ESI, m/z) calculated for $C_{20}H_{20}Cl_2N_9O$ [M+H]$^+$ 472.12, found 472.10.

[Example 16] Synthesis of 5-(5-(4-(H-1,2,3-Triazol-5-yl)piperidin-1-yl)-1,3,4-oxadiazol-2-yl)-N-(3,5-dichlorophenethyl)pyrimidin-2-amine (19b)

The subject compound was synthesized according to the same procedure as in Example 1, except for the use of diisopropylethylamine instead of 2,3-dihydro-1H-inden-2-amine (Yield: 54.60%).

$^1$H NMR (400 MHz, DMSO-d$_6$) δ 8.73 (d, J=8.1 Hz, 2H), 7.97 (t, J=5.8 Hz, 1H), 7.70 (s, 1H), 7.42 (t, J=1.9 Hz, 1H), 7.32 (d, J=1.9 Hz, 2H), 3.99 (dt, J=13.1, 3.6 Hz, 2H), 3.59 (q, J=6.7 Hz, 2H), 3.23 (td, J=12.7, 2.8 Hz, 2H), 3.01 (tt, J=11.6, 3.7 Hz, 1H), 2.89 (t, J=6.9 Hz, 2H), 2.03 (dd, J=13.5, 3.4 Hz, 2H), 1.79-1.61 (m, 2H); MS (ESI, m/z) calculated for $C_{21}H_{22}Cl_2N_9O$ [M+H]$^+$ 486.13, found 486.15.

[Example 17] Synthesis of 1-(4-(1H-1,2,3-Triazol-5-yl)piperidin-1-yl)-3-(2-((2,3-dihydro-1H-inden-2-yl)amino)pyrimidin-5-yl)propan-1-one (20a)

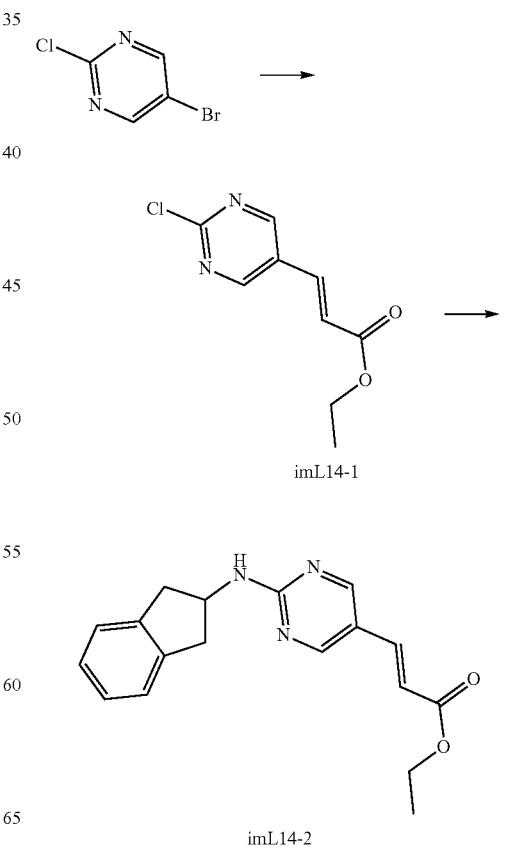

imL14-1 imL14-2

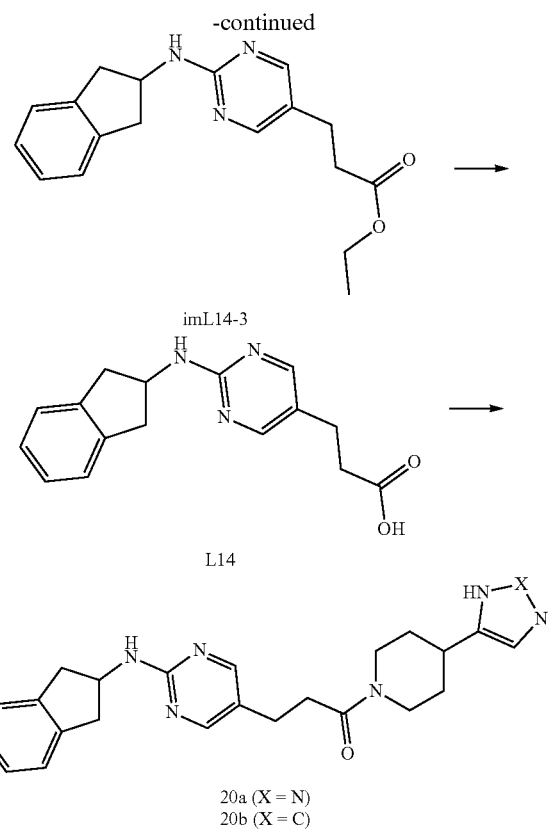

Step 1: Synthesis of (E)-ethyl 3-(2-chloropyrimidine-5-yl)acrylate (imL14-1): A mixture of 5-bromo-2-chloropyrimidine (0.19 g, 1.00 mmol), ethyl acrylate (0.42 mL, 4.00 mmol), palladium (II) diacetate (8.98 mg, 0.04 mmol) and tri(o-tolyl)phosphine (30.43 mg, 0.10 mmol) in dimethylformamide (2 mL) and diisopropylethylamine (1 mL) was heated at reflux for 4 h, then cooled to room temperature. The solvent was evaporated to dryness and extracted with ethyl acetate. The extract was washed with brine and dried over sodium sulfate, then concentrated. The residue was separated by column chromatography (ethyl acetate/hexane) to give the subject compound as a light yellow solid (0.15 g, 71.2%).

$^1$H NMR (400 MHz, CDCl$_3$) δ 8.76 (d, J=0.6 Hz, 2H), 7.59 (d, J=16.2 Hz, 1H), 6.58 (d, J=16.2 Hz, 1H), 4.30 (q, J=7.2 Hz, 2H), 1.35 (t, J=7.1 Hz, 3H).

Step 2: Synthesis of (E)-ethyl 3-(2-((2,3-dihydro-1H-inden-2-yl)amino)pyrimidine-5-yl)acrylate (imL14-2)

The subject compound was synthesized according to the same procedure as in Step 1 of Example 1, using imL14-1 (0.11 g, 0.50 mmol) instead of ethyl 2-chloropyrimidine-5-carboxylate and using 2-aminoindane (0.80 g, 6.00 mmol) and triethylamine (1.01 g, 10 mmol) as white solid (0.11 g, 71.5%).

$^1$H NMR (400 MHz, CDCl$_3$) δ 8.38 (br s, 2H), 7.48 (d, J=16.1 Hz, 1H), 7.26-7.14 (m, 4H), 6.29 (d, J=16.1 Hz, 1H), 6.01 (s, 1H), 4.96-4.78 (m, 1H), 4.26 (q, J=7.1 Hz, 2H), 3.41 (dd, J=16.0, 7.0 Hz, 2H), 2.90 (dd, J=16.0, 4.8 Hz, 2H), 1.34 (t, J=7.1 Hz, 3H).

Step 3: Synthesis of Ethyl 3-(2-((2,3-dihydro-1H-inden-2-yl)amino)pyrimidine-5-yl)propanoate (imL14-3)

In the round bottom flask containing imL14-2 (92.81 mg, 0.30 mmol) in ethyl acetate/methanol/tetrahydrofuran (1:2:1) (20 mL), palladium hydroxide on carbon (50 mg) was slowly added to the mixture at room temperature. The reaction mixture was stirred at room temperature under hydrogen gas for 6 h. The mixture was filtrated through Celite® and the filtrate was concentrated. The residue was purified by column chromatography (Ethyl acetate/Hexane) to give the subject compound as a white solid (78.56 mg, 84.1%).

$^1$H NMR (400 MHz, CDCl$_3$) δ 8.10 (s, 2H), 7.25-7.13 (m, 4H), 5.65 (d, J=7.8 Hz, 1H), 4.84-4.68 (m, 1H), 4.13 (q, J=7.2 Hz, 2H), 3.38 (dd, J=16.0, 7.0 Hz, 2H), 2.86 (dd, J=15.9, 5.0 Hz, 2H), 2.74 (t, J=7.5 Hz, 2H), 2.54 (t, J=7.3 Hz, 2H), 1.25 (t, J=7.1 Hz, 3H).

Step 4: Synthesis of 3-(2-((2,3-Dihydro-1H-inden-2-yl)amino)pyrimidine-5-yl)propanoic acid (L14)

A solution of lithium hydroxide (5.00 mmol) in water (2 mL) was added to the solution of imL14-3 (1.00 mmol) in mixture of tetrahydrofuran/methanol (18 ml: 2 ml). The reaction mixture was stirred at room temperature for 6 h. Then solvent was evaporated and dissolved again in water and acidified by 1M hydrochloric acid. The mixture was extracted with ethyl acetate and washed with water. The organic layer was dried over anhydrous sodium sulfate and concentrated. The product was purified by column chromatography (Ethyl acetate/Hexane) to give the subject compound as a white solid (60.33 mg, 84.4%).

Step 5: Synthesis of 1-(4-(1H-1,2,3-Triazol-5-yl)piperidin-1-yl)-3-(2-((2,3-dihydro-1H-inden-2-yl)amino)pyrimidin-5-yl)propan-1-one (20a)

To a 10-mL vial containing 2 ml of N,N'-dimethylformamide were added L14 (0.10 mmol), 4-(1H-1,2,3-triazol-5-yl)piperidine·HCl (22.64 mg, 0.12 mmol) and N,N-diisopropylethylamine (38.77 mg, 0.30 mmol). N,N,N',N'-Tetramethyl-O-(1H-benzotriazol-1-yl)uronium hexafluorophosphate (HBTU) (45.51 mg, 0.12 mmol) was then added to stirring mixture. The reaction mixture was continued to stir at room temperature overnight. The solvent was evaporated to dryness and the crude product was separated by column chromatography (dichloromethane/methanol) to give the subject compound as a white solid (36.95 mg, 88.5%).

$^1$H NMR (400 MHz, CDCl$_3$) δ 13.71 (s, 1H), 8.19 (s, 2H), 7.47 (s, 1H), 7.23-7.18 (m, 2H), 7.18-7.13 (m, 2H), 5.77 (d, J=7.6 Hz, 1H), 4.83-4.70 (m, 1H), 4.71-4.57 (m, 1H), 3.94-3.81 (m, 1H), 3.37 (dd, J=16.0, 7.1 Hz, 2H), 3.21-3.09 (m, 1H), 3.07-2.94 (m, 1H), 2.91-2.73 (m, 5H), 2.60 (t, J=7.2 Hz, 2H), 2.08-1.98 (m, 2H), 1.71-1.49 (m, 2H); HRMS (ESI) m/z (M+H)$^+$ calcd for C$_{23}$H$_{28}$N$_7$O=418.24; found 418.2354.

[Example 18] Synthesis of 1-(4-(1H-Imidazol-5-yl)piperidin-1-yl)-3-(2-((2,3-dihydro-1H-inden-2-yl)amino)pyrimidin-5-yl)propan-1-one (20b)

The subject compound was synthesized according to the same procedure as in Example 17, except for the use of (1H-imidazol-5-yl)piperidine (18.14 mg, 0.12 mmol) instead of 4-(1H-1,2,3)-triazol-5-yl)piperidine·HCl in Step 5 (27.49 mg, 68.0%).

¹H NMR (400 MHz, CDCl₃) δ 9.97 (s, 1H), 8.17 (s, 2H), 7.55 (d, J=1.2 Hz, 1H), 7.25-7.19 (m, 2H), 7.19-7.13 (m, 2H), 6.74 (s, 1H), 5.40 (d, J=7.8 Hz, 1H), 4.80-4.71 (m, 1H), 4.69-4.61 (m, 1H), 3.90-3.80 (m, 1H), 3.37 (dd, J=15.9, 7.0 Hz, 2H), 3.16-3.07 (m, 1H), 2.89-2.77 (m, 5H), 2.76-2.68 (m, 1H), 2.58 (t, J=7.4 Hz, 2H), 2.09-1.98 (m, 2H), 1.60-1.44 (m, 2H); HRMS (ESI) m/z (M+H)+ calcd for C₂₄H₂₉N₆O=417.24; found 417.2400.

[Example 19] Synthesis of 1-(4-(1H-1,2,3-Triazol-5-yl)piperidin-1-yl)-4-(5-((2,3-dihydro-1H-inden-2-yl)amino)-1,3,4-thiadiazol-2-yl)butan-1-one (21a)

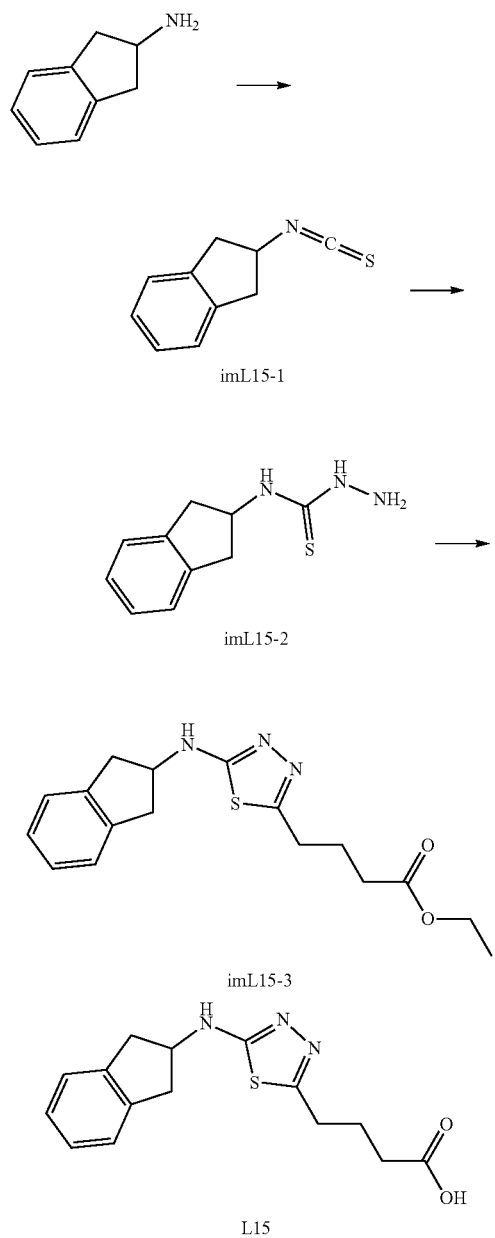

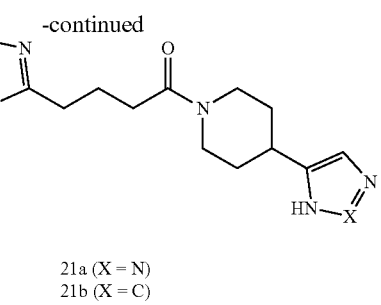

21a (X = N)
21b (X = C)

Step 1: Synthesis of 2-Isothiocyanato-2,3-dihydro-1H-indene (imL15-1)

To the cooling mixture of 2-aminoindan (0.13 g, 1.00 mmol) and N,N-diisopropylethylamine (38.77 mg, 0.30 mmol) in dichloromethane (5 mL) was added dropwise thiophosgene (115.00 μL, 0.15 mmol) at 0° C. The reaction mixture was stirred at room temperature for 3 h, then solvent was evaporated to dryness. The residue was dissolved in ethyl acetate and washed with brine. The organic layer was dried over anhydrous sodium sulfate and concentrated. The product was purified by column chromatography (Hexane) to give the subject compound as a light brown solid (0.173 g, 98.8%).

¹H NMR (400 MHz, CDCl₃) δ 7.26-7.19 (m, 4H), 4.53 (tt, J=6.9, 5.2 Hz, 1H), 3.32 (dd, J=15.9, 7.0 Hz, 2H), 3.16 (dd, J=15.8, 5.2 Hz, 2H).

Step 2: Synthesis of N-(2,3-dihydro-1H-inden-2-yl)hydrazinecarbothioamide (imL15-2)

Hydrazine hydrate (200 μL) was added to the solution of imL15-1 (0.14 g, 0.08 mmol) in ethanol (5 mL). The reaction mixture was stirred at room temperature overnight. The solvent was evaporated to dryness and extracted with ethyl acetate and washed with brine. The organic layer was dried over anhydrous sodium sulfate and concentrated. The product was purified by column chromatography (Ethyl acetate/Hexane) to give the subject compound as a light yellow solid (0.156 g, 94.3%).

¹H NMR (400 MHz, CDCl₃) δ 7.59 (s, 1H), 7.28-7.14 (m, 4H), 5.24-5.13 (m, 1H), 3.68 (s, 1H), 3.43 (dd, J=16.2, 7.2 Hz, 2H), 2.93 (dd, J=16.2, 4.7 Hz, 2H), 1.37-1.16 (m, 2H).

Step 3: Synthesis of Ethyl 4-(5-((2,3-dihydro-1H-inden-2-yl)amino)-1,3,4-thiadiazol-2-yl)butanoate (imL15-3)

A solution of ethyl 4-cyanobutanoate (70.59 mg, 0.50 mmol) and imL15-2 (0.10 g, 0.50 mmol) was stirred in trifluoroacetic acid (3 mL) at 80° C. overnight. The mixture was cooled to 0° C. and quenched with saturated sodium hydrogen carbonate solution, then extracted with ethyl acetate. The organic layer was dried over anhydrous sodium sulfate and concentrated. The product was purified by column chromatography (dichloromethane/methanol) to give the subject compound as a white solid (0.10 g, 62.5%).

¹H NMR (400 MHz, CDCl₃) δ 7.26-7.13 (m, 4H), 6.01 (s, 1H), 4.42 (p, J=5.7 Hz, 1H), 4.13 (q, J=7.1 Hz, 2H), 3.38 (dd, J=16.1, 6.9 Hz, 2H), 3.11-2.86 (m, 4H), 2.41 (t, J=7.4 Hz, 2H), 2.05 (p, J=7.4 Hz, 2H), 1.26 (t, J=7.1 Hz, 3H).

Step 4: Synthesis of 4-(5-((2,3-Dihydro-1H-inden-2-yl)amino)-1,3,4-thiadiazol-2-yl)butanoic acid (L15)

The subject compound was synthesized according to the same procedure as in Step 4 of Example 17 using imL15-3 (0.10 g, 0.30 mmol) as a white solid (68.90 mg, 75.7%).

Step 5: Synthesis of 1-(4-(1H-1,2,3-Triazol-5-yl)piperidin-1-yl)-4-(5-((2,3-dihydro-1H-inden-2-yl)amino)-1,3,4-thiadiazol-2-yl)butan-1-one (21a)

To a 10-mL vial containing 2 ml of N,N'-dimethylformamide were added L15 (0.10 mmol), 4-(1H-1,2,3-triazol-5-yl)piperidine·HCl (0.12 mmol) and N,N-diisopropylethylamine (0.30 mmol). N,N,N',N'-Tetramethyl-O-(1H-benzotriazol-1-yl)uronium hexafluorophosphate (HBTU) (0.12 mmol) was then added to stirring mixture. The reaction mixture was continued to stir at room temperature overnight. The solvent was evaporated to dryness and the crude product was separated by column chromatography (dichloromethane/methanol) to give the subject compound as a white solid (19.34 mg, 44.2%).

$^1$H NMR (400 MHz, CDCl$_3$) δ 7.47 (s, 1H), 7.24-7.16 (m, 4H), 6.33-5.57 (m, 1H), 4.66-4.56 (m, 1H), 4.50-4.40 (m, 1H), 3.94-3.85 (m, 1H), 3.43-3.33 (m, 2H), 3.19-3.09 (m, 1H), 3.06-2.92 (m, 5H), 2.77-2.68 (m, 1H), 2.53-2.39 (m, 2H), 2.19-2.04 (m, 2H), 2.04-1.92 (m, 2H), 1.80-1.61 (m, 2H); HRMS (ESI) m/z (M+H)+ calcd for C$_{22}$H$_{28}$N$_7$OS=438.21; found 438.2076

[Example 20] Synthesis of 1-(4-(1H-Imidazol-5-yl)piperidin-1-yl)-4-(5-((2,3-dihydro-1H-inden-2-yl)amino)-1,3,4-thiadiazol-2-yl)butan-1-one (21b): The subject compound was synthesized according to the same procedure as in Step 5 of Example 19, except for the use of 4-(1H-imidazol-5-yl)piperidine (18.14 mg, 0.12 mmol) instead of 4-(1H-1,2,3-triazol-5-yl)piperidine·HCl (0.12 mmol), as a white solid (38.24 mg, 68.0%).

$^1$H NMR (400 MHz, CDCl$_3$) δ 7.52 (s, 1H), 7.22-7.12 (m, 4H), 6.73 (s, 1H), 6.62-6.51 (m, 1H), 4.60-4.53 (m, 1H), 4.49-4.39 (m, 1H), 3.87-3.78 (m, 1H), 3.40-3.28 (m, 2H), 3.12-3.03 (m, 1H), 3.01-2.90 (m, 4H), 2.88-2.78 (m, 1H), 2.70-2.59 (m, 1H), 2.48-2.34 (m, 2H), 2.11-1.89 (m, 4H), 1.68-1.49 (m, 2H); HRMS (ESI) m/z (M+H)+ calcd for C$_{23}$H$_{29}$N$_6$OS=437.21; found 437.2126.

[Example 21] Synthesis of 1-(4-(1H-1,2,3-Triazol-5-yl)piperidin-1-yl)-4-(5-((2,3-dihydro-1H-inden-2-yl)amino)-1,3,4-oxadiazol-2-yl)butan-1-one (22a)

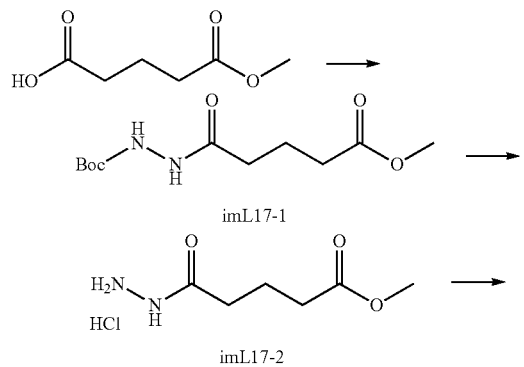

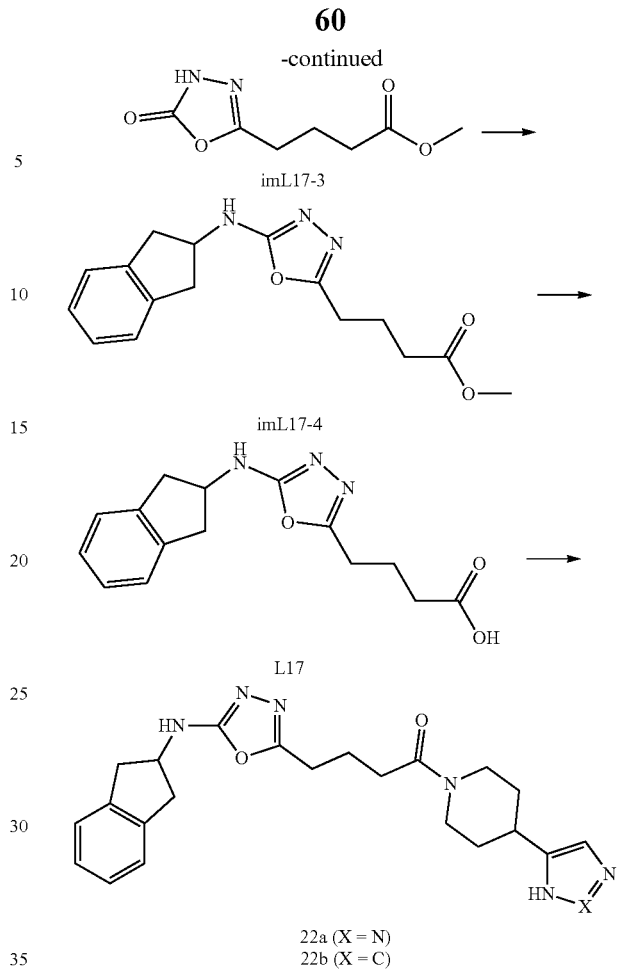

22a (X = N)
22b (X = C)

Step 1: Synthesis of tert-Butyl 2-(5-methoxy-5-oxopentanoyl)hydrazine carboxylate (imL17-1)

To a mixture containing monomethyl glutarate (5.00 mmol), tert-butyl carbazate (6.00 mmol) and 4-dimethylaminopyridine (0.025 mmol) in dichloromethane (2 mL) was added N-(3-dimethylaminopropyl)-N'-ethylcarbodiimide hydrochloride (6.00 mmol). The reaction mixture was continued to stir at room temperature overnight. The mixture was extracted with dichloromethane and washed with water. The organic layer was dried over anhydrous sodium sulfate and concentrated. The crude product was separated by column chromatography (ethyl acetate/hexane) to give the subject compound as a white solid (1.14 g, 87.6%).

Step 2: Synthesis of Methyl 5-hydrazinyl-5-oxopentanoate hydrochloride (imL17-2)

The subject compound was synthesized according to the same procedure as in Step 2 of Preparative Example 1 using imL17-1 (0.52 g, 2.00 mmol) as white solid (quantitative).
$^1$H NMR (400 MHz, MeOD) δ 3.66 (s, 3H), 2.41 (t, J=7.3 Hz, 2H), 2.36 (t, J=7.4 Hz, 2H), 1.94 (p, J=7.4 Hz, 2H).

Step 3: Synthesis of Methyl 4-(5-oxo-4,5-dihydro-1,3,4-oxadiazol-2-yl)butanoate (imL17-3)

To a solution of im17-2 (0.52 g, 2.00 mmol) in dioxane (10 mL) was added 4.0 M hydrogen chloride solution in dioxane (2 mL). The reaction mixture was stirred at room temperature overnight. The solvent was evaporated to dryness to give the subject compound as a white solid (quantitative).

$^1$H NMR (400 MHz, MeOD) δ 3.66 (s, 3H), 2.41 (t, J=7.3 Hz, 2H), 2.36 (t, J=7.4 Hz, 2H), 1.94 (p, J=7.4 Hz, 2H).

Step 4: Synthesis of Methyl 4-(5-((2,3-dihydro-1H-inden-2-yl)amino)-1,3,4-oxadiazol-2-yl)butanoate (imL17-4)

The subject compound was synthesized according to the same procedure as in Step 4 of Example 1 using imL17-3 (0.149 mg, 0.80 mmol) and 2-aminoindane (0.13 g, 0.96 mmol), as a white solid (0.12 g, 50.2%).

$^1$H NMR (400 MHz, CDCl$_3$) δ 7.27-7.15 (m, 4H), 5.34 (s, 1H), 4.51 (qt, J=6.9, 4.6 Hz, 1H), 3.67 (s, 3H), 3.36 (dd, J=16.1, 6.9 Hz, 2H), 2.97 (dd, J=16.1, 4.6 Hz, 2H), 2.74 (t, J=7.3 Hz, 2H), 2.43 (t, J=7.3 Hz, 2H), 2.03 (p, J=7.3 Hz, 2H).

Step 5: Synthesis of 4-(5-((2,3-Dihydro-1H-inden-2-yl)amino)-1,3,4-oxadiazol-2-yl)butanoic acid (L17)

The subject compound was synthesized according to the same procedure as in Step 4 of Example 17, except for the use of imL17-4 (0.12 g, 0.40 mmol) instead of imL14-3, as a white solid (0.11 g, 96.8%).

$^1$H NMR (400 MHz, CDCl$_3$) δ 8.42 (br s, 1H), 7.25-7.14 (m, 4H), 6.09 (br s, 1H), 4.47 (tt, J=7.0, 5.2 Hz, 1H), 3.35 (dd, J=16.0, 7.0 Hz, 2H), 2.95 (dd, J=16.0, 5.2 Hz, 2H), 2.77 (t, J=7.3 Hz, 2H), 2.43 (t, J=7.1 Hz, 2H), 2.02 (p, J=7.2 Hz, 2H).

Step 6: Synthesis of 1-(4-(1H-1,2,3-Triazol-5-yl)piperidin-1-yl)-4-(5-((2,3-dihydro-1H-inden-2-yl)amino)-1,3,4-oxadiazol-2-yl)butan-1-one (22a)

The subject compound was synthesized according to the same procedure as in Step 5 of Example 19 using L17 (28.73 mg, 0.10 mmol) and 4-(1H-1,2,3-triazol-5-yl)piperidine·HCl (22.64 mg, 0.12 mmol), as a white solid (28.37 mg, 67.3%).

$^1$H NMR (400 MHz, CDCl$_3$) δ 13.51 (s, 1H), 7.46 (s, 1H), 7.25-7.14 (m, 4H), 5.54-5.41 (m, 1H), 4.63-4.55 (m, 1H), 4.55-4.48 (m, 1H), 3.95-3.87 (m, 1H), 3.41-3.32 (m, 2H), 3.19-3.10 (m, 1H), 3.06-2.92 (m, 3H), 2.83-2.70 (m, 3H), 2.54-2.41 (m, 2H), 2.17-1.93 (m, 4H), 1.78-1.58 (m, 2H); HRMS (ESI) m/z (M+H)+ calcd for C$_{22}$H$_{28}$N$_7$O$_2$=422.2299; found 422.2300

[Example 22] Synthesis of 1-(4-(1H-Imidazol-5-yl)piperidin-1-yl)-4-(5-((2,3-dihydro-1H-inden-2-yl)amino)-1,3,4-oxadiazol-2-yl)butan-1-one (22b)

The subject compound was synthesized according to the same procedure as in Example 21, except for the use of 4-(1H-imidazol-5-yl)piperidine (18.14 mg, 0.12 mmol) instead of 4-(1H-1,2,3-triazol-5-yl)piperidine·HCl in Step 6 (Yield: 69.4%).

$^1$H NMR (400 MHz, CDCl$_3$) δ 7.50 (d, J=1.2 Hz, 1H), 7.23-7.14 (m, 4H), 6.73 (s, 1H), 6.00-5.92 (m, 1H), 4.62-4.55 (m, 1H), 4.53-4.44 (m, 1H), 3.93-3.81 (m, 1H), 3.38-3.30 (m, 2H), 3.13-3.05 (m, 1H), 3.02-2.92 (m, 2H), 2.89-2.80 (m, 1H), 2.79-2.70 (m, 2H), 2.70-2.61 (m, 1H), 2.48-2.36 (m, 2H), 2.10-1.91 (m, 4H), 1.70-1.52 (m, 2H); HRMS (ESI) m/z (M+H)+ calcd for C$_{23}$H$_{29}$N$_6$O$_2$=421.2347; found 421.2348.

[Example 23] Synthesis of 1-(4-(1H-1,2,3-Triazol-5-yl)piperidin-1-yl)-2-((5-((2,3-dihydro-1H-inden-2-yl)amino)-1,3,4-thiadiazol-2-yl)methoxy)ethanone (23)

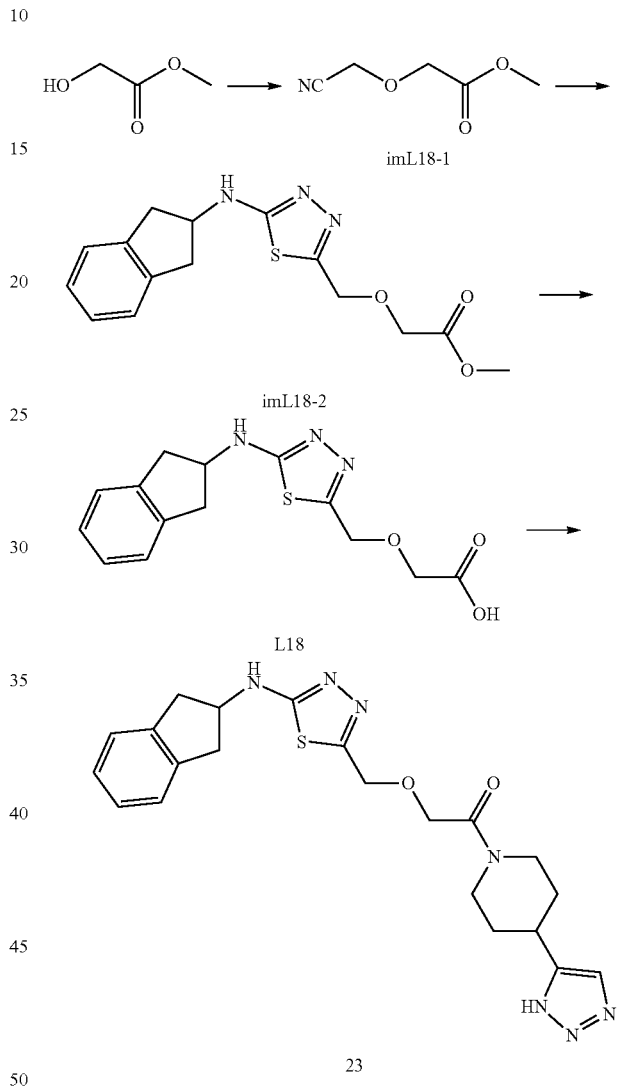

Step 1: Synthesis of Methyl 2-(cyanomethoxy)acetate (imL18-1)

To a solution of methyl glycolate (0.45 g, 5.00 mmol) in dried tetrahydrofuran (10 mL) was added slowly sodium hydride 60% (0.24 g, 6.00 mmol) at room temperature. The reaction mixture was continued to stir at room temperature for 1 h until the bubbles ceased. Bromoacetonitrile (0.72 g, 6.00 mmol) was added to mixture and the reaction mixture was continued to stir at room temperature overnight. The mixture was extracted with diethyl ether and washed with water. The organic layer was dried over anhydrous sodium sulfate and concentrated. The product was purified by column chromatography (Ethyl acetate/Hexane) to give the subject compound as a colorless oil (0.395 g, 61.2%).

¹H NMR (400 MHz, CDCl₃) δ 4.46 (s, 2H), 4.25 (s, 2H), 3.80 (s, 3H).

Step 2: Synthesis of Methyl 2-((5-((2,3-dihydro-1H-inden-2-yl)amino)-1,3,4-thiadiazol-2-yl)methoxy)acetate (imL18-2)

The mixture of imL15-2 (0.41 g, 2.00 mmol) and imL18-1 (0.26 g, 2.00 mmol) was heated in trifluoroacetic acid (3 mL) at 80° C. overnight. The mixture was cooled at 0° C. and quenched with saturated sodium hydrogen carbonate solution, and then extracted with ethyl acetate. The organic layer was dried over anhydrous sodium sulfate and concentrated. The product was purified by column chromatography (dichloromethane/methanol) to give the subject compound as a white solid (0.29 g, 62.5%).
¹H NMR (400 MHz, CDCl₃) δ 7.26-7.16 (m, 4H), 6.04 (s, 1H), 4.84 (s, 2H), 4.52-4.38 (m, 1H), 4.17 (s, 2H), 3.77 (s, 3H), 3.40 (dd, J=16.1, 6.8 Hz, 2H), 2.99 (dd, J=16.1, 4.7 Hz, 2H).

Step 3: Synthesis of 2-((5-((2,3-Dihydro-1H-inden-2-yl)amino)-1,3,4-thiadiazol-2-yl)methoxy)acetic acid (L18)

The subject compound was synthesized according to the same procedure as in Step 4 of Example 17 using imL18-2 (0.32 g, 1.00 mmol) (Yield: 91.3%).
¹H NMR (400 MHz, DMSO-d₆) δ 8.09 (d, J=6.2 Hz, 1H), 7.30-7.11 (m, 4H), 4.70 (s, 2H), 4.52-4.39 (m, 1H), 3.91 (s, 2H), 3.29 (dd, J=16.1, 7.1 Hz, 2H), 2.89 (dd, J=16.1, 5.1 Hz, 2H).

Step 4: Synthesis of 1-(4-(1H-1,2,3-Triazol-5-yl)piperidin-1-yl)-2-((5-((2,3-dihydro-1H-inden-2-yl)amino)-1,3,4-thiadiazol-2-yl)methoxy)ethanone (23)

The subject compound was synthesized according to the same procedure as in Step 5 of Example 17 using L18 (30.53 mg, 0.10 mmol) and 4-(1H-1,2,3-triazol-5-yl)piperidine·HCl (22.64 mg, 0.12 mmol), as a white solid (Yield: 60.2%).
¹H NMR (400 MHz, CDCl₃) δ 7.46 (s, 1H), 7.24-7.12 (m, 4H), 6.49 (br s, 1H), 4.86-4.73 (m, 2H), 4.60-4.49 (m, 1H), 4.48-4.41 (m, 1H), 4.33-4.18 (m, 2H), 3.80-3.70 (m, 1H), 3.42-3.33 (m, 2H), 3.17-3.07 (m, 1H), 3.06-2.93 (m, 3H), 2.83-2.73 (m, 1H), 2.06-1.95 (m, 2H), 1.79-1.58 (m, 2H); HRMS (ESI) m/z (M+H)⁺ calcd for C₂₁H₂₅N₇O₂S=462.1863; found 462.1686.

[Example 24] Synthesis of N-(5,6-difluoro-2,3-dihydro-1H-inden-2-yl)-5-(5-(4-(5-(trifluoromethyl)-1,3,4-oxadiazol-2-yl)piperidin-1-yl)-1,3,4-oxadiazol-2-yl)pyrimidin-2-amine The subject compound was synthesized according to the same procedure as in Example 1, except for the use of 5,6-difluoro-2,3-dihydro-1H-inden-2-amine (4e) instead of 2,3-dihydro-1H-inden-2-amine (4a), and the use of 2-(piperidine-4-yl)-5-(trifluoromethyl)-1,3,4-oxadiazole trifluoroacetate salt (im19) instead of 4-(1H-1,2,3-triazol-5-yl)piperidine·HCl (3) (14.7 mg Yield: 30%).
¹H NMR (400 MHz, CDCl₃): δ 8.79 (s, 2H), 7.03 (t, J=8.7 Hz, 2H), 5.71 (d, J=7.6 Hz, 1H), 4.94-4.84 (m, 1H), 4.14 (d, J=13.6 Hz, 2H), 3.49 (d, J=4.7 Hz, 1H), 3.43-3.25 (m, 5H), 2.86 (dd, J=16.0, 5.2 Hz, 2H), 2.30 (dd, J=13.7, 3.0 Hz, 2H), 2.17-2.02 (m, 2H); LCMS m/z 535 [M+H]⁺

[Example 25] Synthesis of N-(5,6-difluoro-2,3-dihydro-1H-inden-2-yl)-5-(5-(4-(5-(difluoromethyl)-1,3,4-oxadiazol-2-yl)piperidin-1-yl)-1,3,4-oxadiazol-2-yl)pyrimidin-2-amine The subject compound was synthesized according to the same procedure as in Example 1, except for the use of 5,6-difluoro-2,3-dihydro-1H-inden-2-amine (4e) instead of 2,3-dihydro-1H-inden-2-amine (4a), and the use of 2-(difluoromethyl)-5-(piperidine-4-yl)-1,3,4-oxadiazole (im20) instead of 4-(1H-1,2,3-triazol-5-yl)piperidine·HCl (3) (32.5 mg, Yield: 62.4%).
¹H NMR (400 MHz, CDCl₃): δ 8.78 (s, 2H), 7.03 (t, J=8.8 Hz, 2H), 6.72-6.98 (t, J=52 Hz, 1H), 5.77 (d, J=7.4 Hz, 7H), 4.89 (m, 1H), 4.13 (d, J=13.5 Hz, 2H), 3.43-3.23 (m, 4H), 2.86 (dd, J=16.0, 5.2 Hz, 2H), 2.29 (dd, J=10.6, 3.2 Hz, 2H), 2.18-2.01 (m, 2H), 1.51 (dd, J=12.0, 6.8 Hz, 1H); LCMS m/z 517[M+H]⁺

[Example 26] Synthesis of 5-(5-(4-(1,2,4-Oxadiazol-3-yl)piperidin-1-yl)-1,3,4-oxadiazol-2-yl)-N-(5,6-difluoro-2,3-dihydro-1H-inden-2-yl)pyrimidin-2-amine The subject compound was synthesized according to the same procedure as in Example 1, except for the use of 5,6-difluoro-2,3-dihydro-1H-inden-2-amine (4e) instead of 2,3-dihydro-1H-inden-2-amine (4a), and the use of 3-(piperidine-4-yl)-1,2,4-oxadiazole instead of 4-(1H-1,2,3-triazol-5-yl)piperidine·HCl (3) (12.6 mg, Yield: 29.8%).
¹H NMR (400 MHz, DMSO-d6): δ 9.53 (s, 1H), 8.75 (s, 2H), 8.25 (d, J=6.7 Hz, 1H), 7.27 (t, J=9.3 Hz, 2H), 4.69 (dd, J=13.8, 7.2 Hz, 1H), 3.96 (d, J=13.1 Hz, 2H), 3.24 (dd, J=16.1, 7.6 Hz, 4H), 3.17 (dd, J=9.0, 6.4 Hz, 1H), 2.88 (dd, J=16.1, 6.5 Hz, 2H), 2.06 (d, J=11.1 Hz, 2H), 1.83-1.70 (m, 2H); LCMS m/z 467[M+H]⁺

[Example 27] Synthesis of 5-(5-(4-(1,3,4-Oxadiazol-2-yl)piperidin-1-yl)-1,3,4-oxadiazol-2-yl)-N-(5,6-difluoro-2,3-dihydro-1H-inden-2-yl)pyrimidin-2-amine The subject compound was synthesized according to the same procedure as in Example 1, except for the use of 5,6-difluoro-2,3-dihydro-1H-inden-2-amine (4e) instead of 2,3-dihydro-1H-inden-2-amine (4a), and the use of 2-(piperidine-4-yl)-1,3,4-oxadiazole instead of 4-(1H-1,2,3-triazol-5-yl)piperidine·HCl (3) (7.6 mg, Yield: 6.7%).
¹H NMR (400 MHz, DMSO-d6): δ 9.17 (s, 1H), 8.76 (d, J=11.8 Hz, 2H), 8.26 (d, J=8.0 Hz, 1H), 7.28 (t, J=9.1 Hz, 2H), 4.69 (dd, J=15.0, 7.9 Hz, 1H), 3.95 (d, J=12.5 Hz, 2H), 3.24 (dd, J=18.0, 9.2 Hz, 5H), 2.88 (dd, J=16.3, 6.2 Hz, 2H), 2.12 (d, J=13.3 Hz, 2H), 1.81 (dd, J=22.6, 9.9 Hz, 2H); LCMS m/z 467 [M+H]⁺

[Example 28] Synthesis of 5-(5-(4-(1H-Tetrazol-1-yl)piperidin-1-yl)-1,3,4-oxadiazol-2-yl)-N-(5,6-difluoro-2,3-dihydro-1H-inden-2-yl)pyrimidin-2-amine The subject compound was synthesized according to the same procedure as in Example 1, except for the use of 5,6-difluoro-2,3-dihydro-1H-inden-2-amine (4e) instead of 2,3-dihydro-1H-inden-2-amine (4a), and the use of 4-(1H- tetrazol-1-yl)piperidine instead of 4-(1H-1,2,3-triazol-5-yl)piperidine·HCl (3) (20.9 mg, Yield: 54.4%).

$^1$H NMR (400 MHz, DMSO-d6): (DMSO-d6) δ 9.00 (s, 1H), 8.77 (d, J=10.6 Hz, 2H), 8.27 (d, J=6.7 Hz, 1H), 7.28 (t, J=9.4 Hz, 2H), 5.21 (dd, J=14.3, 8.5 Hz, 1H), 4.68 (dd, J=14.1, 6.9 Hz, 1H), 4.02 (d, J=13.5 Hz, 2H), 3.39 (t, J=11.3 Hz, 2H), 3.24 (dd, J=16.2, 7.6 Hz, 2H), 2.88 (dd, J=16.0, 6.3 Hz, 2H), 2.31 (d, J=9.8 Hz, 2H), 2.20-2.06 (m, 2H); LCMS m/z 467 [M+H]$^+$

[Example 29] Synthesis of N-(5,6-difluoro-2,3-dihydro-1H-inden-2-yl)-5-(5-(4-(4-methyl-1H-1,2,3-triazol-5-yl)piperidin-1-yl)-1,3,4-oxadiazol-2-yl)pyrimidin-2-amine The subject compound was synthesized according to the same procedure as in Example 1, except for the use of 5,6-difluoro-2,3-dihydro-1H-inden-2-amine (4e) instead of 2,3-dihydro-1H-inden-2-amine (4a), and the use of 4-(4-methyl-1H-1,2,3-triazol-5-yl)piperidine (im21) instead of 4-(1H-1,2,3-triazol-5-yl)piperidine·HCl (3) (3.7 mg, Yield: 20%).

$^1$H NMR (400 MHz, CDCl$_3$): δ 8.79 (s, 2H), 7.02 (t, J=8.8 Hz, 2H), 5.90 (d, J=7.7 Hz, 1H), 4.88 (dd, J=12.6, 5.4 Hz, 1H), 4.16 (d, J=12.9 Hz, 2H), 3.36 (dd, J=16.0, 7.0 Hz, 2H), 3.30-3.20 (m, 2H), 2.88 (d, J=5.1 Hz, 1H), 2.84 (d, J=5.0 Hz, 1H), 2.33 (s, 3H), 2.06-1.90 (m, 2H), 1.52-1.39 (m, 2H); LCMS m/z 480 [M+H]$^+$

[Example 30] Synthesis of (E)-1-(4-(1H-1,2,3-triazol-5-yl)piperidin-1-yl)-3-(2-((5,6-difluoro-2,3-dihydro-1H-inden-2-yl)amino)pyrimidin-5-yl)prop-2-en-1-one Step 1: Synthesis of ethyl (E)-3-(2-((5,6-difluoro-2,3-dihydro-1H-inden-2-yl)amino)pyrimidin-5-yl)acrylate (imL22-1)

A mixture of imL14-1 (0.249 g, 1.17 mmol), 5,6-difluoro-2,3-dihydro-1H-inden-2-amine (0.160 g, 0.585 mmol), diisopropylethylamine (1.5 g, 11.7 mmol) and n-BuOH (1.2 mL) was stirred in a microwave reactor at 150° C. for 2 h. The reaction mixture was concentrated under vacuum, and then purified by column chromatography (hexane/ethyl acetate) to give the subject compound as a brown solid (0.132 g, 65.3%).

$^1$H NMR (400 MHz, DMSO-d6) δ8.67 (s, 2H), 8.09 (d, J=6.8 Hz, 1H), 7.48 (d, J=16.1 Hz, 1H), 7.26 (t, J=9.3 Hz, 2H), 6.51 (d, J=16.1 Hz, 1H), 4.66 (dd, J=13.8, 6.8 Hz, 1H), 4.15 (dd, J=14.1, 7.0 Hz, 2H), 3.22 (dd, J=16.1, 7.7 Hz, 2H), 2.86 (dd, J=15.8, 6.3 Hz, 2H), 1.22 (t, J=7.1 Hz, 3H); LCMS m/z 346[M+H]$^+$

Step 2: Synthesis of (E)-3-(2-((5,6-difluoro-2,3-dihydro-1H-inden-2-yl)amino)pyrimidin-5-yl)acrylic acid (L22)

The subject compound was synthesized according to the same procedure as in Step 4 of Example 17, except for the use of imL22-1 instead of imL14-3, as a light yellow solid (0.90 g, 97.0%).

$^1$H NMR (400 MHz, DMSO-d6) δ12.17 (bs, 1H), 8.64 (s, 2H), 8.05 (d, J=7.2 Hz, 1H), 7.41 (d, J=16.0 Hz, 1H), 7.26 (t, J=9.3 Hz, 2H), 6.41 (d, J=16.2 Hz, 1H), 4.66 (dd, J=14.0, 6.8 Hz, 1H), 3.26-3.19 (m, 2H), 2.86 (dd, J=16.1, 6.6 Hz, 2H); LCMS m/z 318[M+H]$^+$

Step 3: Synthesis of (E)-1-(4-(1H-1,2,3-triazol-5-yl)piperidin-1-yl)-3-(2-((5,6-difluoro-2,3-dihydro-1H-inden-2-yl)amino)pyrimidin-5-yl)prop-2-en-1-one (30)

The subject compound was synthesized according to the same procedure as in Step 5 of Example 17, except for the use of L22 instead of L14, as a yellow solid (0.019 g, 29.3%).

$^1$H NMR (400 MHz, DMSO-d6): δ8.71 (s, 2H), 8.06 (s, 1H), 7.67 (s, 1H), 7.35 (d, J=15.3 Hz, 1H), 7.26 (t, J=9.2 Hz, 2H), 7.21 (d, J=15.5 Hz, 1H), 4.69-4.63 (m, 1H), 4.39 (dd, J=62.1, 11.5 Hz, 4H), 3.23 (dd, J=16.0, 7.5 Hz, 2H), 3.00 (dd, J=18.4, 7.4 Hz, 1H), 2.86 (dd, J=16.2, 6.6 Hz, 2H), 1.95 (s, 2H), 1.51 (s, 2H); LCMS m/z 452[M+H]$^+$

[Example 31] Synthesis of 5-(5-(4-(1-Benzyl-1H-1,2,3-triazol-5-yl)piperidin-1-yl)oxazol-2-yl)-N-(2,3-dihydro-1H-inden-2-yl)pyrimidin-2-amine (31)

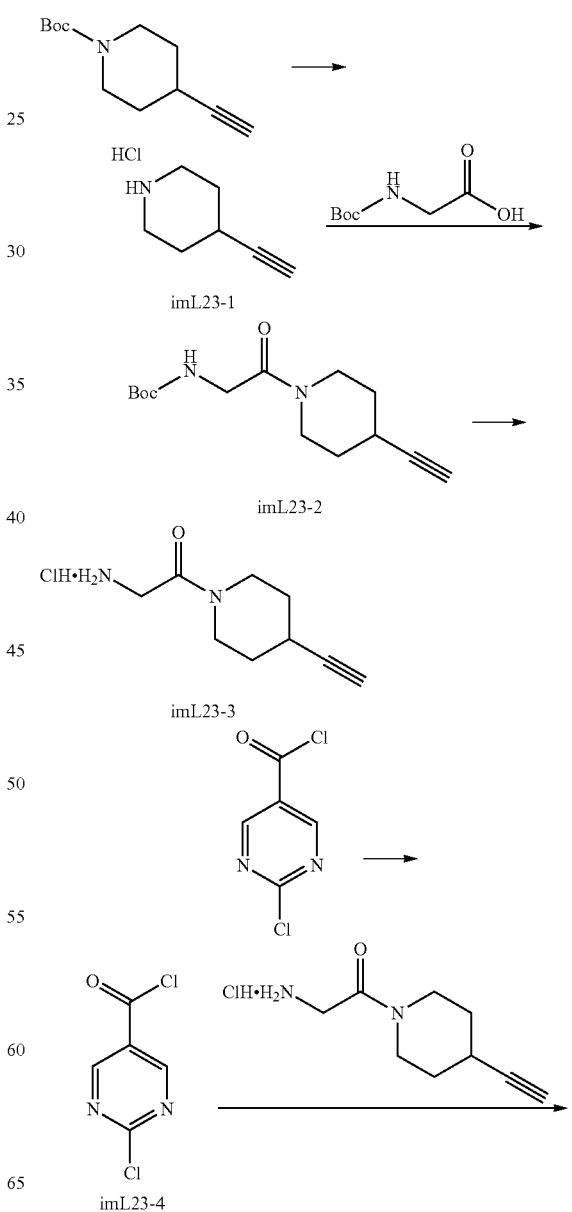

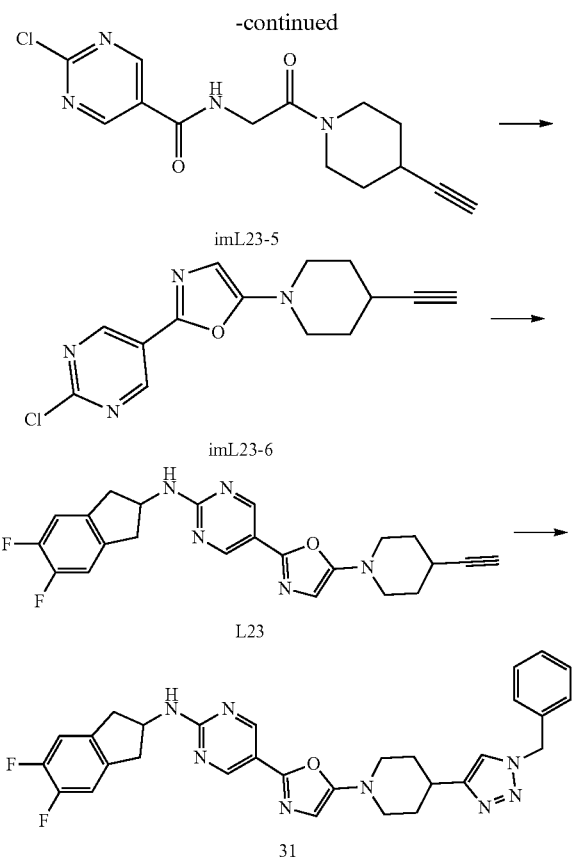

Step 1-1: Synthesis of 4-Ethynylpiperidine hydrochloride (imL23-1)

tert-Butyl 4-ethynylpiperidine-1-carboxylate (12.0 g, 57.4 mmol) was dissolved in $Et_2O$ (100 mL), and cooled to 0° C. HCl (4 M, 100 mL) in $Et_2O$ was added and the mixture was stirred for 20 h. $Et_2O$ was evaporated and PE was added. Then the solid was filtered and washed with PE and $Et_2O$ to give the subject compound (imL23-1) as a white solid (8.3 g, Yield:99.4%).
LCMS m/z 110 $[M+H]^+$

Step 1-2: Synthesis of tert-Butyl (2-(4-ethynylpiperidin-1-yl)-2-oxoethyl)carbamate (imL23-2)

To a solution of 2-((tert-butoxycarbonyl)amino)acetic acid (10.0 g, 57.1 mmol) in DMF (50 mL) were added EDCI (13.1 g, 68.5 mmol) and HOBt (9.2 g, 68.5 mmol) at 0° C., then stirred at room temperature for 0.5 h. imL23-1 (8.3 g, 57.1 mmol, HCl salt) and TEA (17.3 g, 171.3 mmol) were added and stirred at room temperature overnight. The reaction mixture was extracted with EA, washed with water and NaCl, dried over $Na_2SO_4$, filtered and concentrated. The subject compound (imL23-2) was obtained as a yellow oil (15.1 g, Yield:99.7%).
LCMS m/z 267$[M+H]^+$

Step 1-3: Synthesis of 2-Amino-1-(4-ethynylpiperidin-1-yl)ethanone hydrochloride (imL23-3)

imL23-2 (15.1 g, 57.1 mmol) was dissolved in $Et_2O$ (100 mL) and cooled to 0° C. HCl (4 M, 70 mL) in $Et_2O$ was added and the mixture was stirred for 20 h. $Et_2O$ was evaporated and PE was added. Then the solid was filtered and washed with PE and $Et_2O$ to give the subject compound (imL23-3) as a white solid (17.7 g, Yield:100%).
LCMS m/z 167 $[M+H]^+$

Step 2-1: Synthesis of 2-Chloropyrimidine-5-carbonyl chloride (imL23-4)

To a solution of 2-chloropyrimidine-5-carboxylic acid (30.0 g, 189 mmol) in DCM (200 mL) were slowly added oxalyl dichloride (48.0 g, 378 mmol) and 6 drops of DMF at 0° C. The reaction mixture was stirred at room temperature for 20 h. The reaction mixture was evaporated to dryness to give the subject compound (imL23-4) as a white solid (33 g, Yield: 99.8%), which was used in the following reaction without purification.

Step 2-2: Synthesis of 2-Chloro-N-(2-(4-ethynylpiperidin-1-yl)-2-oxoethyl)pyrimidine-5-carboxamide (imL23-5)

To a solution of imL23-3 (17.7 g, 87.0 mmol) in DCM (400 mL) were added TEA (52.7 g, 522 mmol) and DMAP (600 mg). The reaction mixture was stirred at room temperature for 1 h, and cooled to 0° C. imL23-4 (16.9 g, 95.7 mmol) was added and stirred at room temperature overnight. The reaction mixture was extracted with DCM, washed with water and NaCl, dried over $Na_2SO_4$, filtered and concentrated. The product was purified by column chromatography (DCM:MeOH=100:1~20:1) to give the subject compound (imL23-5) as a yellow solid (15.8 g, Yield: 59.4%).
LCMS m/z 307 $[M+H]^+$

Step 2-3: Synthesis of 2-(2-Chloropyrimidin-5-yl)-5-(4-ethynylpiperidin-1-yl)oxazole (imL23-6)

To a solution of $PPh_3$ (51.0 g, 193.9 mmol) in DCM (400 mL) was added perchloroethane (46.5 g, 193.9 mmol) after cooled to 0° C. under Ar gas. The mixture was stirred for 0.5 h at 0~20° C. After cooling to 0° C. again, imL23-5 (15.0 g, 48.9 mmol) was added and the reaction mixture was stirred for 1 h at room temperature. $Na_2CO_3$ (aq) was added to the mixture to pH 9-10 and stirred at room temperature overnight. The reaction mixture was extracted with DCM, washed with water and NaCl, followed by sat. $Na_2CO_3$, and then dried over $Na_2SO_4$, filtered and concentrated. Diluted with $Et_2O$ to remove $P(O)Ph_3$ solid, concentrated the filtrate and purified with $Al_2O_3$ column (PE:EA=20:1~10:1~DCM:EA=100:0~20:1) to give 7.3 g of a yellow solid (crude, 88% purity). It was purified again with an $Al_2O_3$ column (0.1% TEA) (PE:EA=50:1~1:1) to give 5.3 g of a yellow solid, which was purified with PE to give the subject compound (imL23-6) as a yellow solid (5.2 g, Yield:36.9%).
$^1$H NMR (400 MHz, $CDCl_3$): δ 9.04 (s, 2H), 6.21 (s, 1H), 3.44-3.50 (m, 2H), 3.10-3.16 (m, 2H), 2.68-2.70 (m, 1H), 2.15 (brs, 1H), 1.95-2.01 (m, 2H), 2.12-2.06 (m, 2H), 1.80-1.87 (m, 2H); LCMS m/z 289 $[M+H]^+$

Step 2-4: Synthesis of N-(2,3-dihydro-1H-inden-2-yl)-5-(5-(4-ethynylpiperidin-1-yl)oxazol-2-yl)pyrimidin-2-amine (L23)

The mixture of 2-aminoindane (0.703 g, 4.16 mmol), imL23-6 (1 g, 3.46 mmol), triethylamine (1.2 mL, 8.30 mmol) and dioxane (35 mL) was stirred at 100° C. for 1 hour. After cooling, the solvent was evaporated and the product was purified by column chromatography (hexane/ethyl acetate) to give the subject compound as a brown solid (0.190 g, 14.2%).

Step 2-5: Synthesis of 5-(5-(4-(1-Benzyl-1H-1,2,3-triazol-5-yl)piperidin-1-yl)oxazol-2-yl)-N-(2,3-dihydro-1H-inden-2-yl)pyrimidin-2-amine (31)

To a solution of L23 (0.145 g, 0.376 mmol) in DMF/MeOH (3.4 mL/0.38 mL) were added 0.5 M benzylazide solution (in DCM) (502 μL, 0.564 mmol), CuI (0.115 g, 0.602 mmol) and DIPEA (128 μL, 0.564 mmol), stirred at 40° C. for 1 hour. The reaction mixture was extracted with EA, the organic layer was washed with brine, dried over MgSO$_4$, filtered and concentrated. The obtained residue was purified by column chromatography (DCM/MeOH) to give the subject compound as a brown solid (1.3 mg, 6.7%).

$^1$H NMR (400 MHz, DMSO-d6): δ 8.71 (s, 2H), 8.01 (d, J=6.8 Hz, 1H), 7.99 (s, 1H), 7.37-7.26 (m, 5H), 7.16 (d, J=21.5 Hz, 4H), 6.23 (s, 1H), 5.53 (s, 2H), 3.57 (d, J=12.6 Hz, 1H), 3.24 (dd, J=15.1, 7.8 Hz, 4H), 2.91 (d, J=7.8 Hz, 2H), 2.87 (t, J=7.0 Hz, 3H), 2.00 (d, J=12.8 Hz, 2H), 1.69 (dd, J=13.4, 4.6 Hz, 2H); LCMS m/z 519[M+H]$^+$

[Example 32] Synthesis of 5-(5-(4-(1H-1,2,3-triazol-5-yl)piperidin-1-yl)-1,3,4-oxadiazol-2-yl)-N-(5,6-difluoro-2,3-dihydro-1H-inden-2-yl)-N-methylpyrimidin-2-amine

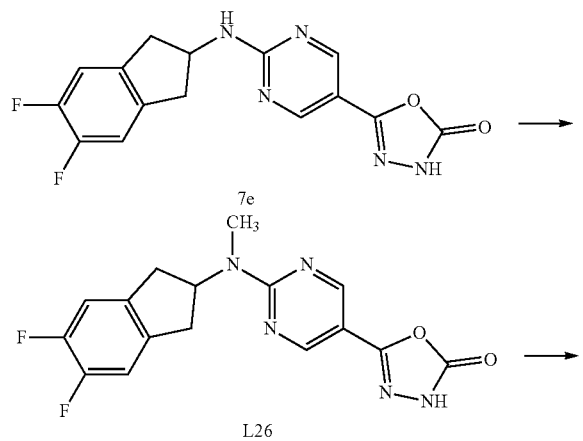

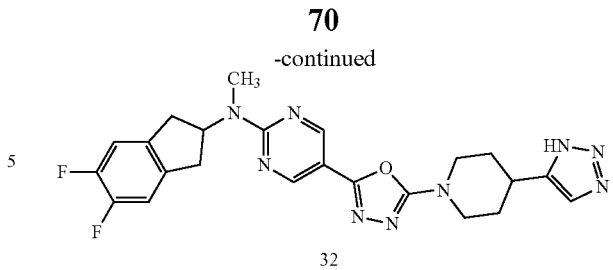

Step 1: Synthesis of 5-(2-((5,6-Difluoro-2,3-dihydro-1H-inden-2-yl)(methyl)amino)pyrimidin-5-yl)-1,3,4-oxadiazol-2(3H)-one (L26)

To a solution of 7e (20 mg, 0.060 mmol) in DMF (0.6 mL) was added NaH (60%) (7.2 mg, 0.181 mmol) at 0° C. and stirred at 0° C. for 30 minutes. CH$_3$I (11 μL, 0.181 mmol) was added and stirred at room temperature overnight. The reaction mixture was extracted with EA, the organic layer was washed with brine, dried over Na$_2$SO$_4$, filtered and concentrated. The obtained residue was purified by column chromatography (DCM/MeOH) to give the subject compound (L26) as a white solid (9.9 mg, Yield: 47.5%).
LCMS m/z 346[M+H]$^+$ Step 2: Synthesis of 5-(5-(4-(1H-1,2,3-triazol-5-yl)piperidin-1-yl)-1,3,4-oxadiazol-2-yl)-N-(5,6-difluoro-2,3-dihydro-1H-inden-2-yl)-N-methylpyrimidin-2-amine (32)

L26 (8.1 mg, 0.024 mmol), 4-(1H-1,2,3-triazol-5-yl)piperidine trifluoroacetic acid salt (3-1) (7.0 mg, 0.028 mmol), BOP reagent (12.4 mg, 0.028 mmol) and DIPEA (12 μL, 0.070 mmol) were dissolved in DMF (0.1 mL) and stirred at room temperature for 6 h. The reaction mixture was extracted with EA, the organic layer was washed with brine, dried over Na$_2$SO$_4$, filtered and concentrated. The obtained residue was purified by column chromatography (DCM/MeOH) to give the subject compound (32) as a white solid (1.5 mg, Yield: 13.3%).

$^1$H NMR (400 MHz, DMSO-d6): δ 8.81 (s, 2H), 7.69 (s, 1H), 7.31 (t, J=9.2 Hz, 2H), 5.75 (dt, J=15.4, 7.9 Hz, 1H), 3.97 (d, J=13.2 Hz, 2H), 3.27-3.10 (m, 5H), 3.05 (d, J=6.9 Hz, 2H), 3.01 (s, 3H), 2.02 (d, J=11.9 Hz, 2H), 1.69 (dd, J=22.4, 11.0 Hz, 2H); LCMS m/z 480 [M+H]$^+$

[Example 33] Synthesis of N-(5,6-difluoro-2,3-dihydro-1H-inden-2-yl)-5-(5-(4-(1-methyl-1H-1,2,3-triazol-5-yl)piperidin-1-yl)-1,3,4-oxadiazol-2-yl)pyrimidin-2-amine

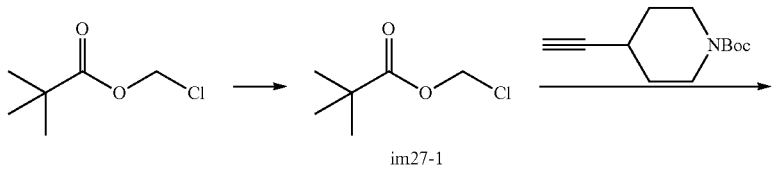

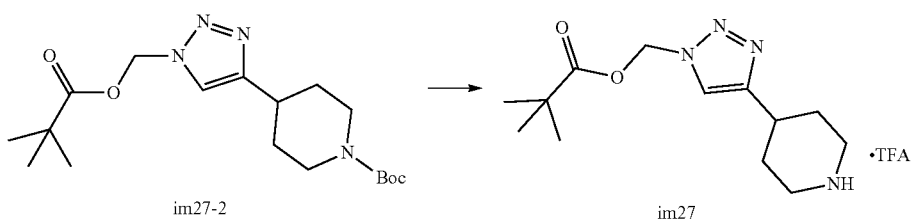

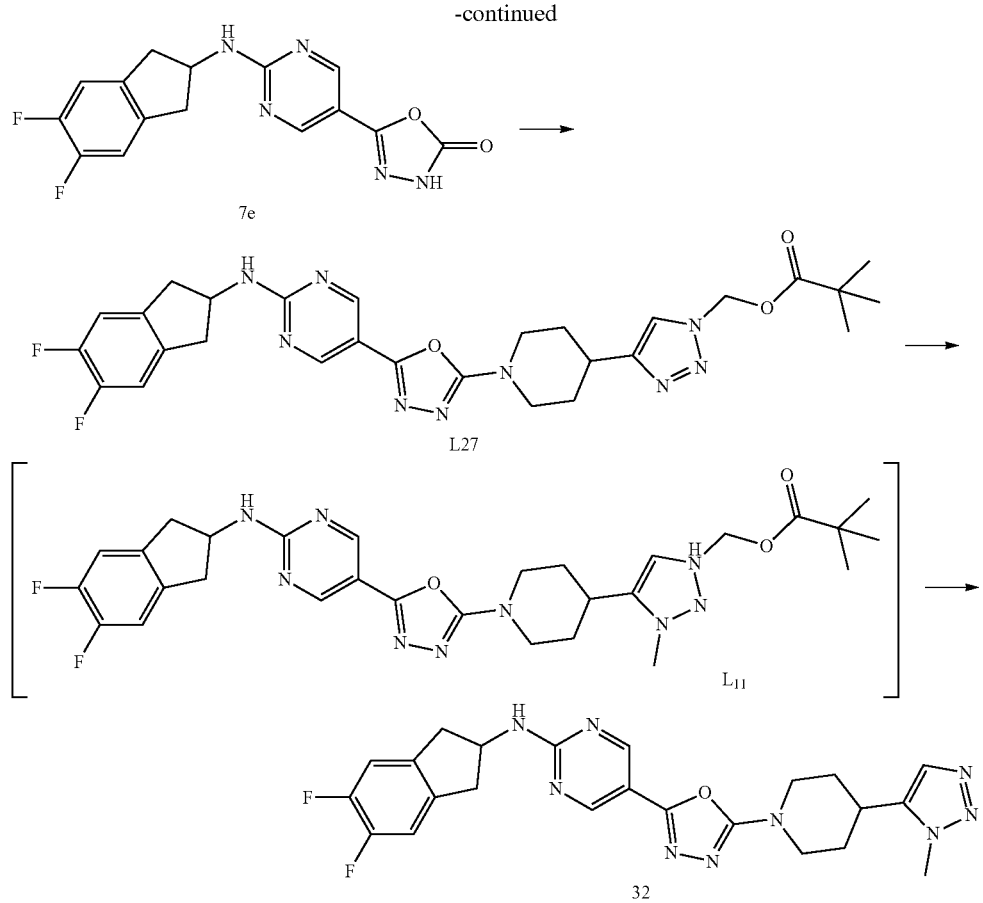

Step 1-1: Synthesis of Azidomethyl pivalate (im27-1)

To a solution of chloromethyl pivalate (1 g, 6.64 mmol) in $H_2$ (1.7 mL) was added $NaN_3$ (0.648 g, 9.96 mmol) and stirred at 90° C. overnight. The reaction mixture was diluted with water, extracted with EA, dried over $Na_2SO_4$, filtered and concentrated. The subject compound (im27-1) was obtained as a colorless liquid (1 g, Yield: 96%) and used in the following reaction without purification.

Step 1-2: Synthesis of tert-Butyl 4-(1-((pivaloyloxy)methyl)-1H-1,2,3-triazol-4-yl)piperidine-1-carboxylate (im27-2)

To a solution of im27-1 (1 g, 6.36 mmol) and tert-butyl 4-ethynyl-1-piperidinecarboxylate (1.3 g, 6.36 mmol) in $THF/H_2O$ (12.7 mL) were added CuOAc (78.0 mg, 0.636 mmol) and NaOAc (1.7 g, 19.1 mmol) and stirred at room temperature for 4 h. The reaction mixture was extracted with EA, and the organic layer was dried on $Na_2SO_4$, filtered, and concentrated. The obtained residue was purified by column chromatography (DCM/MeOH) to give the subject compound (im27-2) as a light green oil (1.18 g, Yield:51%).

$^1$H NMR (400 MHz, $CDCl_3$): δ 7.53 (s, 1H), 6.20 (s, 2H), 4.15 (s, 2H), 2.88 (dd, J=26.4, 13.4 Hz, 2H), 2.02 (d, J=13.1 Hz, 2H), 1.65-1.56 (m, 3H), 1.46 (s, 9H), 1.18 (s, 9H).

Step 1-3: Synthesis of (4-(Piperidin-4-yl)-1H-1,2,3-triazol-1-yl)methyl pivalate trifluoroacetic acid salt (im27)

To a solution of im27-2 (0.658 g, 1.80 mmol) in DCM (17.9 mL) was added TFA (6.0 mL) at 0° C. and stirred at room temperature overnight. The reaction mixture was concentrated under reduced pressure to give the subject compound (im27) as a white solid (0.493 g, Yield:74.9%), which was used in the following reaction without purification.

Step 2-1: Synthesis of (4-(1-(5-(2-((5,6-Difluoro-2,3-dihydro-1H-inden-2-yl)amino)pyrimidin-5-yl)-1,3,4-oxadiazol-2-yl)piperidin-4-yl)-1H-1,2,3-triazol-1-yl)methyl pivalate (L27)

To a solution of 7e (0.374 mg, 1.13 mmol) in DMF (5.6 mL) was added im27 (0.494 g, 1.35 mmol), then cooled to 0° C. and added DIPEA (576 μL, 3.39 mmol). The mixture was stirred at 0° C. for 30 minutes, then BOP reagent (0.599 g, 1.35 mmol) was added and stirred at room temperature overnight. The reaction mixture was extracted with EA, the organic layer was washed with brine, dried over $Na_2SO_4$, filtered and concentrated. The obtained residue was purified by column chromatography (DCM/MeOH) to give the subject compound (L27) as a yellow solid (0.344 g, Yield: 52.61%).

LC/MS m/z 580[M+H]$^+$

Step 2-2: Synthesis of N-(5,6-difluoro-2,3-dihydro-1H-inden-2-yl)-5-(5-(4-(1-methyl-1H-1,2,3-triazol-5-yl)piperidin-1-yl)-1,3,4-oxadiazol-2-yl)pyrimidin-2-amine (33)

L27 (0.25 g, 0.431 mmol) and MeOTf (57 μL, 0.518 mmol) were dissolved in DCM (500 μL) and stirred at room temperature overnight. The reaction mixture was dissolved in MeOH (2.2 mL), $K_2CO_3$ (0.119 g, 1.24 mmol) was added, and the mixture was stirred at room temperature for 4 h. The reaction mixture was filtered, washed with DCM, and the filtrate was concentrated. The obtained residue was purified by column chromatography (DCM/MeOH) to give the subject compound (33) as a yellow solid (17.7 mg, Yield:6.9%).

$^1$H NMR (400 MHz, DMSO-d6): δ 8.76 (s, 2H), 8.25 (d, J=6.8 Hz, 1H), 7.57 (s, 1H), 7.27 (t, J=9.4 Hz, 2H), 4.69 (dd, J=12.8, 5.5 Hz, 1H), 4.03 (d, J=12.5 Hz, 1H), 3.99 (s, 3H), 3.24 (dd, J=16.1, 8.0 Hz, 4H), 3.06 (t, J=11.8 Hz, 2H), 2.91-2.85 (m, 2H), 1.95 (d, J=13.7 Hz, 2H), 1.64 (dd, J=23.9, 11.1 Hz, 2H); LCMS m/z 480 [M+H]$^+$

[Example 34] Synthesis of N-(5,6-difluoro-2,3-dihydro-1H-inden-2-yl)-5-(5-(4-(1-methyl-1H-1,2,3-triazol-4-yl)piperidin-1-yl)-1,3,4-oxadiazol-2-yl)pyrimidin-2-amine phy (DCM/MeOH) to give the subject compound (L28) as a white solid (0.101 g, Yield:39.6%).
LCMS m/z 423[M+H]$^+$ Step 2: Synthesis of N-(5,6-difluoro-2,3-dihydro-1H-inden-2-yl)-5-(5-(4-(1-methyl-1H-1,2,3-triazol-4-yl)piperidin-1-yl)-1,3,4-oxadiazol-2-yl)pyrimidin-2-amine (34)

MeI (33 mg, 0.232 mmol) and $NaN_3$ (15.1 mg, 0.697 mmol) were dissolved in $THF/H_2O$ (v/v=1:1, 2.3 mL) and stirred at room temperature overnight. L28 (98 mg, 0.232 mmol), CuOAc (2.9 mg, 0.023 mmol) and NaOAc (57.2 mg, 0.697 mmol) were added to the reaction mixture and stirred at room temperature overnight. The reaction mixture was extracted with EA, and the organic layer was dried over $Na_2SO_4$, filtered, and concentrated. The obtained residue was purified by column chromatography (DCM/MeOH) to give the subject compound (34) as a yellow solid (1.6 mg, Yield:1.4%).

$^1$H NMR (400 MHz, DMSO-d6): δ 8.75 (s, 2H), 8.24 (d, J=6.8 Hz, 1H), 7.87 (s, 1H), 7.27 (t, J=9.4 Hz, 2H), 4.68 (dd, J=13.8, 6.9 Hz, 1H), 3.97 (s, 5H), 3.24 (dd, J=15.9, 7.3 Hz, 4H), 2.96 (d, J=11.0 Hz, 1H), 2.88 (dd, J=16.2, 6.5 Hz, 2H),

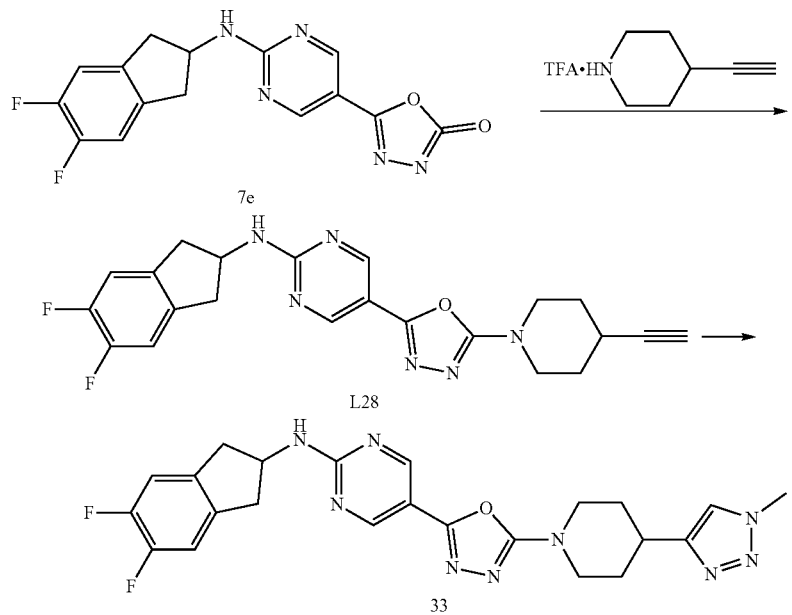

Step 1: Synthesis of N-(5,6-difluoro-2,3-dihydro-1H-inden-2-yl)-5-(5-(4-ethynylpiperidin-1-yl)-1,3,4-oxadiazol-2-yl)pyrimidin-2-amine (L28)

To a solution of 7e (0.2 g, 0.603 mmol) in DMF (3.1 mL) was added 4-ethynylpiperidine trifluoroacetic acid salt (0.150 g, 0.724 mmol), cooled to 0° C. and added DIPEA (308 μL, 1.81 mmol). The mixture was stirred at 0° C. for 30 minutes, then BOP reagent (0.320 g, 0.724 mmol) was added and stirred at room temperature for 3 h. The reaction mixture was extracted with EA, and the organic layer was washed with brine, dried over $Na_2SO_4$, filtered and concentrated. The obtained residue was purified by column chromatogra 2.00 (d, J=11.5 Hz, 2H), 1.66 (dd, J=20.0, 11.1 Hz, 2H); LCMS m/z 480 [M+H]$^+$

[Example 35] Synthesis of N-indan-2-yl-5-[3-[4-(1H-triazol-5-yl)-1-piperidyl]-4,5-dihydroisoxazol-5-yl]pyrimidin-2-amine (35)

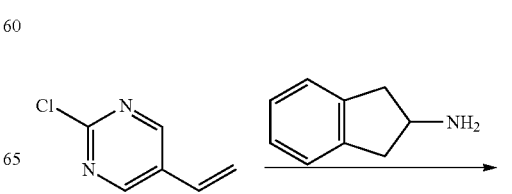

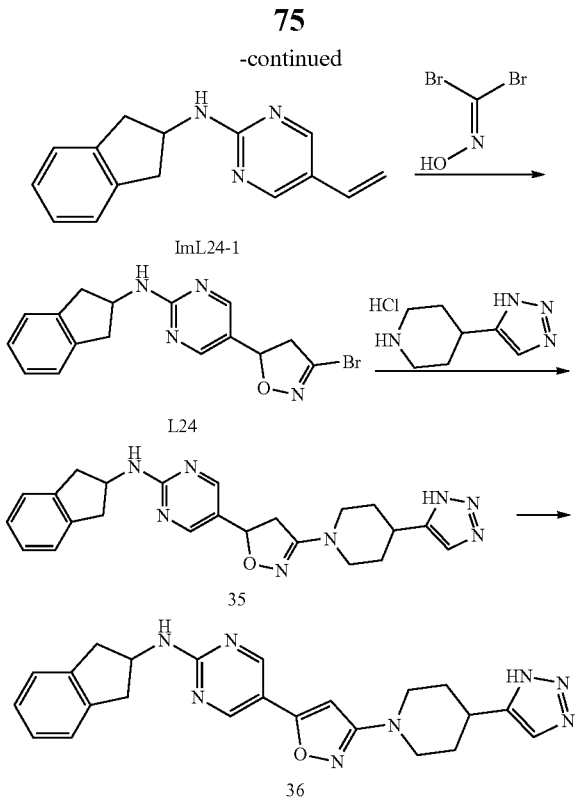

Step 1: Synthesis of N-(2,3-dihydro-1H-inden-2-yl)-5-vinylpyrimidin-2-amine (imL24-1)

2-Aminoindane (1 g, 7.508 mmol), 2-chloro-5-vinylpyrimidine (0.704 g, 5.005 mmol), and DIPEA (17 mL, 100.1 mmol) were dissolved in n-BuOH 10 mL, then reacted in a microwave reactor for 2 h. After confirming the completion of the reaction by TLC, the reaction mixture was concentrated. The obtained residue is then adsorbed onto silica gel and purified by silica gel column chromatography (15% EA in Hexane) to give the subject compound (imL24-1) as a white solid (0.837 g, Yield:47%).

LCMS m/z 238 [M+H]$^+$

Step 2: Synthesis of 5-(3-Bromo-4,5-dihydroisoxazol-5-yl)-N-(2,3-dihydro-1H-inden-2-yl)pyrimidin-2-amine (L24)

After 1,1-Dibromoformaldoxime (0.960 g, 6.742 mmol) was dissolved in DMF (7 mL) and cooled to −10° C., a solution of imL24-1 (0.8 g, 3.371 mmol) and KHCO$_3$ (0.843 g, 8.428 mmol) in H$_2$O (7 mL) was slowly added dropwise to the reaction mixture and stirred at room temperature for 1 h. After confirming the completion of the reaction by TLC, the reaction mixture was extracted with EtOAc (3 times) and the organic layer was washed with brine and dried over MgSO$_4$. After filtration and concentration, the obtained residue was adsorbed onto silica gel and purified by silica gel column chromatography (25% EA in Hexane) to give the subject compound (L24) as a yellow solid (0.905 g, Yield: 74.8%).

$^1$H NMR (400 MHz, CDCl$_3$): δ 8.28 (s, 2H), 7.25-7.16 (m, 4H), 5.56-5.51 (m, 1H), 4.84-4.77 (m, 1H), 3.60-3.52 (m, 1H), 3.44-3.34 (m, 2H), 3.21 (dd, J=17.3, 9.4 Hz, 1H), 2.92-2.83 (m, 2H); LCMS m/z 360 [M+H]$^+$

Step 3: Synthesis of N-indan-2-yl-5-[3-[4-(1H-triazol-5-yl)-1-piperidyl]-4,5-dihydroisoxazol-5-yl]pyrimidin-2-amine (35)

5-(3-bromo-4,5-dihydroisoxazol-5-yl)-N-(2,3-dihydro-1H-inden-2-yl)pyrimidin-2-amine (L24) (20 mg, 0.0557 mmol), 4-(1H-1,2,3-triazol-5-yl)piperidine·HCl (3) (12.6 mg, 0.0668 mmol) and Na$_2$CO$_3$ (14.8 mg, 0.139 mmol) were dissolved in t-BuOH 1 mL, then reacted in a microwave reactor for 1 h. After confirming the completion of the reaction by TLC, it was filtered and washed with a solution of 10% MeOH in DCM. The residue obtained by concentrating the filtrate was adsorbed onto silica gel and purified by silica gel column chromatography (5% MeOH in DCM) to give the subject compound (35) as a yellow solid (10.8 mg, Yield:45.1%).

$^1$H NMR (400 MHz, CDCl$_3$): δ 8.31 (s, 2H), 7.65 (s, 1H), 7.58 (d, J=7.0 Hz, 1H), 7.15 (td, J=8.3, 3.2 Hz, 4H), 5.25 (t, J=9.4 Hz, 1H), 4.62-4.55 (m, 1H), 3.59 (d, J=14.2 Hz, 2H), 3.25-3.10 (m, 4H), 2.99-2.81 (m, 5H), 1.91 (d, J=14.6 Hz, 2H), 1.62 (d, J=9.0 Hz, 2H); LCMS m/z 431 [M+H]$^+$

[Example 36] Synthesis of 5-(3-(4-(1H-1,2,3-triazol-5-yl)piperidin-1-yl)isoxazol-5-yl)-N-(2,3-dihydro-1H-inden-2-yl)pyrimidin-2-amine N-indan-2-yl-5-[3-[4-(1H-triazol-5-yl)-1-piperidyl]-4,5-dihydroisoxazol-5-yl]pyrimidin-2-amine (35) (29.8 mg, 0.0692 mmol), I$_2$ (26.3 mg, 0.104 mmol) and imidazole (14.1 mg, 0.208 mmol) were dissolved in toluene (3 mL) and stirred at 110° C. for 2 h. After cooling to room temperature, it was diluted with EA, 10% Na$_2$S$_2$O$_4$ was added, and stirred for 10 minutes. 1N NaOH was added to the reaction mixture to adjust the pH to 8-10, and the reaction mixture was extracted with EA. The organic layer was washed with brine, dried over MgSO$_4$, filtered and concentrated. The obtained residue was adsorbed onto silica gel and purified by silica gel column chromatography (2% MeOH in DCM) to give the subject compound (36) as a white solid (12.8 mg, Yield:44.3%).

$^1$H NMR (400 MHz, DMSO-d6): δ 8.68 (s, 2H), 8.12 (d, J=6.3 Hz, 1H), 7.22-7.10 (m, 4H), 6.73 (s, 1H), 4.66 (d, J=6.8 Hz, 1H), 3.71 (d, J=13.0 Hz, 2H), 3.25 (dd, J=15.9, 7.6 Hz, 3H), 3.00 (d, J=12.1 Hz, 2H), 2.90 (dd, J=15.8, 7.0 Hz, 2H), 1.95 (s, 2H), 1.67 (d, J=9.8 Hz, 2H); LCMS m/z 429 [M+H]$^+$

[Example 37] Synthesis of N-(5,6-difluoroindan-2-yl)-5-[3-[4-(1H-triazol-5-yl)-1-piperidyl]-4,5-dihydroisoxazol-5-yl]pyrimidin-2-amine The subject compound was synthesized according to the same procedure as in Example 35, except for the use of 5,6-difluoro-2,3-dihydro-1H-inden-2-amine (4e) instead of 2-aminoindane (7.3 mg, Yield: 30.9%).

$^1$H NMR (400 MHz, DMSO-d6): δ 8.31 (s, 1H), 7.66-7.60 (m, 2H), 7.25 (t, J=9.2 Hz, 2H), 5.26 (t, J=9.2 Hz, 1H), 4.61 (dd, J=14.0, 7.3 Hz, 1H), 3.59 (d, J=13.2 Hz, 2H), 3.20 (dd, J=15.9, 7.3 Hz, 2H), 3.17-3.09 (m, 2H), 2.98-2.88 (m, 3H), 2.83 (dd, J=15.9, 6.8 Hz, 2H), 1.91 (d, J=11.7 Hz, 2H), 1.62 (d, J=13.4 Hz, 2H); LCMS m/z 467 [M+H]$^+$

[Example 38] Synthesis of 5-(3-(4-(1H-1,2,3-triazol-5-yl)piperidin-1-yl)isoxazol-5-yl)-N-(5,6-difluoro-2,3-dihydro-1H-inden-2-yl)pyrimidin-2-amine The subject compound was synthesized according to the same procedure as in Example 36, except for the use of N-(5,6-difluoroindan-2-yl)-5-[3-[4-(1H-triazol-5-yl)-1-piperidyl]-4,5-dihydroisoxazol-5-yl]pyrimidine-2-amine (Example 37) instead of N-indan-2-yl-5-[3-[4-(1H-triazol-5-yl)-1-piperidyl]-4,5-dihydroisoxazol-5-yl]pyrimidine-2-amine (35) (9.2 mg, Yield:71.6%).

$^1$H NMR (400 MHz, DMSO-d6): δ 8.67 (s, 1H), 8.13 (d, J=6.7 Hz, 1H), 7.64 (d, J=23.5 Hz, 1H), 7.27 (t, J=9.2 Hz, 2H), 6.73 (s, 1H), 4.68 (dd, J=13.8, 6.9 Hz, 1H), 3.71 (d, J=12.9 Hz, 2H), 3.24 (dd, J=16.2, 7.5 Hz, 2H), 3.02-2.94 (m, 2H), 2.87 (dd, J=16.2, 6.5 Hz, 2H), 1.97 (d, J=12.5 Hz, 3H), 1.72-1.60 (m, 2H); LCMS m/z 465 [M+H]$^+$

[Example 39] Synthesis of 5-(3-(4-(1H-1,2,3-triazol-5-yl)piperidin-1-yl)-4,5-dihydroisoxazol-5-yl)-N-(5-fluoro-2,3-dihydro-1H-inden-2-yl)pyrimidin-2-amine The subject compound was synthesized according to the same procedure as in Example 35, except for the use of 5-fluoro-2,3-dihydro-1H-inden-2-amine (4b) instead of 2-aminoindane (3.1 mg, Yield:17.5%).

$^1$H NMR (400 MHz, CDCl$_3$): δ 8.35 (s, 2H), 7.53 (s, 1H), 7.11-7.19 (m, 1H), 6.82-6.97 (m, 2H), 5.49 (d, J=6.8 Hz, 1H), 5.40 (t, J=8.9 Hz, 1H), 4.87-4.77 (m, 1H), 3.73 (dd, J=13.2, 3.1 Hz, 2H), 3.36 (m, 3H), 3.11-2.93 (m, 4H), 2.84 (td, J=15.6, 5.1 Hz, 2H), 2.02-2.08 (m, 2H), 1.75-1.85 (m, 2H); LCMS m/z 449 [M+H]$^+$

[Example 40] Synthesis of 5-(3-(4-(1H-1,2,3-triazol-5-yl)piperidin-1-yl)isoxazol-5-yl)-N-(5-fluoro-2,3-dihydro-1H-inden-2-yl)pyrimidin-2-amine The subject compound was synthesized according to the same procedure as in Example 36, except for the use of 5-(3-(4-(1H-1,2,3-triazol-5-yl)piperidine-1-yl)-4,5-dihydroisoxazol-5-yl)-N-(5-fluoro-2,3-dihydro-1H-inden-2-yl)pyrimidine-2-amine (Example 39) instead of N-indan-2-yl-5-[3-[4-(1H-triazol-5-yl)-1-piperidyl]-4,5-dihydroisoxazol-5-yl]pyrimidine-2-amine (35) (20.3 mg, Yield: 58%).

$^1$H NMR (400 MHz, DMSO-d6): δ 8.65 (s, 2H), 8.02 (d, J=6.7 Hz, 1H), 7.57 (s, 1H), 7.16-7.23 (m, 1H), 6.97 (d, J=8.3 Hz, 1H), 6.89 (t, J=8.7 Hz, 1H), 6.60 (s, 1H), 4.81-4.66 (m, 1H), 3.78 (d, J=12.8 Hz, 2H), 3.42-3.21 (m, 3H), 2.96 (m, 2H), 2.02 (d, J=10.9 Hz, 2H), 1.75 (m, 2H); LCMS m/z 447 [M+H]$^+$

[Example 41] Synthesis of N-[(3,5-difluorophenyl)methyl]-5-[3-[4-(1H-triazol-5-yl)-1-piperidyl]-4,5-dihydroisoxazol-5-yl]pyrimidin-2-amine The subject compound was synthesized according to the same procedure as in Example 35, except for the use of (3,5-difluorophenyl)methanamine instead of 2-aminoindane (8.3 mg, Yield: 18.2%).

$^1$H NMR (400 MHz, DMSO-d6): δ 8.30 (s, 2H), 7.89 (t, J=6.5 Hz, 1H), 7.65 (bs, 1H), 7.04 (t, J=9.6 Hz, 1H), 6.97 (d, J=6.7 Hz, 2H), 5.24 (t, J=9.1 Hz, 1H), 4.49 (d, J=6.2 Hz, 2H), 3.57 (d, J=12.8 Hz, 2H), 3.13 (dd, J=15.9, 9.3 Hz, 2H), 2.96-2.87 (m, 3H), 1.90 (d, J=12.6 Hz, 2H), 1.61 (dd, J=23.3, 14.4 Hz, 2H); LCMS m/z 441 [M+H]$^+$

[Example 42] Synthesis of N-benzyl-5-[3-[4-(1H-triazol-5-yl)-1-piperidyl]-4,5-dihydroisoxazol-5-yl]pyrimidin-2-amine The subject compound was synthesized according to the same procedure as in Example 35, except for the use of phenylmethanamine instead of 2-aminoindane (6.2 mg, Yield: 12.8%).

$^1$H NMR (400 MHz, DMSO-d6): δ 8.28 (s, 2H), 7.82 (t, J=6.4 Hz, 1H), 7.64 (bs, 1H), 7.27 (d, J=4.3 Hz, 4H), 7.19 (dd, J=8.5, 4.2 Hz, 1H), 5.23 (t, J=9.4 Hz, 1H), 4.48 (d, J=6.4 Hz, 2H), 3.57 (d, J=12.9 Hz, 2H), 3.12 (dd, J=15.9, 9.2 Hz, 2H), 2.97-2.86 (m, 3H), 1.90 (d, J=11.6 Hz, 2H), 1.61 (dd, J=21.2, 11.8 Hz, 2H); LCMS m/z 405 [M+H]$^+$

[Example 43] Synthesis of N-[(3,4-difluorophenyl)methyl]-5-[3-[4-(1H-triazol-5-yl)-1-piperidyl]-4,5-dihydroisoxazol-5-yl]pyrimidin-2-amine The subject compound was synthesized according to the same procedure as in Example 35, except for the use of (3,4-difluorophenyl)methanamine instead of 2-aminoindane (9.7 mg, Yield: 20.3%).

$^1$H NMR (400 MHz, DMSO-d6): δ 8.29 (s, 2H), 7.85 (t, J=6.3 Hz, 1H), 7.64 (s, 1H), 7.32 (dt, J=17.3, 7.3 Hz, 2H), 7.12 (s, 1H), 5.24 (t, J=9.2 Hz, 1H), 4.45 (d, J=6.1 Hz, 2H), 3.57 (d, J=12.7 Hz, 2H), 3.12 (dd, J=15.6, 9.4 Hz, 2H), 2.91 (dd, J=24.4, 11.8 Hz, 3H), 1.90 (d, J=12.0 Hz, 2H), 1.61 (dd, J=20.6, 10.6 Hz, 2H); LCMS m/z 441 [M+H]$^+$

[Example 44] Synthesis of 5-(3-(4-(1H-1,2,3-triazol-5-yl)piperidin-1-yl)-4,5-dihydroisoxazol-5-yl)-N-(3,5-dichlorobenzyl)pyrimidin-2-amine The subject compound was synthesized according to the same procedure as in Example 35, except for the use of (3,5-dichlorophenyl)methanamine instead of 2-aminoindane (4.8 mg, Yield: 10.2%).

$^1$H NMR (400 MHz, DMSO-d6): δ 8.30 (s, 2H), 7.90 (t, J=6.4 Hz, 1H), 7.62 (bs, 1H), 7.43 (s, 1H), 7.32 (s, 2H), 5.24 (t, J=9.2 Hz, 1H), 4.48 (d, J=6.4 Hz, 2H), 4.09 (dd, J=10.5, 5.2 Hz, 1H), 3.57 (d, J=12.8 Hz, 2H), 3.15 (d, J=5.3 Hz, 2H), 2.96-2.88 (m, 2H), 1.90 (d, J=10.3 Hz, 2H), 1.66-1.56 (m, 2H); LCMS m/z 474 [M+H]$^+$

[Example 45] Synthesis of 5-(3-(4-(1H-1,2,3-triazol-5-yl)piperidin-1-yl)-4,5-dihydroisoxazol-5-yl)-N-(benzo[d][1,3]dioxol-5-ylmethyl)pyrimidin-2-amine The subject compound was synthesized according to the same procedure as in Example 35, except for the use of benzo[d][1,3]dioxol-5-ylmethanamine instead of 2-aminoindane (5.1 mg, Yield: 10.7%).

$^1$H NMR (400 MHz, DMSO-d6): δ 8.28 (s, 2H), 7.76 (t, J=6.2 Hz, 1H), 7.62 (bs, 1H), 6.85-6.78 (m, 2H), 6.75 (d, J=7.7 Hz, 1H), 5.94 (s, 2H), 5.23 (t, J=9.0 Hz, 1H), 4.37 (d, J=6.1 Hz, 2H), 3.57 (d, J=12.8 Hz, 2H), 3.12 (dd, J=15.9, 9.3 Hz, 2H), 2.96-2.88 (m, 3H), 1.90 (d, J=12.8 Hz, 2H), 1.61 (dd, J=19.9, 10.1 Hz, 2H); LCMS m/z 449 [M+H]$^+$

[Example 46] Synthesis of N-(1,3-benzodioxol-5-ylmethyl)-5-[3-[4-(1H-triazol-5-yl)-1-piperidyl]isoxazol-5-yl]pyrimidin-2-amine The subject compound was synthesized according to the same procedure as in Example 36, except for the use of 5-(3-(4-(1H-1,2,3-triazol-5-yl)piperidine-1-yl)-4,5-dihydroisoxazol-5-yl)-N-(benzo[d][1,3]dioxol-5-ylmethyl)pyrimidine-2-amine (Example 45) instead of N-indan-2-yl-5-[3-[4-(1H-triazol-5-yl)-1-piperidyl]-4,5-dihydroisoxazol-5-yl]pyrimidine-2-amine (35) (3.4 mg, Yield: 21%).

$^1$H NMR (400 MHz, DMSO-d6): δ 8.64 (s, 2H), 8.25 (t, J=5.9 Hz, 1H), 6.87-6.80 (m, 2H), 6.77 (d, J=8.3 Hz, 1H), 6.71 (s, 1H), 5.95 (s, 2H), 4.43 (d, J=6.5 Hz, 2H), 3.70 (d,

J=12.5 Hz, 2H), 3.48 (s, 1H), 3.02-2.93 (m, 3H), 1.96 (d, J=9.8 Hz, 2H), 1.66 (dd, J=20.8, 12.7 Hz, 2H); LCMS m/z 447 [M+H]$^+$

[Example 47] Synthesis of 5-(3-(4-(1H-1,2,3-triazol-5-yl)piperidin-1-yl)-4,5-dihydroisoxazol-5-yl)-N-(3,5-dichlorophenethyl)pyrimidin-2-amine The subject compound was synthesized according to the same procedure as in Example 35, except for the use of 2-(3,5-dichlorophenyl)ethan-1-amine instead of 2-aminoindane (5.8 mg, Yield: 12.4%).
$^1$H NMR (400 MHz, DMSO-d6): δ 8.28 (s, 2H), 7.99 (s, 1H), 7.40 (s, 1H), 7.35 (s, 1H), 7.29 (s, 2H), 5.24 (t, J=9.4 Hz, 1H), 3.49 (dd, J=12.0, 6.3 Hz, 4H), 3.17-3.11 (m, 2H), 2.95 (d, J=12.9 Hz, 2H), 2.83 (t, J=6.6 Hz, 2H), 1.91 (d, J=17.4 Hz, 3H), 1.62 (d, J=10.8 Hz, 2H); LCMS m/z 487 [M+H]$^+$

[Example 48] Synthesis of 5-(3-(4-(1H-1,2,3-triazol-5-yl)piperidin-1-yl)-4,5-dihydroisoxazol-5-yl)-N-(3-(methylsulfonyl)benzyl)pyrimidin-2-amine The subject compound was synthesized according to the same procedure as in Example 35, except for the use of (3-(methylsulfonyl)phenyl)methanamine instead of 2-aminoindane (15.3 mg, Yield: 32.6%).
$^1$H NMR (400 MHz, DMSO-d6): δ 8.30 (s, 2H), 7.96 (t, J=6.5 Hz, 1H), 7.85 (s, 1H), 7.76 (d, J=7.5 Hz, 1H), 7.63 (d, J=8.1 Hz, 2H), 7.57 (d, J=7.6 Hz, 1H), 5.24 (t, J=9.2 Hz, 1H), 4.58 (d, J=6.1 Hz, 2H), 3.57 (d, J=12.8 Hz, 2H), 3.31 (dd, J=15.6, 9.1 Hz, 1H), 3.17 (s, 3H), 2.91 (dd, J=22.5, 10.5 Hz, 4H), 1.90 (d, J=11.3 Hz, 2H), 1.61 (dd, J=23.4, 13.5 Hz, 2H); LCMS m/z 483 [M+H]$^+$

[Example 49] Synthesis of 5-(3-(4-(1H-1,2,3-triazol-5-yl)piperidin-1-yl)-4,5-dihydroisoxazol-5-yl)-N-(4-(methylsulfonyl)benzyl)pyrimidin-2-amine The subject compound was synthesized according to the same procedure as in Example 35, except for the use of (4-(methylsulfonyl)phenyl)methanamine instead of 2-aminoindane (13.2 mg, Yield: 28.1%).
$^1$H NMR (400 MHz, DMSO-d6): δ 8.29 (s, 2H), 7.97 (dd, J=9.6, 3.2 Hz, 1H), 7.83 (d, J=8.3 Hz, 2H), 7.63 (bs, 1H), 7.52 (d, J=8.2 Hz, 2H), 5.23 (t, J=9.2 Hz, 1H), 4.61-4.54 (m, 2H), 3.57 (d, J=12.8 Hz, 2H), 3.31 (dd, J=15.9, 9.3 Hz, 2H), 3.15 (d, J=2.1 Hz, 3H), 3.13-3.08 (m, 1H), 2.96-2.88 (m, 2H), 1.90 (d, J=12.3 Hz, 2H), 1.61 (dd, J=21.0, 12.2 Hz, 2H); LCMS m/z 483 [M+H]$^+$

[Example 50] Synthesis of 5-(3-(4-(1H-tetrazol-5-yl)piperidin-1-yl)-4,5-dihydroisoxazol-5-yl)-N-(2,3-dihydro-1H-inden-2-yl)pyrimidin-2-amine The subject compound was synthesized according to the same procedure as in Example 35, except for the use of 4-(1H-tetrazol-5-yl)piperidine trifluoroacetic acid salt (im25) instead of 4-(1H-1,2,3-triazol-5-yl)piperidine·HCl (3) (15.7 mg, Yield: 65.4%).
$^1$H NMR (400 MHz, DMSO-d6): δ 8.31 (s, 2H), 7.59 (d, J=6.5 Hz, 1H), 7.15 (d, J=20.3 Hz, 4H), 5.26 (t, J=9.6 Hz, 1H), 4.62-4.57 (m, 1H), 4.08 (s, 1H), 3.59 (d, J=12.9 Hz, 1H), 3.20 (dd, J=14.3, 6.8 Hz, 2H), 3.15 (s, 2H), 3.02-2.93 (m, 2H), 2.89-2.82 (m, 2H), 1.95 (t, J=11.6 Hz, 2H), 1.74 (d, J=13.6 Hz, 2H); LCMS m/z 432 [M+H]$^+$

[Example 51] Synthesis of 5-(3-(4-(5-(Difluoromethyl)-1,3,4-oxadiazol-2-yl)piperidin-1-yl)-4,5-dihydroisoxazol-5-yl)-N-(2,3-dihydro-1H-inden-2-yl)pyrimidin-2-amine The subject compound was synthesized according to the same procedure as in Example 35, except for the use of 2-(difluoromethyl)-5-(piperidine-4-yl)-1,3,4-oxadiazole (im20) instead of 4-(1H-1,2,3-triazol-5-yl)piperidine·HCl (3) (3.7 mg, Yield: 13.8%).
$^1$H NMR (400 MHz, DMSO-d6): δ 8.31 (s, 1H), 7.59 (t J=134.0 Hz, 1H), 7.59 (J=6.6 Hz, 1H), 7.20-7.10 (m, 4H), 5.26 (t, J=9.4 Hz, 1H), 4.59 (d, J=7.1 Hz, 1H), 3.58 (d, J=13.1 Hz, 2H), 3.26-3.11 (m, 5H), 3.05-2.95 (m, 2H), 2.86 (dd, J=15.7, 6.6 Hz, 2H), 2.01 (dd, J=25.3, 16.9 Hz, 3H), 1.77 (d, J=9.4 Hz, 1H); LCMS m/z 482 [M+H]$^+$

[Example 52] Synthesis of 5-(3-(4-(1H-tetrazol-5-yl)piperidin-1-yl)-4,5-dihydroisoxazol-5-yl)-N-(5,6-difluoro-2,3-dihydro-1H-inden-2-yl)pyrimidin-2-amine The subject compound was synthesized according to the same procedure as in Example 35, except for the use of 5,6-difluoro-2,3-dihydro-1H-inden-2-amine (4e) instead of 2-aminoindane in Step 1, and the use of 4-(1H-tetrazol-5-yl)piperidine trifluoroacetic acid salt (im25) instead of 4-(1H-1,2,3-triazol-5-yl)piperidine·HCl (3) in Step 3 (18.7 mg, Yield: 79%).
$^1$H NMR (400 MHz, DMSO-d6): δ 8.32 (s, 2H), 7.62 (d, J=6.5 Hz, 1H), 7.25 (t, J=9.5 Hz, 2H), 5.26 (t, J=9.4 Hz, 1H), 4.61 (d, J=6.9 Hz, 1H), 3.59 (d, J=12.8 Hz, 2H), 3.20 (dd, J=16.2, 7.8 Hz, 5H), 3.01-2.93 (m, 2H), 2.83 (dd, J=15.8, 7.0 Hz, 2H), 1.98-1.91 (m, 2H), 1.73 (dd, J=22.3, 13.3 Hz, 2H); LCMS m/z 468 [M+H]$^+$

[Example 53] Synthesis of N-(5-fluoro-2,3-dihydro-1H-inden-2-yl)-5-(3-(4-(5-(trifluoromethyl)-1,3,4-oxadiazol-2-yl)piperidin-1-yl)-4,5-dihydroisoxazol-5-yl)pyrimidin-2-amine Step 1: Synthesis of 5-(3-(4-(1H-tetrazol-5-yl)piperidin-1-yl)-4,5-dihydroisoxazol-5-yl)-N-(5-fluoro-2,3-dihydro-1H-inden-2-yl)pyrimidin-2-amine The subject compound was synthesized according to the same procedure as in Example 35, except for the use of 5-fluoro-2,3-dihydro-1H-inden-2-amine (4b) instead of 2-aminoindane in Step 1, and the use of 4-(1H-tetrazol-5-yl)piperidine trifluoroacetic acid salt (im25) instead of 4-(1H-1,2,3-triazol-5-yl)piperidine·HCl (3) in Step 3 (15.4 mg, Yield: 46%).
LCMS m/z 450 [M+H]$^+$ Step 2: Synthesis of N-(5-fluoro-2,3-dihydro-1H-inden-2-yl)-5-(3-(4-(5-(trifluoromethyl)-1,3,4-oxadiazol-2-yl)piperidin-1-yl)-4,5-dihydroisoxazol-5-yl)pyrimidin-2-amine 5-(3-(4-(1H-tetrazol-5-yl)piperidin-1-yl)-4,5-dihydroisoxazol-5-yl)-N-(5-fluoro-2,3-dihydro-1H-inden-2-yl)pyrimidin-2-amine (9.3 mg, 0.021 mmol) was dissolved in DCM, then trifluoroacetic anhydride (6.5 mg, 0.031 mmol) was added dropwise at 0° C. The temperature was raised to room temperature, and the mixture was stirred overnight. Trifluoroacetic anhydride (0.1 ml) was added, and the mixture was stirred for an additional 2 h, then the reaction mixture was extracted with DCM, and the organic layer was washed with saturated aqueous NaHCO$_3$ solution, water, and brine. After drying over MgSO$_4$, filtering and concentrating, the obtained residue was purified by Prep-TLC (5% MeOH in DCM) to give the subject compound (0.5 mg, Yield: 4.7%).

$^1$H NMR (400 MHz, CDCl$_3$): δ 8.33 (s, 2H), 7.15 (m, 1H), 6.97-6.81 (m, 2H), 5.42 (m, 2H), 4.81 (m, 1H), 3.73 (d, J=13.6 Hz, 2H), 3.35 (s, J=6 Hz, 2H), 3.22 (m, 1H), 3.13-2.94 (m, 4H), 2.84 (td, J=16.2, 5.5 Hz, 2H), 2.27-2.14 (m, 2H), 2.08-1.92 (m, 2H); LCMS m/z 518 [M+H]$^+$

[Example 54] Synthesis of N-(5,6-difluoro-2,3-dihydro-1H-inden-2-yl)-5-(5-(2-methyl-4-(1H-1,2,3-triazol-5-yl)piperidin-1-yl)-1,3,4-oxadiazol-2-yl)pyrimidin-2-amine The subject compound was synthesized according to the same procedure as in Example 11, except for the use of 7e instead of 7d (Yield: 8%).

$^1$H NMR (400 MHz, Chloroform-d) δ 8.79 (s, 2H), 7.54 (s, 1H), 7.51 (s, 1H), 7.03 (t, J=8.8 Hz, 2H), 5.68 (d, J=7.6 Hz, 1H), 4.94-4.84 (m, 1H), 4.60-4.47 (m, 1H), 4.04 (dd, J=13.4, 3.1 Hz, 1H), 3.41-3.34 (m, 3H), 3.31-3.24 (m, 1H), 2.86 (dd, J=16.0, 5.3 Hz, 2H), 2.03 (d, J=4.4 Hz, 2H), 1.81 (dd, J=12.9, 4.8 Hz, 1H), 1.40 (d, J=6.9 Hz, 3H); MS (ESI, m/z) calculated for C$_{23}$H$_{24}$F2N$_9$O [M+H]$^+$ 480.21, found 480.15.

[Example 55] Synthesis of 5-(5-(4-(1H-1,2,3-triazol-5-yl)piperidin-1-yl)-1,3,4-oxadiazol-2-yl)-N-(benzo[d][1,3]dioxol-5-ylmethyl)pyrimidin-2-amine The subject compound was synthesized according to the same procedure as in Example 1, except for the use of benzo[d][1,3]dioxol-5-ylmethanamine instead of 2,3-dihydro-1H-inden-2-amine (Yield: 46%).

$^1$H NMR (400 MHz, CDCl$_3$) δ 12.36 (s, 1H), 8.79 (s, 2H), 7.54 (s, 1H), 6.86-6.75 (m, 3H), 5.95 (s, 2H), 4.60 (d, J=5.9 Hz, 2H), 4.14 (dt, J=13.6, 3.7 Hz, 2H), 3.27 (ddd, J=13.2, 11.8, 2.9 Hz, 2H), 3.06 (tt, J=11.4, 3.7 Hz, 1H), 2.19-2.13 (m, 2H), 1.95-1.84 (m, 2H); $^{13}$C NMR (100 MHz, CDCl$_3$) δ 163.93, 162.18, 156.08, 155.79, 150.40, 147.95, 147.03, 132.12, 130.02, 120.89, 109.48, 108.36, 108.25, 101.10, 46.34, 45.42, 32.56, 30.65; HRMS (ESI, m/z) calculated for C$_{21}$H$_{22}$N$_9$O$_3$ [M+H]$^+$ 448.1840, found 448.1841.

[Example 56] Synthesis of 5-(5-(4-(1H-1,2,3-triazol-5-yl)piperidin-1-yl)-1,3,4-oxadiazol-2-yl)-N-(3,4-dichlorobenzyl)pyrimidin-2-amine The subject compound was synthesized according to the same procedure as in Example 1, except for the use of (3,4-dichlorophenyl)methanamine instead of 2,3-dihydro-1H-inden-2-amine (Yield: 36%).

$^1$H NMR (400 MHz, CDCl$_3$) δ 8.80 (s, 2H), 7.54 (s, 1H), 7.47-7.38 (m, 2H), 7.21-7.17 (m, 1H), 5.88 (t, J=6.2 Hz, 1H), 4.67 (d, J=6.3 Hz, 2H), 4.20-4.11 (m, 2H), 3.33-3.20 (m, 2H), 3.12-3.00 (m, 1H), 2.20-2.13 (m, 2H), 1.94-1.84 (m, 2H); HRMS (ESI, m/z) calculated for C$_{20}$H$_{20}$Cl$_2$N$_9$O [M+H]$^+$ 472.1162, found 472.1162.

[Example 57] Synthesis of 5-(5-(4-(1H-1,2,3-triazol-5-yl)piperidin-1-yl)-1,3,4-oxadiazol-2-yl)-N-(3,5-difluorobenzyl)pyrimidin-2-amine The subject compound was synthesized according to the same procedure as in Example 1, except for the use of (3,4-difluorophenyl)methanamine instead of 2,3-dihydro-1H-inden-2-amine (Yield: 40%).

$^1$H NMR (400 MHz, CD$_3$OD) δ 8.78 (s, 2H), 7.52 (s, 1H), 6.92-6.87 (m, 2H), 6.71 (tt, J=8.9, 2.3 Hz, 1H), 4.67 (s, 2H), 4.14-4.09 (m, 2H), 3.29 (ddd, J=13.2, 11.9, 2.9 Hz, 2H), 3.07 (tt, J=11.5, 3.6 Hz, 1H), 2.20-2.14 (m, 2H), 1.92-1.82 (m, 2H); $^{13}$C NMR (100 MHz, CD$_3$OD) δ 163.99, 163.39 (q, J=12.8 Hz), 162.41, 156.13, 156.05, 149.06, 143.21, 128.77-127.05 (m), 110.17 (dd, J=11.9, 7.0 Hz), 102.74 (t, J=25.4 Hz), 46.45, 44.57 (d, J=2.3 Hz), 32.49, 30.86; HRMS (ESI, m/z) calculated for C$_{20}$H$_{20}$F$_2$N$_9$O [M+H]$^+$ 440.1753, found 440.1755.

[Example 58] Synthesis of 5-(5-(4-(1H-1,2,3-triazol-5-yl)piperidin-1-yl)-1,3,4-oxadiazol-2-yl)-N-(3,4-difluorobenzyl)pyrimidin-2-amine The subject compound was synthesized according to the same procedure as in Example 1, except for the use of (3,4-difluorophenyl)methanamine instead of 2,3-dihydro-1H-inden-2-amine (Yield: 43.4%).

$^1$H NMR (400 MHz, CD$_3$OD) δ 8.77 (s, 2H), 7.51 (s, 1H), 7.22-7.07 (m, 3H), 4.64 (s, 2H), 4.12 (dt, J=13.3, 3.5 Hz, 2H), 3.32-3.25 (m, 2H), 3.07 (ddt, J=11.5, 7.8, 3.7 Hz, 1H), 2.20-2.14 (m, 2H), 1.87 (td, J=12.0, 7.8 Hz, 2H); $^{13}$C NMR (100 MHz, CD$_3$OD) δ 163.96, 162.32, 156.11, 156.00, 151.38 (dd, J=74.0, 12.7 Hz), 149.02, 148.91 (dd, J=60.1, 12.7 Hz), 135.93 (dd, J=5.2, 3.7 Hz), 127.67, 123.55 (dd, J=6.3, 3.6 Hz), 117.00 (dd, J=90.3, 17.4 Hz), 109.33, 46.43, 44.37 (d, J=1.5 Hz), 32.47, 30.83; HRMS (ESI, m/z) calculated for C$_{20}$H$_{20}$F$_2$N$_9$O$^+$ [M+H]$^+$ 440.1753, found 440.1754.

[Example 59] Synthesis of 5-(5-(4-(1H-1,2,3-triazol-5-yl)piperidin-1-yl)-1,3,4-oxadiazol-2-yl)-N-(3,5-dibromobenzyl)pyrimidin-2-amine The subject compound was synthesized according to the same procedure as in Example 1, except for the use of (3,5-dibromophenyl)methanamine instead of 2,3-dihydro-1H-inden-2-amine (Yield: 31.7%).

$^1$H NMR (400 MHz, CD$_3$OD) δ 8.78 (s, 2H), 7.57 (t, J=1.8 Hz, 1H), 7.52 (s, 1H), 7.45 (d, J=1.7 Hz, 2H), 4.64 (s, 2H), 4.15-4.07 (m, 2H), 3.32-3.22 (m, 2H), 3.12-3.01 (m, 1H), 2.20-2.13 (m, 2H), 1.92-1.82 (m, 2H); $^{13}$C NMR (100 MHz, CD$_3$OD) δ 163.99, 162.31, 156.12, 156.05, 149.16, 143.10, 133.05, 129.37, 127.61, 123.22, 109.49, 46.45, 44.25, 32.48, 30.85; HRMS (ESI, m/z) calculated for C$_{20}$H$_{20}$Br$_2$N$_9$O$^+$ [M+H]$^+$ 560.0152, found 560.0132.

[Example 60] Synthesis of 5-(5-(4-(1H-1,2,3-triazol-5-yl)piperidin-1-yl)-1,3,4-oxadiazol-2-yl)-N-(5-bromo-2,3-dihydro-1H-inden-2-yl)-4-methylpyrimidin-2-amine The subject compound was synthesized according to the same procedure as in Example 1, except for the use of 5-bromo-2,3-dihydro-1H-inden-2-amine (4d) instead of 2,3-dihydro-1H-inden-2-amine, and the use of ethyl 2-chloro-4-methylpyrimidine-5-carboxylate instead of 2-chloropyrimidine-5-carboxylate (Yield: 52%).

$^1$H NMR (400 MHz, CD$_3$OD) δ 8.61 (s, 1H), 7.53 (s, 1H), 7.37 (d, J=1.8 Hz, 1H), 7.30 (dd, J=8.0, 1.9 Hz, 1H), 7.12 (d, J=8.0 Hz, 1H), 4.15-4.08 (m, 4H), 3.43-3.38 (m, 1H), 3.34-3.32 (m, 1H), 3.30-3.26 (m, 1H), 3.08 (tt, J=11.5, 3.7 Hz, 1H), 2.95-2.84 (m, 2H), 2.68 (s, 3H), 2.20-2.13 (m, 2H), 1.94-1.83 (m, 2H); $^{13}$C NMR (100 MHz, CD$_3$OD) δ 167.27, 163.85, 161.29, 157.08, 143.75, 140.30, 129.94, 128.07, 126.46, 120.51, 108.11, 52.82, 46.46, 39.90, 39.52, 32.52, 30.89, 24.59; HRMS (ESI, m/z) calculated for $C_{23}H_{25}BrN_9O$ [M+H]$^+$ 522.1360, found 522.1359.

[Example 61] Synthesis of 5-(5-(4-(1H-1,2,3-triazol-5-yl)piperidin-1-yl)-1,3,4-oxadiazol-2-yl)-N-(5,6-dibromo-2,3-dihydro-1H-inden-2-yl)-4-methylpyrimidin-2-amine The subject compound was synthesized according to the same procedure as in Example 1, except for the use of 5,6-dibromo-2,3-dihydro-1H-inden-2-amine instead of 2,3-dihydro-1H-inden-2-amine, and the use of ethyl 2-chloro-4-methylpyrimidine-5-carboxylate instead of 2-chloropyrimidine-5-carboxylate (Yield:50%).

$^1$H NMR (400 MHz, CDCl$_3$) δ 11.96 (s, 1H), 8.63 (s, 1H), 7.54 (s, 1H), 7.49 (s, 2H), 5.65 (d, J=7.5 Hz, 1H), 4.89 (d, J=6.6 Hz, 1H), 4.16-4.11 (m, 2H), 3.38-3.24 (m, 4H), 3.07 (ddt, J=11.5, 7.8, 3.7 Hz, 1H), 2.85 (dd, J=16.3, 5.4 Hz, 2H), 2.71 (s, 3H), 2.19-2.13 (m, 2H), 1.95-1.85 (m, 2H); MS (ESI, m/z) calculated for $C_{23}H_{24}BrN_9O$ [M+H]$^+$ 600.04, found 600.05.

[Example 62] Synthesis of 5-(3-(4-(1H-1,2,3-triazol-4-yl)piperidin-1-yl)propyl)-N-(2,3-dihydro-1H-inden-2-yl)pyrimidin-2-amine 1-(4-(1H-1,2,3-triazol-4-yl)piperidine-1-yl)-3-(2-((2,3-dihydro-1H-inden-2-yl)amino)pyrimidine-5-yl)propan-1-one (Example 17, 0.47 mmol) was dissolved in DMF and cooled to 0° C., then Lithium aluminum hydride (LiAl$_4$, 0.10 mmol) in ACN was slowly added dropwise. After the reaction mixture was stirred at room temperature for 2 h, the reaction was quenched with 1N HCl. The pH was adjusted to 7-8 with an aqueous Na$_2$CO$_3$ solution, and the mixture was extracted with diethyl ether. The organic layer was dried over Na$_2$SO$_4$, filtered, and concentrated. The obtained residue was purified by silica gel column chromatography (Ethyl acetate/Hexane) to give the subject compound (Yield: 45%).

$^1$H NMR (400 MHz, CD$_3$OD): δ 8.17 (s, 2H), 7.55 (s, 1H), 7.25-7.20 (m, 2H), 7.18-7.13 (m, 2H), 4.75-4.72 (m, 1H), 3.41-3.35 (m, 2H), 3.14-3.08 (m, 2H), 2.94-2.84 (m, 3H), 2.58-2.50 (m, 4H), 2.33 (t, J=11.7 Hz, 2H), 2.12-2.06 (m, 2H), 1.90-1.78 (m, 4H); $^{13}$C NMR (100 MHz, CD$_3$OD) δ 161.24, 158.39, 148.90, 141.74, 127.35, 127.10, 125.17, 123.42, 58.21, 53.74, 53.12, 40.38, 32.70, 31.52, 28.14, 27.70; MS (ESI, m/z) calculated for $C_{23}H_{30}N_7^+$ [M+H]$^+$ 404.26, found 404.30.

[Example 63] Synthesis of N-(5,6-difluoro-2,3-dihydro-1H-inden-2-yl)-5-(5-(4-morpholinopiperidin-1-yl)-1,3,4-oxadiazol-2-yl)pyrimidin-2-amine The subject compound was synthesized according to the same procedure as in Example 1, except for the use of 4-(piperidine-4-yl)morpholine instead of 4-(1H-1,2,3-triazol-5-yl)piperidine·HCl (3), as a white solid (14.8 mg, Yield: 33.8%).

$^1$H NMR (400 MHz, DMSO-d6): δ8.73 (s, 2H), 8.24 (d, J=6.5 Hz, 1H), 7.27 (t, J=9.3 Hz, 2H), 4.68 (dd, J=13.7, 7.0 Hz, 1H), 3.93 (d, J=13.0 Hz, 2H), 3.59-3.48 (m, 4H), 3.24 (dd, J=16.1, 7.6 Hz, 2H), 3.06 (t, J=11.4 Hz, 2H), 2.87 (dd, J=16.1, 6.5 Hz, 2H), 2.46-2.35 (m, 4H), 1.84 (d, J=11.0 Hz, 2H), 1.46 (ddd, J=16.3, 12.8, 4.8 Hz, 2H), 1.19-1.11 (m, 1H); LCMS m/z 484[M+H]$^+$

[Example 64] Synthesis of 1-(1-(5-(2-((5,6-Difluoro-2,3-dihydro-1H-inden-2-yl)amino)pyrimidin-5-yl)-1,3,4-oxadiazol-2-yl)piperidin-4-yl)azetidin-3-ol The subject compound was synthesized according to the same procedure as in Example 1, except for the use of 1-(piperidine-4-yl)azetidin-3-ol(1-(piperidin-4-yl)azetidin-3-ol) instead of 4-(1H-1,2,3-triazol-5-yl)piperidine·HCl (3), as an off-white solid (25.1 mg, Yield: 59%).

$^1$H NMR (400 MHz, DMSO-d6): δ8.73 (s, 2H), 8.23 (d, J=6.8 Hz, 1H), 7.27 (t, J=9.3 Hz, 2H), 5.31 (d, J=3.2 Hz, 1H), 4.68 (dd, J=14.0, 7.2 Hz, 1H), 4.23-3.99 (m, 2H), 3.74 (dd, J=7.7, 5.4 Hz, 2H), 3.52 (t, J=6.2 Hz, 2H), 3.30 (s, 2H), 3.23 (dd, J=16.1, 7.5 Hz, 2H), 3.19-3.12 (m, 2H), 2.87 (dd, J=15.9, 6.5 Hz, 2H), 2.74 (s, 1H), 2.25 (s, 1H), 1.71 (d, J=10.5 Hz, 2H), 1.23 (d, J=12.6 Hz, 2H); LCMS m/z 470[M+H]$^+$

[Example 65] Synthesis of 1-(5-(2-((5,6-Difluoro-2,3-dihydro-1H-inden-2-yl)amino)pyrimidin-5-yl)-1,3,4-oxadiazol-2-yl)piperidine-4-sulfonamide The subject compound was synthesized according to the same procedure as in Example 1, except for the use of piperidine-4-sulfonamide instead of 4-(1H-1,2,3-triazol-5-yl)piperidine·HCl (3), as a white solid (20.7 mg, Yield: 47.9%).

$^1$H NMR (400 MHz, DMSO-d6): δ8.76 (d, J=12.8 Hz, 2H), 8.26 (d, J=6.9 Hz, 1H), 7.27 (t, J=9.4 Hz, 2H), 6.82 (s, 2H), 4.68 (dd, J=14.1, 7.0 Hz, 1H), 4.04 (d, J=12.9 Hz, 2H), 3.24 (dd, J=16.1, 7.5 Hz, 2H), 3.13 (t, J=11.4 Hz, 3H), 2.87 (dd, J=16.0, 6.5 Hz, 2H), 2.08 (d, J=12.4 Hz, 2H), 1.64 (qd, J=12.6, 4.5 Hz, 2H); LCMS m/z 478[M+H]$^+$

[Example 66] Synthesis of 5-(1-(5-(2-((5,6-Difluoro-2,3-dihydro-1H-inden-2-yl)amino)pyrimidin-5-yl)-1,3,4-oxadiazol-2-yl)piperidin-4-yl)-1,3,4-oxadiazol-2(3H)-one The subject compound was synthesized according to the same procedure as in Example 1, except for the use of 5-(piperidine-4-yl)-1,3,4-oxadiazol-2(3H)-one instead of 4-(1H-1,2,3-triazol-5-yl)piperidine·HCl (3), as a white solid (10.9 mg, Yield: 24.9%).

$^1$H NMR (400 MHz, DMSO-d6): δ12.14 (s, 1H), 8.75 (d, J=9.9 Hz, 2H), 8.26 (d, J=4.1 Hz, 1H), 7.28 (t, J=8.8 Hz, 2H), 4.68 (d, J=4.9 Hz, 1H), 3.92 (d, J=13.0 Hz, 2H), 3.21 (t, J=12.3 Hz, 4H), 2.83 (dd, J=34.8, 13.5 Hz, 3H), 1.99 (d, J=11.4 Hz, 2H), 1.68 (dd, J=23.7, 12.3 Hz, 2H); LCMS m/z 483[M+H]$^+$

[Example 67] Synthesis of 1-(5-(2-((5,6-Difluoro-2,3-dihydro-1H-inden-2-yl)amino)pyrimidin-5-yl)-1,3,4-oxadiazol-2-yl)piperidine-4-carboxylic acid Step 1: Synthesis of Methyl piperidine-4-carboxylate trifluoroacetic acid salt (im29)

To a solution of methyl 1-(tert-butoxycarbonyl)-4-piperidinecarboxylate (0.2 g, 0.822 mmol) in DCM (8.2 mL) was added TFA (2.7 mL) at 0° C. and stirred at room temperature for 1 h. The reaction mixture was concentrated under reduced pressure to give the subject compound (im29) as a white solid (0.181 g, Yield: 91.5%), which was used in the following reaction without purification.

¹H NMR (400 MHz, DMSO-d6): δ8.43 (bs, 1H), 3.61 (s, 3H), 3.23 (d, J=12.9 Hz, 2H), 2.91 (td, J=12.6, 3.0 Hz, 2H), 2.66 (dd, J=12.9, 9.0 Hz, 1H), 1.96 (d, J=14.5 Hz, 2H), 1.67 (td, J=15.0, 4.0 Hz, 2H)

Step 2: Synthesis of Methyl 1-(5-(2-((5,6-difluoro-2,3-dihydro-1H-inden-2-yl)amino)pyrimidin-5-yl)-1,3,4-oxadiazol-2-yl)piperidine-4-carboxylate (L29)

To a solution of 7e (60 mg, 0.181 mmol) in DMF (0.9 mL) was added im29 (52.2 mg, 0.217 mmol) and cooled to 0° C. DIPEA (52 µL, 0.543 mmol) was added to the reaction mixture and stirred at the same temperature for another 30 minutes, then BOP reagent (96.1 mg, 0.217 mmol) was added and stirred at room temperature overnight. The reaction mixture was extracted with EA, the organic layer was washed with brine, dried over $Na_2SO_4$, filtered and concentrated. The obtained residue was purified by column chromatography (DCM/MeOH) to give the subject compound (L29) as a light yellow solid (60.6 mg, 73.3%).

¹H NMR (400 MHz, DMSO-d6): δ8.74 (s, 2H), 8.24 (d, J=6.5 Hz, 1H), 7.27 (t, J=9.3 Hz, 2H), 4.68 (dd, J=14.0, 6.8 Hz, 1H), 3.87 (d, J=13.0 Hz, 2H), 3.61 (s, 3H), 3.24 (dd, J=16.1, 7.4 Hz, 2H), 3.15 (t, J=11.0 Hz, 2H), 2.87 (dd, J=15.9, 6.5 Hz, 2H), 2.79 (d, J=10.7 Hz, 1H), 1.92 (d, J=10.6 Hz, 2H), 1.62 (dd, J=20.8, 11.1 Hz, 2H); LCMS m/z 457[M+H]⁺

Step 3: Synthesis of 1-(5-(2-((5,6-Difluoro-2,3-dihydro-1H-inden-2-yl)amino)pyrimidin-5-yl)-1,3,4-oxadiazol-2-yl)piperidine-4-carboxylic acid (67)

To a solution of L29 (10 mg, 0.022 mmol) in THF (0.1 mL) was added 1N NaOH (55 µL, 0.055 mmol) and stirred at room temperature overnight. 3N HCl was added to the reaction mixture to adjust the pH to 2~4, and the reaction mixture was extracted with EA. The organic layer was collected, washed with brine, dried over $Na_2SO_4$, filtered, and concentrated. The subject compound was obtained as a white solid (8.6 mg, 88.7%).

¹H NMR (400 MHz, DMSO-d6) δ12.30 (bs, 1H), 8.74 (s, 2H), 8.24 (d, J=6.8 Hz, 1H), 7.27 (t, J=9.3 Hz, 2H), 4.68 (dd, J=13.7, 6.9 Hz, 1H), 3.86 (d, J=12.9 Hz, 2H), 3.24 (dd, J=16.1, 7.6 Hz, 2H), 3.14 (t, J=11.0 Hz, 2H), 2.87 (dd, J=15.9, 6.4 Hz, 2H), 1.91 (d, J=13.5 Hz, 2H), 1.59 (d, J=9.4 Hz, 2H), 1.18 (d, J=24.2 Hz, 1H); LCMS m/z 443[M+H]⁺

[Example 68] Synthesis of 2-(1-(5-(2-((5,6-Difluoro-2,3-dihydro-1H-inden-2-yl)amino)pyrimidin-5-yl)-1,3,4-oxadiazol-2-yl)piperidin-4-yl)acetic acid The subject compound was synthesized according to the same procedure as in Example 67, except for the use of tert-butyl 4-(2-methoxy-2-oxoethyl)piperidine-1-carboxylate instead of methyl 1-(tert-butoxycarbonyl)-4-piperidinecarboxylate, as an off-white solid (5.6 mg, 38.5%).

[Example 69] Synthesis of 1-(5-(2-((5,6-Difluoro-2,3-dihydro-1H-inden-2-yl)amino)pyrimidin-5-yl)-1,3,4-oxadiazol-2-yl)-N-hydroxypiperidine-4-carboxamide To a solution of 1-(5-(2-((5,6-difluoro-2,3-dihydro-1H-inden-2-yl)amino)pyrimidine-5-yl)-1,3,4-oxadiazol-2-yl)piperidine-4-carboxylic acid (Example 67) (68 mg, 0.154 mmol) in THF (0.5 mL) was added CDI (37.4 mg, 0.231 mmol), stirred at room temperature for 1 h and then $NH_2OH$—HCl (21.4 mg, 0.307 mmol) was added and stirred overnight. The reaction mixture was extracted with EA, the organic layer was collected, washed with brine, dried over $MgSO_4$, filtered and concentrated. The obtained residue was purified by column chromatography (DCM/MeOH) to give the subject compound as a white solid (2.5 mg, 3.6%).

¹H NMR (400 MHz, DMSO-d6): δ10.49 (s, 1H), 8.74 (s, 2H), 8.24 (d, J=7.1 Hz, 1H), 7.27 (t, J=9.5 Hz, 2H), 4.68 (d, J=7.1 Hz, 1H), 3.94 (d, J=13.1 Hz, 2H), 3.26-3.21 (m, 2H), 3.12-3.01 (m, 2H), 2.88 (dd, J=15.1, 8.0 Hz, 2H), 2.19-2.13 (m, 1H), 1.68-1.61 (m, 2H), 0.83 (t, J=6.4 Hz, 2H); LCMS m/z 458[M+H]⁺

[Example 70] Synthesis of N-(5,6-difluoro-2,3-dihydro-1H-inden-2-yl)-5-(5-(4-methoxy-4-(1H-1,2,3-triazol-4-yl)piperidin-1-yl)-1,3,4-oxadiazol-2-yl)pyrimidin-2-amine (4-(1-(5-(2-((5,6-Difluoro-2,3-dihydro-1H-inden-2-yl)amino)pyrimidin-5-yl)-1,3,4-oxadiazol-2-yl)-4-fluoropiperidin-4-yl)-1H-1,2,3-triazol-1-yl)methyl pivalate (L30) was synthesized according to the same procedure as in Step 1-1 to Step 2-1 of Example 33, except for the use of tert-butyl 4-ethynyl-4-fluoropiperidine-1-carboxylate instead of tert-butyl 4-ethynylpiperidine-1-carboxylate (90 mg, Yield: 65%).

¹H NMR (400 MHz, DMSO-d6) δ 8.76 (s, 2H), 8.25 (d, J=6.7 Hz, 1H), 7.27 (t, J=9.3 Hz, 2H), 6.31 (s, 2H), 4.69 (dd, J=14.0, 7.1 Hz, 1H), 3.78 (m, 2H), 3.51 (m, 2H), 3.24 (dd, J=16.1, 7.5 Hz, 2H), 2.93-2.82 (m, 4H), 2.32 (m, 2H), 1.11 (s, 9H); LCMS m/z 598[M+H]⁺

To a solution of L30 (80 mg, 0.13 mmol) in MeOH (1 mL) was added $K_2CO_3$ (37 mg, 0.27 mmol) and stirred at room temperature overnight. The residue obtained by concentrating the reaction mixture was purified by column chromatography (DCM/MeOH) to give the subject compound (70) as a white solid (20 mg, Yield: 31%).

¹H NMR (400 MHz, DMSO-d6) δ 8.74 (s, 2H), 8.24 (d, J=6.7 Hz, 1H), 7.27 (t, J=9.3 Hz, 2H), 4.68 (dd, J=13.8, 6.8 Hz, 1H), 3.60 (s, 2H), 3.49 (m, 2H), 3.24 (dd, J=15.9, 7.5 Hz, 2H), 2.95 (s, 3H), 2.88 (dd, J=15.9, 6.6 Hz, 2H), 2.16 (m, 2H), 2.06 (m, 2H); LCMS m/z 496[M+H]⁺

[Example 71] Synthesis of N-(5,6-difluoro-2,3-dihydro-1H-inden-2-yl)-5-(5-(4-fluoro-4-(1H-1,2,3-triazol-5-yl)piperidin-1-yl)-1,3,4-oxadiazol-2-yl)pyrimidin-2-amine N-(5,6-difluoro-2,3-dihydro-1H-inden-2-yl)-5-(5-(4-ethynyl-4-fluoropiperidin-1-yl)-1,3,4-oxadiazol-2-yl)pyrimidine-2-amine (L31) was synthesized according to the same procedure as in Step 1 of Example 34, except for the use of 4-ethynyl-4-fluoropiperidine trifluoroacetic acid salt instead of 4-ethynylpiperidine trifluoroacetic acid salt (55 mg, Yield: 83%).

¹H NMR (400 MHz, DMSO-d6) δ 8.74 (s, 2H), 8.26 (d, J=6.7 Hz, 1H), 7.27 (t, J=9.3 Hz, 2H), 4.68 (m, 1H), 4.02 (d, J=5.2 Hz, 1H), 3.68-3.48 (m, 4H), 3.29-3.17 (m, 2H), 2.94-2.81 (m, 2H), 2.15-2.00 (m, 4H); LCMS m/z 441[M+H]⁺

L31 (50 mg, 0.11 mmol), trimethylsilyl azide (18 uL, 0.14 mmol) and copper (I) iodide (2.4 mg, 0.013 mmol) were added to the solution of N,N-dimethylformamide/methanol (9:1, 2 mL) mixture and heated at 100° C. for 2 h. The reaction mixture was concentrated and extracted with ethyl acetate. The organic layer was dried over anhydrous sodium sulfate and concentrated, and then the obtained residue was purified by column chromatography (Dichloromethane/Methanol) to give the subject compound (71) as a white solid (12 mg, Yield: 23%).

$^1$H NMR (400 MHz, DMSO-d6) δ 8.75 (s, 2H), 8.26 (d, J=6.8 Hz, 1H), 7.27 (t, J=9.4 Hz, 2H), 4.74-4.62 (m, 1H), 3.78 (m, 2H), 3.51 (m, 2H), 3.26-3.22 (m, 2H), 2.92-2.84 (m, 2H), 2.32-2.24 (m, 4H); LCMS m/z 484[M+H]$^+$

Test Example. Evaluation of Inhibitory Activity Against Human Autotaxin Protein (1) Method The solution of each synthesized compound (80 uM, 100% dimethyl sulfoxide) was sequentially diluted 5 times with dimethyl sulfoxide to prepare 6 concentrations. Each concentration of compound was diluted two-fold with 1× test buffer (50 mM Tris-Cl (pH 8.0), 5 mM KCl, 1 mM CaCl$_2$), 1 mM MgCl$_2$, 140 mM NaCl, deionized water, 1 mg/mL BSA), and 1 uL (1.25% dimethyl sulfoxide) of this diluted mixture was dispensed into each well of a 96 well clear round bottom plate. 9 uL of 1× test buffer were added to each well, followed by the addition of 20 uL of 240 nM human Autotaxin protein (buffer: 50 mM Tris-HCl, pH 8.0, with 150 mM sodium chloride and 20% glycerol). 10 uL of sonicated 360 uM 18:1 LysoPC (diluted with 1× test buffer) were added to each well. The reaction was performed for 2 hours in a shaking incubator at 37° C., and a secondary reaction mixture (choline assay kit, KA1662) (65 uL of 1× test buffer: 1 uL of choline oxidase: 1 uL of dye probe) was prepared. 60 uL of the secondary reaction mixture were added to the reaction plate and reacted on a shaker for 30 minutes. Using a SpectraMax iD3 microplate reader, the absorbance was measured at a wavelength of 570 nm. The percentage of inhibition activity (% inhibition) was calculated by the Formula: (1−Absorbance$_{testgroup}$/Absorbance$_{control\ group}$)×100.

(2) Result

The percentage of inhibition activity against Autotaxin protein was calculated for compounds of Example 1 to 71, which is shown in Table 1 below.

TABLE 1

| Example | inhibition (%) at 500 nM |
|---|---|
| 1 | 99 |
| 2 | 100 |
| 3 | 100 |
| 4 | 90 |
| 5 | 100 |
| 6 | 91 |
| 7 | 40 |
| 8 | 14 |
| 9 | 81 |
| 10 | 75 |
| 11 | 99 |
| 12 | 84 |
| 13 | 75 |
| 14 | 5 |
| 15 | 100 |
| 16 | 84 |
| 17 | 92 |
| 18 | 85 |
| 19 | 43 |
| 20 | 14 |
| 21 | 64 |
| 22 | 17 |
| 23 | 20 |
| 24 | 30.2 |
| 25 | 31.1 |
| 26 | 27.9 |
| 27 | 29 |
| 28 | 52.5 |
| 29 | 90.8 |
| 30 | 97.8 |
| 31 | 8.1 |
| 32 | 34.3 |
| 33 | 78.4 |
| 34 | 17.3 |
| 35 | 96 |
| 36 | 53.4 |
| 37 | 93.2 |
| 38 | 53.2 |
| 39 | 97.2 |
| 40 | 68.5 |
| 41 | 40.6 |
| 42 | 8.6 |
| 43 | 4.6 |
| 44 | 71.3 |
| 45 | 1.6 |
| 46 | 1 |
| 47 | 29.2 |
| 48 | 3.4 |
| 49 | 1.2 |
| 50 | 7 |
| 51 | 13.2 |
| 52 | 4.8 |
| 53 | 10.2 |
| 54 | 95.3 |
| 55 | 52 |
| 56 | 55.8 |
| 57 | 88.1 |
| 58 | 84 |
| 59 | 98.5 |
| 60 | 95.3 |
| 61 | 70 |
| 62 | 70.2 |
| 63 | 42.9 |
| 64 | 28.1 |
| 65 | 58 |
| 66 | 86.8 |
| 67 | 30.9 |
| 68 | 87.1 |
| 69 | 66.8 |
| 70 | 97.9 |
| 71 | 98.6 |

All synthesized compounds of Example 1 to Example 71 showed excellent inhibitory activity against human Autotaxin protein.

The foregoing description of the invention is for illustrative purposes only, and it will be readily apparent to those skilled in the art to which the invention belongs that varying substitutions and modifications may be made to the invention disclosed herein without departing from the spirit of the invention or essential features of the invention. It should therefore be understood that the embodiments described above are for the purpose of illustration of the invention only and are not intended in any way to limit the scope of the present invention. For example, each of the components described in a single form may also be implemented in a distributed manner, and similarly, components described as distributed may also be implemented in a combined form.

The scope of the invention is indicated by the following patent claims. The meaning and scope of the patent claims and all modifications or variations derived from their equivalents are considered to be falling within the scope of the invention.

What is claimed is:

1. A piperidine derivative compound of Formula 1, a hydrate thereof, a solvate thereof, or a pharmaceutically acceptable salt thereof:

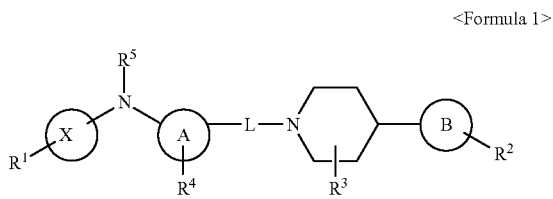

<Formula 1> wherein:
- X is an aryl-$C_{1-4}$ alkyl; a fused bicyclic ring in which an aryl ring is fused with a non-aromatic cycloalkyl ring, a fused bicyclic ring in which a heteroaryl ring having 1 to 3 of N is fused with a non-aromatic cycloalkyl ring; or a fused bicyclic ring in which an aryl ring is fused with a non-aromatic heterocycle ring having 1 to 3 of O, wherein X is substituted with one or more $R^1$ or not substituted with $R^1$,
- A is a 5- to 6-membered heteroaryl having 1 to 3 heteroatom(s) selected from the group consisting of N, O and S,
- L is —$(CH_2)_3$—; —$(CH_2)_a CO$—; —$(CH)_a CO$—; —$(CH_2)_b (CH_2)_c CO$—; or a 5-membered aromatic or non-aromatic heterocycle having 1 to 3 heteroatom(s) selected from the group consisting of N and O, wherein a, b, c are independently an integer of 1 to 5,
- B is COOH; $CH_2COOH$; CONHOH; $SO_2NH_2$; a 4- to 5-membered non-aromatic heterocycle having 1 to 3 heteroatom(s) selected from the group consisting of N and O; or a 5-membered heteroaryl having 1 to 4 heteroatom(s) selected from the group consisting of N and O,
- $R^1$ is halogen or $C_{1-4}$ alkylsulfonyl,
- $R^2$ is hydrogen, $C_{1-4}$ alkyl, $C_{1-4}$ haloalkyl, hydroxy, oxo (O) or aryl $C_{1-4}$ alkyl,
- $R^3$ is hydrogen, $C_{1-4}$ alkyl, $C_{1-4}$ alkoxy or halogen,
- $R^4$ is hydrogen, halogen or $C_{1-4}$ alkyl, and
- $R^5$ is hydrogen or $C_{1-4}$ alkyl.

2. The piperidine derivative compound, a hydrate thereof, a solvate thereof or a pharmaceutically acceptable salt thereof of claim 1, characterized in that X is one selected from the group consisting of benzyl, phenethyl, dihydroindenyl, dihydrocyclopentapyrazinyl and benzodioxolyl.

3. The piperidine derivative compound, a hydrate thereof, a solvate thereof or a pharmaceutically acceptable salt thereof of claim 1, characterized in that A is one selected from the group consisting of pyridine, pyrimidine, pyridazine, pyrazine, oxadiazole and thiadiazole.

4. The piperidine derivative compound, a hydrate thereof, a solvate thereof or a pharmaceutically acceptable salt thereof of claim 1, characterized in that L is one selected from the group consisting of —$(CH_2)_3$—, —$(CH_2)_2CO$—, —$(CH_2)_3CO$—, —$(CH)_2CO$—, —$CH_2OCH_2CO$—, oxazole, isoxazole, dihydroisoxazole and oxadiazole.

5. The piperidine derivative compound, a hydrate thereof, a solvate thereof or a pharmaceutically acceptable salt thereof of claim 1, characterized in that B is one selected from the group consisting of carboxyl, carboxymethyl, carboxamido, sulfonamide, azetidine, oxadiazole, imidazole, triazole and tetrazole.

6. The piperidine derivative compound, a hydrate thereof, a solvate thereof or a pharmaceutically acceptable salt thereof of claim 1, characterized in that $R^1$ is one selected from the group consisting of F, Cl, Br and methylsulfonyl.

7. The piperidine derivative compound, a hydrate thereof, a solvate thereof or a pharmaceutically acceptable salt thereof of claim 1, characterized in that $R^2$ is one selected from the group consisting of hydrogen, methyl, difluoromethyl, trifluoromethyl, hydroxy, oxo (O) and benzyl.

8. The piperidine derivative compound, a hydrate thereof, a solvate thereof or a pharmaceutically acceptable salt thereof of claim 1, characterized in that $R^3$ is one selected from the group consisting of hydrogen, methyl, methoxy and F.

9. The piperidine derivative compound, a hydrate thereof, a solvate thereof or a pharmaceutically acceptable salt thereof of claim 1, characterized in that $R^4$ is one selected from the group consisting of hydrogen, Cl and methyl.

10. The piperidine derivative compound, a hydrate thereof, a solvate thereof or a pharmaceutically acceptable salt thereof of claim 1, characterized in that $R^5$ is hydrogen or alkyl.

11. The piperidine derivative compound of claim 1 selected from the group consisting of the following compounds, a hydrate thereof, a solvate thereof or a pharmaceutically acceptable salt thereof:

[1] 5-(5-(4-(1H-1,2,3-triazol-5-yl)piperidin-1-yl)-1,3,4-oxadiazol-2-yl)-N-(2,3-dihydro-1H-inden-2-yl)pyrimidin-2-amine,

[2] 5-(5-(4-(1H-1,2,3-triazol-5-yl)piperidin-1-yl)-1,3,4-oxadiazol-2-yl)-N-(5-fluoro-2,3-dihydro-1H-inden-2-yl)pyrimidin-2-amine,

[3] 5-(5-(4-(1H-1,2,3-triazol-5-yl)piperidin-1-yl)-1,3,4-oxadiazol-2-yl)-N-(5-chloro-2,3-dihydro-1H-inden-2-yl)pyrimidin-2-amine,

[4] 5-(5-(4-(1H-1,2,3-triazol-5-yl)piperidin-1-yl)-1,3,4-oxadiazol-2-yl)-N-(5-bromo-2,3-dihydro-1H-inden-2-yl)pyrimidin-2-amine,

[5] 5-(5-(4-(1H-1,2,3-triazol-5-yl)piperidin-1-yl)-1,3,4-oxadiazol-2-yl)-N-(5,6-difluoro-2,3-dihydro-1H-inden-2-yl)pyrimidin-2-amine,

[6] 5-(5-(4-(1H-1,2,3-triazol-5-yl)piperidin-1-yl)-1,3,4-oxadiazol-2-yl)-N-(5,6-dichloro-2,3-dihydro-1H-inden-2-yl)pyrimidin-2-amine,

[7] N-(5-(5-(4-(1H-1,2,3-triazol-5-yl)piperidin-1-yl)-1,3,4-oxadiazol-2-yl)pyrimidin-2-yl)-6,7-dihydro-5H-cyclopenta[b]pyrazin-6-amine,

[8] 6-(5-(4-(1H-1,2,3-triazol-5-yl)piperidin-1-yl)-1,3,4-oxadiazol-2-yl)-N-(2,3-dihydro-1H-inden-2-yl)pyridazin-3-amine,

[9] 5-(5-(4-(1H-1,2,4-triazol-1-yl)piperidin-1-yl)-1,3,4-oxadiazol-2-yl)-N-(2,3-dihydro-1H-inden-2-yl)pyrimidin-2-amine,

[10] N-(2,3-dihydro-1H-inden-2-yl)-5-(5-(4-(3-methyl-1H-1,2,4-triazol-1-yl)piperidin-1-yl)-1,3,4-oxadiazol-2-yl)pyrimidin-2-amine,

[11] N-(5-bromo-2,3-dihydro-1H-inden-2-yl)-5-(5-(2-methyl-4-(1H-1,2,3-triazol-5-yl)piperidin-1-yl)-1,3,4-oxadiazol-2-yl)pyrimidin-2-amine,

[12] 5-(5-(4-(1H-1,2,3-triazol-5-yl)piperidin-1-yl)-1,3,4-oxadiazol-2-yl)-N-(5-bromo-2,3-dihydro-1H-inden-2-yl)pyridin-2-amine,

[13] 5-(5-(4-(1H-1,2,3-triazol-5-yl)piperidin-1-yl)-1,3,4-oxadiazol-2-yl)-N-(5-bromo-2,3-dihydro-1H-inden-2-yl)pyrazin-2-amine,

[14] 5-(5-(4-(1H-1,2,3-triazol-5-yl)piperidin-1-yl)-1,3,4-oxadiazol-2-yl)-N-(5-bromo-2,3-dihydro-1H-inden-2-yl)-4-chloropyridin-2-amine,
[15] 5-(5-(4-(1H-1,2,3-triazol-5-yl)piperidin-1-yl)-1,3,4-oxadiazol-2-yl)-N-(3,5-dichlorobenzyl)pyrimidin-2-amine,
[16] 5-(5-(4-(1H-1,2,3-triazol-5-yl)piperidin-1-yl)-1,3,4-oxadiazol-2-yl)-N-(3,5-dichlorophenethyl)pyrimidin-2-amine,
[17] 1-(4-(1H-1,2,3-triazol-5-yl)piperidin-1-yl)-3-(2-((2,3-dihydro-1H-inden-2-yl)amino)pyrimidin-5-yl)propan-1-one,
[18] 1-(4-(1H-imidazol-5-yl)piperidin-1-yl)-3-(2-((2,3-dihydro-1H-inden-2-yl)amino)pyrimidin-5-yl)propan-1-one,
[19] 1-(4-(1H-1,2,3-triazol-5-yl)piperidin-1-yl)-4-(5-((2,3-dihydro-1H-inden-2-yl)amino)-1,3,4-thiadiazol-2-yl)butan-1-one,
[20] 1-(4-(1H-imidazol-5-yl)piperidin-1-yl)-4-(5-((2,3-dihydro-1H-inden-2-yl)amino)-1,3,4-thiadiazol-2-yl)butan-1-one,
[21] 1-(4-(1H-1,2,3-triazol-5-yl)piperidin-1-yl)-4-(5-((2,3-dihydro-1H-inden-2-yl)amino)-1,3,4-oxadiazol-2-yl)butan-1-one,
[22] 1-(4-(1H-imidazol-5-yl)piperidin-1-yl)-4-(5-((2,3-dihydro-1H-inden-2-yl)amino)-1,3,4-oxadiazol-2-yl)butan-1-one,
[23] 1-(4-(1H-1,2,3-triazol-5-yl)piperidin-1-yl)-2-((5-((2,3-dihydro-1H-inden-2-yl)amino)-1,3,4-thiadiazol-2-yl)methoxy)ethan-1-one,
[24] N-(5,6-difluoro-2,3-dihydro-1H-inden-2-yl)-5-(5-(4-(5-(trifluoromethyl)-1,3,4-oxadiazol-2-yl)piperidin-1-yl)-1,3,4-oxadiazol-2-yl)pyrimidin-2-amine,
[25] N-(5,6-difluoro-2,3-dihydro-1H-inden-2-yl)-5-(5-(4-(5-(difluoromethyl)-1,3,4-oxadiazol-2-yl)piperidin-1-yl)-1,3,4-oxadiazol-2-yl)pyrimidin-2-amine,
[26] 5-(5-(4-(1,2,4-oxadiazol-3-yl)piperidin-1-yl)-1,3,4-oxadiazol-2-yl)-N-(5,6-difluoro-2,3-dihydro-1H-inden-2-yl)pyrimidin-2-amine,
[27] 5-(5-(4-(1,3,4-oxadiazol-2-yl)piperidin-1-yl)-1,3,4-oxadiazol-2-yl)-N-(5,6-difluoro-2,3-dihydro-1H-inden-2-yl)pyrimidin-2-amine,
[28] 5-(5-(4-(1H-tetrazol-1-yl)piperidin-1-yl)-1,3,4-oxadiazol-2-yl)-N-(5,6-difluoro-2,3-dihydro-1H-inden-2-yl)pyrimidin-2-amine,
[29] N-(5,6-difluoro-2,3-dihydro-1H-inden-2-yl)-5-(5-(4-(4-methyl-1H-1,2,3-triazol-5-yl)piperidin-1-yl)-1,3,4-oxadiazol-2-yl)pyrimidin-2-amine,
[30] (E)-1-(4-(1H-1,2,3-triazol-5-yl)piperidin-1-yl)-3-(2-((5,6-difluoro-2,3-dihydro-1H-inden-2-yl)amino)pyrimidin-5-yl)prop-2-en-1-one,
[31] 5-(5-(4-(1-benzyl-1H-1,2,3-triazol-5-yl)piperidin-1-yl)oxazol-2-yl)-N-(2,3-dihydro-1H-inden-2-yl)pyrimidin-2-amine,
[32] 5-(5-(4-(1H-1,2,3-triazol-5-yl)piperidin-1-yl)-1,3,4-oxadiazol-2-yl)-N-(5,6-difluoro-2,3-dihydro-1H-inden-2-yl)-N-methylpyrimidin-2-amine,
[33] N-(5,6-difluoro-2,3-dihydro-1H-inden-2-yl)-5-(5-(4-(1-methyl-1H-1,2,3-triazol-5-yl)piperidin-1-yl)-1,3,4-oxadiazol-2-yl)pyrimidin-2-amine,
[34] N-(5,6-difluoro-2,3-dihydro-1H-inden-2-yl)-5-(5-(4-(1-methyl-1H-1,2,3-triazol-4-yl)piperidin-1-yl)-1,3,4-oxadiazol-2-yl)pyrimidin-2-amine,
[35] N-indan-2-yl-5-[3-[4-(1H-triazol-5-yl)-1-piperidyl]-4,5-dihydroisoxazol-5-yl]pyrimidin-2-amine,
[36] 5-(3-(4-(1H-1,2,3-triazol-5-yl)piperidin-1-yl)isoxazol-5-yl)-N-(2,3-dihydro-1H-inden-2-yl)pyrimidin-2-amine,
[37] N-(5,6-difluoroindan-2-yl)-5-[3-[4-(1H-triazol-5-yl)-1-piperidyl]-4,5-dihydroisoxazol-5-yl]pyrimidin-2-amine,
[38] 5-(3-(4-(1H-1,2,3-triazol-5-yl)piperidin-1-yl)isoxazol-5-yl)-N-(5,6-difluoro-2,3-dihydro-1H-inden-2-yl)pyrimidin-2-amine,
[39] 5-(3-(4-(1H-1,2,3-triazol-5-yl)piperidin-1-yl)-4,5-dihydroisoxazol-5-yl)-N-(5-fluoro-2,3-dihydro-1H-inden-2-yl)pyrimidin-2-amine,
[40] 5-(3-(4-(1H-1,2,3-triazol-5-yl)piperidin-1-yl)isoxazol-5-yl)-N-(5-fluoro-2,3-dihydro-1H-inden-2-yl)pyrimidin-2-amine,
[41] N-[(3,5-difluorophenyl)methyl]-5-[3-[4-(1H-triazol-5-yl)-1-piperidyl]-4,5-dihydroisoxazol-5-yl]pyrimidin-2-amine,
[42] N-benzyl-5-[3-[4-(1H-triazol-5-yl)-1-piperidyl]-4,5-dihydroisoxazol-5-yl]pyrimidin-2-amine,
[43] N-[(3,4-difluorophenyl)methyl]-5-[3-[4-(1H-triazol-5-yl)-1-piperidyl]-4,5-dihydroisoxazol-5-yl]pyrimidin-2-amine,
[44] 5-(3-(4-(1H-1,2,3-triazol-5-yl)piperidin-1-yl)-4,5-dihydroisoxazol-5-yl)-N-(3,5-dichlorobenzyl)pyrimidin-2-amine,
[45] 5-(3-(4-(1H-1,2,3-triazol-5-yl)piperidin-1-yl)-4,5-dihydroisoxazol-5-yl)-N-(benzo[d][1,3]dioxol-5-ylmethyl)pyrimidin-2-amine,
[46] N-(1,3-benzodioxol-5-ylmethyl)-5-[3-[4-(1H-triazol-5-yl)-1-piperidyl]isoxazol-5-yl]pyrimidin-2-amine,
[47] 5-(3-(4-(1H-1,2,3-triazol-5-yl)piperidin-1-yl)-4,5-dihydroisoxazol-5-yl)-N-(3,5-dichlorophenethyl)pyrimidin-2-amine,
[48] 5-(3-(4-(1H-1,2,3-triazol-5-yl)piperidin-1-yl)-4,5-dihydroisoxazol-5-yl)-N-(3-(methylsulfonyl)benzyl)pyrimidin-2-amine,
[49] 5-(3-(4-(1H-1,2,3-triazol-5-yl)piperidin-1-yl)-4,5-dihydroisoxazol-5-yl)-N-(4-(methylsulfonyl)benzyl)pyrimidin-2-amine,
[50] 5-(3-(4-(1H-tetrazol-5-yl)piperidin-1-yl)-4,5-dihydroisoxazol-5-yl)-N-(2,3-dihydro-1H-inden-2-yl)pyrimidin-2-amine,
[51] 5-(3-(4-(5-(difluoromethyl)-1,3,4-oxadiazol-2-yl)piperidin-1-yl)-4,5-dihydroisoxazol-5-yl)-N-(2,3-dihydro-1H-inden-2-yl)pyrimidin-2-amine,
[52] 5-(3-(4-(1H-tetrazol-5-yl)piperidin-1-yl)-4,5-dihydroisoxazol-5-yl)-N-(5,6-difluoro-2,3-dihydro-1H-inden-2-yl)pyrimidin-2-amine,
[53] N-(5-fluoro-2,3-dihydro-1H-inden-2-yl)-5-(3-(4-(5-(trifluoromethyl)-1,3,4-oxadiazol-2-yl)piperidin-1-yl)-4,5-dihydroisoxazol-5-yl)pyrimidin-2-amine,
[54] N-(5,6-difluoro-2,3-dihydro-1H-inden-2-yl)-5-(5-(2-methyl-4-(1H-1,2,3-triazol-5-yl)piperidin-1-yl)-1,3,4-oxadiazol-2-yl)pyrimidin-2-amine,
[55] 5-(5-(4-(1H-1,2,3-triazol-5-yl)piperidin-1-yl)-1,3,4-oxadiazol-2-yl)-N-(benzo[d][1,3]dioxol-5-ylmethyl)pyrimidin-2-amine,
[56] 5-(5-(4-(1H-1,2,3-triazol-5-yl)piperidin-1-yl)-1,3,4-oxadiazol-2-yl)-N-(3,4-dichlorobenzyl)pyrimidin-2-amine,
[57] 5-(5-(4-(1H-1,2,3-triazol-5-yl)piperidin-1-yl)-1,3,4-oxadiazol-2-yl)-N-(3,5-difluorobenzyl)pyrimidin-2-amine,

[58] 5-(5-(4-(1H-1,2,3-triazol-5-yl)piperidin-1-yl)-1,3,4-oxadiazol-2-yl)-N-(3,4-difluorobenzyl)pyrimidin-2-amine,

[59] 5-(5-(4-(1H-1,2,3-triazol-5-yl)piperidin-1-yl)-1,3,4-oxadiazol-2-yl)-N-(3,5-dibromobenzyl)pyrimidin-2-amine,

[60] 5-(5-(4-(1H-1,2,3-triazol-5-yl)piperidin-1-yl)-1,3,4-oxadiazol-2-yl)-N-(5-bromo-2,3-dihydro-1H-inden-2-yl)-4-methylpyrimidin-2-amine,

[61] 5-(5-(4-(1H-1,2,3-triazol-5-yl)piperidin-1-yl)-1,3,4-oxadiazol-2-yl)-N-(5,6-dibromo-2,3-dihydro-1H-inden-2-yl)-4-methylpyrimidin-2-amine,

[62] 5-(3-(4-(1H-1,2,3-triazol-4-yl)piperidin-1-yl)propyl)-N-(2,3-dihydro-1H-inden-2-yl)pyrimidin-2-amine,

[64] 1-(1-(5-(2-((5,6-difluoro-2,3-dihydro-1H-inden-2-yl)amino)pyrimidin-5-yl)-1,3,4-oxadiazol-2-yl)piperidin-4-yl)azetidin-3-ol,

[65] 1-(5-(2-((5,6-difluoro-2,3-dihydro-1H-inden-2-yl)amino)pyrimidin-5-yl)-1,3,4-oxadiazol-2-yl)piperidine-4-sulfonamide,

[66] 5-(1-(5-(2-((5,6-difluoro-2,3-dihydro-1H-inden-2-yl)amino)pyrimidin-5-yl)-1,3,4-oxadiazol-2-yl)piperidin-4-yl)-1,3,4-oxadiazol-2(3H)-one,

[67] 1-(5-(2-((5,6-difluoro-2,3-dihydro-1H-inden-2-yl)amino)pyrimidin-5-yl)-1,3,4-oxadiazol-2-yl)piperidine-4-carboxylic acid,

[68] 2-(1-(5-(2-((5,6-difluoro-2,3-dihydro-1H-inden-2-yl)amino)pyrimidin-5-yl)-1,3,4-oxadiazol-2-yl)piperidin-4-yl)acetic acid,

[69] 1-(5-(2-((5,6-difluoro-2,3-dihydro-1H-inden-2-yl)amino)pyrimidin-5-yl)-1,3,4-oxadiazol-2-yl)-N-hydroxypiperidine-4-carboxamide,

[70] N-(5,6-difluoro-2,3-dihydro-1H-inden-2-yl)-5-(5-(4-methoxy-4-(1H-1,2,3-triazol-4-yl)piperidin-1-yl)-1,3,4-oxadiazol-2-yl)pyrimidin-2-amine, and

[71] N-(5,6-difluoro-2,3-dihydro-1H-inden-2-yl)-5-(5-(4-fluoro-4-(1H-1,2,3-triazol-5-yl)piperidin-1-yl)-1,3,4-oxadiazol-2-yl)pyrimidin-2-amine.

12. N-(5,6-difluoro-2,3-dihydro-1H-inden-2-yl)-5-(5-(4-morpholinopiperidin-1-yl)-1,3,4-oxadiazol-2-yl)pyrimidin-2-amine, a hydrate thereof, a solvate thereof or a pharmaceutically acceptable salt thereof.

13. A pharmaceutical composition for preventing or treating radiation-induced fibrosis, comprising the piperidine derivative compound, a hydrate thereof, a solvate thereof or a pharmaceutically acceptable salt thereof of claim 1.

14. A pharmaceutical composition for preventing or treating cancer and cancer metastasis, comprising the piperidine derivative compound, a hydrate thereof, a solvate thereof or a pharmaceutically acceptable salt thereof of claim 1.

15. A pharmaceutical composition comprising the piperidine derivative compound, a hydrate thereof, a solvate thereof or a pharmaceutically acceptable salt thereof of claim 1, for preventing or treating one or more diseases selected from the group consisting of a fibrotic disease selected from idiopathic pulmonary fibrosis (IPF), interstitial lung disease, liver fibrosis, liver cirrhosis, non-alcoholic steatohepatitis, myocardial and vascular fibrosis, renal fibrosis, cutaneous fibrosis, glomerulosclerosis, myocardial fibrosis and vascular fibrosis; an inflammatory disease selected from rheumatoid arthritis, osteoarthritis, atopic dermatitis, inflammatory bowel disease, inflammatory airway disease, chronic obstructive pulmonary disease (COPD) and asthma; an autoimmune disease selected from multiple sclerosis and scleroderma; a respiratory disease selected from asbestos-induced pulmonary fibrosis and acute respiratory distress syndrome (ARDS); a cardiovascular disease selected from arteriosclerosis, myocardial infarction, arterial and pulmonary hypertension, cardiac arrhythmia, stroke and other vascular damage; a metabolic disease selected from obesity and diabetes; cancer and cancer metastasis selected from breast cancer, ovarian cancer, lung cancer, prostate cancer, mesothelioma, glioma, liver carcinoma, gastrointestinal cancer, pancreatic cancer, and its progression and metastatic invasion; an ocular disease selected from proliferative retinopathy, non-proliferative retinopathy and non-proliferative diabetic retinopathy, dry and wet age-related macular degeneration (AMD), macular edema, central artery/venous occlusion, traumatic injury, and glaucoma; cholestatic form and other forms of chronic pruritus; and acute or chronic organ transplant rejection.

\* \* \* \* \*

UNITED STATES PATENT AND TRADEMARK OFFICE
CERTIFICATE OF CORRECTION

PATENT NO. : 12,145,929 B2
APPLICATION NO. : 18/560806
DATED : November 19, 2024
INVENTOR(S) : Lee et al.

Page 1 of 1

It is certified that error appears in the above-identified patent and that said Letters Patent is hereby corrected as shown below:

In the Claims

Column 89, Claim 1, Line 29:
Please delete "-$(CH_2)_b(CH_2)_cCO$-;"
And replace with -- -$(CH_2)_bO(CH_2)_cCO$-; --

Signed and Sealed this
Eleventh Day of March, 2025

Coke Morgan Stewart
*Acting Director of the United States Patent and Trademark Office*